(12) United States Patent
Qin et al.

(10) Patent No.: US 11,834,509 B2
(45) Date of Patent: Dec. 5, 2023

(54) THYMIC STROMAL LYMPHOPOIETIN RECEPTOR-SPECIFIC CHIMERIC ANTIGEN RECEPTORS AND METHODS USING SAME

(71) Applicant: The United States of America, as represented by the Secretary, Department of Health and Human Services, Bethesda, MD (US)

(72) Inventors: Haiying Qin, Potomac, MD (US); Terry J. Fry, Bethesda, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 706 days.

(21) Appl. No.: 16/860,216

(22) Filed: Apr. 28, 2020

(65) Prior Publication Data

US 2020/0308289 A1 Oct. 1, 2020

Related U.S. Application Data

(62) Division of application No. 15/101,583, filed as application No. PCT/US2014/063096 on Oct. 30, 2014, now Pat. No. 10,676,528.

(60) Provisional application No. 61/991,697, filed on May 12, 2014, provisional application No. 61/912,948, filed on Dec. 6, 2013.

(51) Int. Cl.
| | |
|---|---|
| *A61P 35/02* | (2006.01) |
| *C07K 16/28* | (2006.01) |
| *C07K 14/725* | (2006.01) |
| *C07K 16/30* | (2006.01) |
| *C07K 14/705* | (2006.01) |
| *C07K 14/715* | (2006.01) |

(52) U.S. Cl.
CPC ...... *C07K 16/2866* (2013.01); *C07K 14/7051* (2013.01); *C07K 14/70517* (2013.01); *C07K 14/7151* (2013.01); *C07K 16/2803* (2013.01); *C07K 16/3061* (2013.01); *C07K 2317/524* (2013.01); *C07K 2317/526* (2013.01); *C07K 2317/565* (2013.01); *C07K 2317/622* (2013.01); *C07K 2319/00* (2013.01); *C07K 2319/02* (2013.01); *C07K 2319/03* (2013.01); *C07K 2319/33* (2013.01)

(58) Field of Classification Search
None
See application file for complete search history.

(56) References Cited

U.S. PATENT DOCUMENTS

| | | | |
|---|---|---|---|
| 5,859,205 A | 1/1999 | Adair et al. | |
| 8,211,422 B2 | 7/2012 | Eshhar et al. | |
| 8,344,110 B2 | 1/2013 | Saris et al. | |
| 8,475,793 B2 | 7/2013 | De Waal Malefyt et al. | |
| 9,346,854 B2 | 5/2016 | Shai et al. | |
| 9,597,357 B2 | 3/2017 | Gregory et al. | |
| 10,172,886 B2 | 1/2019 | Vankayalapati et al. | |
| 2010/0105136 A1 | 4/2010 | Carter et al. | |
| 2011/0020369 A1 | 1/2011 | De Waal Malefyt et al. | |
| 2012/0020988 A1 | 1/2012 | Auer et al. | |
| 2014/0322275 A1 | 10/2014 | Brogdon et al. | |

FOREIGN PATENT DOCUMENTS

| | | |
|---|---|---|
| CN | 101605814 A | 12/2009 |
| CN | 109843922 A | 6/2019 |
| KR | 1020160085347 A | 7/2016 |
| WO | WO 2008/045437 A2 | 4/2008 |
| WO | WO 2008/076321 A1 | 6/2008 |
| WO | WO 2011/014871 A1 | 2/2011 |
| WO | WO 2012/079000 A1 | 6/2012 |
| WO | WO 2013/103614 A1 | 7/2013 |
| WO | WO 2013/123061 A1 | 8/2013 |
| WO | WO 2015/118124 A1 | 8/2015 |
| WO | WO 2018/045325 A1 | 3/2018 |

OTHER PUBLICATIONS

He et al. (Ann. N.Y. Acad. Sci. 1183 (2010) 13-24, 2009). (Year: 2009).*
Wong et al. (Am J Respir Cell Mol Biol. Sep. 2010;43(3):305-15). (Year: 2010).*
Ghirelli et al. (Oncoimmunology, 2016, vol. 5, No. 8, e1178438). (Year: 2016).*
Demehri et al. (J Clin Invest. 2016;126(4):1458-1470). (Year: 2016).*
McKinney, (J Neurol Neurosurg Psychiatry 2004;75(Suppl II):ii12-ii17, at pp. ii15-ii16). (Year: 2004).*
GenBank Accession No. BAG84574, "Anti-plumbagin single-chain variable fragment antibody, partial (synthetic construct)" Nov. 19, 2008.
Yi et al., "New Strategy of Tumor Immunotherapy Based on Chimeric Antigen Receptor Engineered T Cells," *Chin J. Cancer Biother.* 20(4): 383-390 (2013).
Almasbak et al., "Inclusion of an IgG1-Fc Spacer Abrogates Efficacy of CD19 CAR T Cells in a Xenograft Mouse Model," *Gene Therapy*, 22: 391-403 (2015), published online Feb. 5, 2015.

(Continued)

*Primary Examiner* — Zachary S Skelding
(74) *Attorney, Agent, or Firm* — Leydig, Voit & Mayer, Ltd.

(57) ABSTRACT

The invention provides a chimeric antigen receptor (CAR) comprising an antigen binding domain specific for TSLPR, a transmembrane domain, and an intracellular T cell signaling domain. Nucleic acids, recombinant expression vectors, host cells, populations of cells, antibodies, or antigen binding portions thereof, and pharmaceutical compositions relating to the CARs are disclosed. Methods of detecting the presence of a proliferative disorder, e.g., cancer, in a mammal and methods of treating or preventing a proliferative disorder, e.g., cancer, in a mammal are also disclosed.

22 Claims, 47 Drawing Sheets

Specification includes a Sequence Listing.

(56) References Cited

OTHER PUBLICATIONS

Jonnalagadda et al., "Chimeric Antigen Receptors with Mutated IgG4 Fc Spacer Avoid Fc Receptor Binding and Improve T Cell Persistence and Antitumor Efficacy," *Molecular Therapy*, 23(4): 757-768 (2015), published online Feb. 17, 2015.

Borowski et al., "Expression Analysis and Specific Blockade of the Receptor for Human Thymic Stromal Lymphopoietin (TSLP) by Novel Antibodies to the Human TSLPRα Receptor Chain," *Cytokine*, 61:546-555 (2013).

Brentjens et al., "Safety and persistence of adoptively transferred autologous CD19-targeted T cells in patients with relapsed or chemotherapy refractory B-cell leukemias,"*Blood*, 118(180) 4817-4828 (published online Aug. 17, 2011).

Bridgeman et al., "Building Better Chimeric Antigen Receptors for Adoptive T Cell Therapy," *Current Gene Therapy*, 10:77-90 (2010).

Brudno et al., "Allogeneic T Cells That Express an Anti-CD19 Chimeric Antigen Receptor Induce Remissions of B-Cell Malignancies That Progress After Allogeneic Hematopoietic Stem-Cell Transplantation Without Causing Graft-Versus-Host Disease," *J Clin Oncology* 34(10):1112-1121 (Apr. 1, 2016).

Chiba, "Leukemia: recent progress in diagnosis and treatment topics: I. Recent findings in pathogenesis and pathophysiology; 2. Cytogenetic and genetic abnormalities in leukemia," *The Journal of Japanese Society of Internal Medicine*, 102:1661-1666 (2013).

Curran et al., "Chimeric antigen receptors for T Cell Immunotherapy: Current understanding and future direction," *Journal of Gene Medicine*, 14(6):405-415, (2012).

Gauvreau et al., "Effects of an anti-TSLP antibody on allergen-induced asthmatic responses," *N. Engl. J. Med.*, 370(22):2102-2110 (May 20, 2014).

Grupp et al., "Chimeric antigen receptor-modified T cells for acute lymphoid leukemia," *N. Engl. J. Med.*, 368(16): 1509-1518 (Mar. 25, 2013).

Hudecek et al., "The nonsignaling extracellular spacer domain of chimeric antigen receptors is decisive for in vivo antitumor activity," *Cancer Immunol. Res.*, 3 (2):125-135 (2015) published online Sep. 11, 2014.

Huston et al., "Protein Engineering of Antibody Binding Sites: Recovery of Specific Activity in an Anti-Digoxin Singke-Chain Fv Analogue Produced in *Escherichia coli*," *PNAS U.S.A.* 85(16):5879-83 (1988).

International Preliminary Report on Patentability, Application No. PCT/US2014/063096, dated Jun. 16, 2016.

International Search Report, Application No. PCT/US2014/063096, dated Mar. 3, 2015.

Japanese Patent Office, Office Action dated Sep. 11, 2018, in Application No. 2016-536812, 7 pages.

Kettleborough et al., "Optimization of primers for cloning libraries of mouse immunoglobulin genes using the polymerase chain reaction," *Eur. J. Immunol.*, 23 (1): 206-211 (1993).

Kozlov et al., "Modern problems of cancer immuno-Therapy," БЮЛЛЕТЕНЬ СО РАМН,2(112):13-19, (2004).

Lu et al., "TSLP and IL-7 use two different mechanisms to regulate human CD4+ T cell homeostasis," *J. Exp. Med.*, 206(10):2111-2119 (Sep. 28, 2009).

Magalhaes et al., "Nucleotide oligomerization domain-containing proteins instruct T cell helper type 2 immunity through stromal activation," *Proc. Natl. Acad. Sci. U.S.A.*, 108 (36):14896-14901 (Sep. 6, 2011) with correction.

Micklethwaite et al., "Derivation of human T lymphocytes from cord blood and peripheral blood with antiviral and antileukemic specificity from a single culture as protection against infection and relapse after stem cell transplantation," *Blood*, 115 (13): 2695-2703 (2010) published online Jan. 28, 2010.

Milone et al., "Chimeric receptors containing CD137 signal transduction domains mediate enhanced survival of T cells and increased antileukemic efficacy in vivo," *Mol. Ther.*, 17(8): 1453-1464 (Aug. 2009) published online Apr. 21, 2009.

Nakajima et al., "Langerhans cells are critical in epicutaneous sensitization with protein antigen via thymic stromal lymphopoietin receptor signaling," *J. Allergy Clin. Immunol* 129(4): 1048-1055 (2012) published online Mar. 2, 2012.

Padlan, "Anatomy of the Antibody Molecule," *Mol Immunol*, 31(3):169-217 (Feb. 1994).

Patton et al., "The development and survival but not function of follicular B cells is dependent on IL-7Rα Tyr449 signaling," *PloS One*, 9(2), e88771 (Feb. 2014) published online Feb. 13, 2014.

Portolano et al., "Lack of Promiscuity in Autoantigen-Specific H and L Chain Combinations as Reveled by Human H and L Chain 'Roulette'," *J Immunol*, 150(3):880-7 (Feb. 1, 1993).

Portoles et al., "Monoclonal antibodies to murine CD3 epsilon define distinct epitopes, one of which may interact with CD4 during T cell activation," *The Journal of Immunology*, 142(12):4169-4175 (1989).

Qin et al., "Pre-Clinical Development of a Novel Chimerical Antigen Receptor Targeting High-Risk Pediatric ALL over-expressing Tslpr," poster presented at 55th ASH Annual Meeting and Exposition Abstract in New Orleans, LA, abstract No. 2665 (Dec. 7-10, 2013).

Qin et al., "Pre-Clinical Development of a Novel Chimerical Antigen Receptor Targeting High-Risk Pediatric ALL over-expressing Tslpr," program of 55th ASH Annual Meeting and Exposition Abstract in New Orleans, LA, abstract No. 2665 (Dec. 7-10, 2013).

Qin et al., "Pre-Clinical Development of a Novel Chimerical Antigen Receptor Targeting High-Risk Pediatric ALL Over-Expressing Tslpr," *Blood*, 122(21): 2665 (Nov. 15, 2013).

Qin et al., "Eradication of B-ALL using chimeric antigen receptor-expressing T cells targeting the TSLPR oncoprotein," *Blood*, 126(5): 629-639 (2015) published online Jun. 3, 2015.

Ramos et al., "Chimeric Antigen Receptor (CAR)-engineered Lymphocytes for Cancer Therapy," *Expert opinion on biological therapy*, 11(7): 855-873 (2011).

Rochman et al., "Cutting edge: direct action of thymic stromal lymphopoietin on activated human CD4+ T cells," *J. Immunol.*, 178(11), 6720-6724 (2007).

Russian Patent Office, Office Action dated Oct. 11, 2018, in Application No. 2016124670/10, 14 pages.

Sadelain et al., "The basic principles of chimeric antigen receptor design," *Cancer Discovery*, 3:388-398 (2013).

Tal et al., "Interleukin 7 and thymic stromal lymphopoietin: from immunity to leukemia," *Cell. Mol. Lif Sci.*, 71(3): 365-378 (2014), published online Apr. 27, 2013.

Tasian et al., "Understanding the Biology of CRLF2-Overexpressing Acute Lymphoblastic Leukemia," *Crit Rev Oncog.* 16(0):13-24 (2011).

Tran et al., "Production of Unique Immunotoxin Cancer Therapeutics in Algal Chloroplasts," *PNAS*, pp. E15-E22 (published online Dec. 10, 2012).

Written Opinion of the International Searching Authority, Application No. PCT/US2014/063096, dated Apr. 2015.

Yoda et al., "Functional screening identifies CRLF2 in precursor B-cell acute lymphoblastic leukemia," *Proc. Natl. Acad. Sci. U.S.A.*, 107(1): 252-257 (Jan. 5, 2010) published online Dec. 15, 2009.

Zhou et al., "Thymic stromal lymphopoietin as a key initiator of allergic airway inflammation in mice" *Nat. Immunol.* 6: 1047-53 (2005).

U.S. Appl. No. 15/101,583, filed Jun. 3, 2016.

\* cited by examiner

1 $V_H$
2 Glycine-Serine Linker
3 $V_L$
4 CD8 α hinge + CD8 TM
5 41BB ICD
6 CD3ζ
7 EF1α Promoter
8 cPPT
9 Partial *gag* sequence
10 U5
11 R
12 RSV Promoter
13 β lactamase
A NfeI
B BspEI

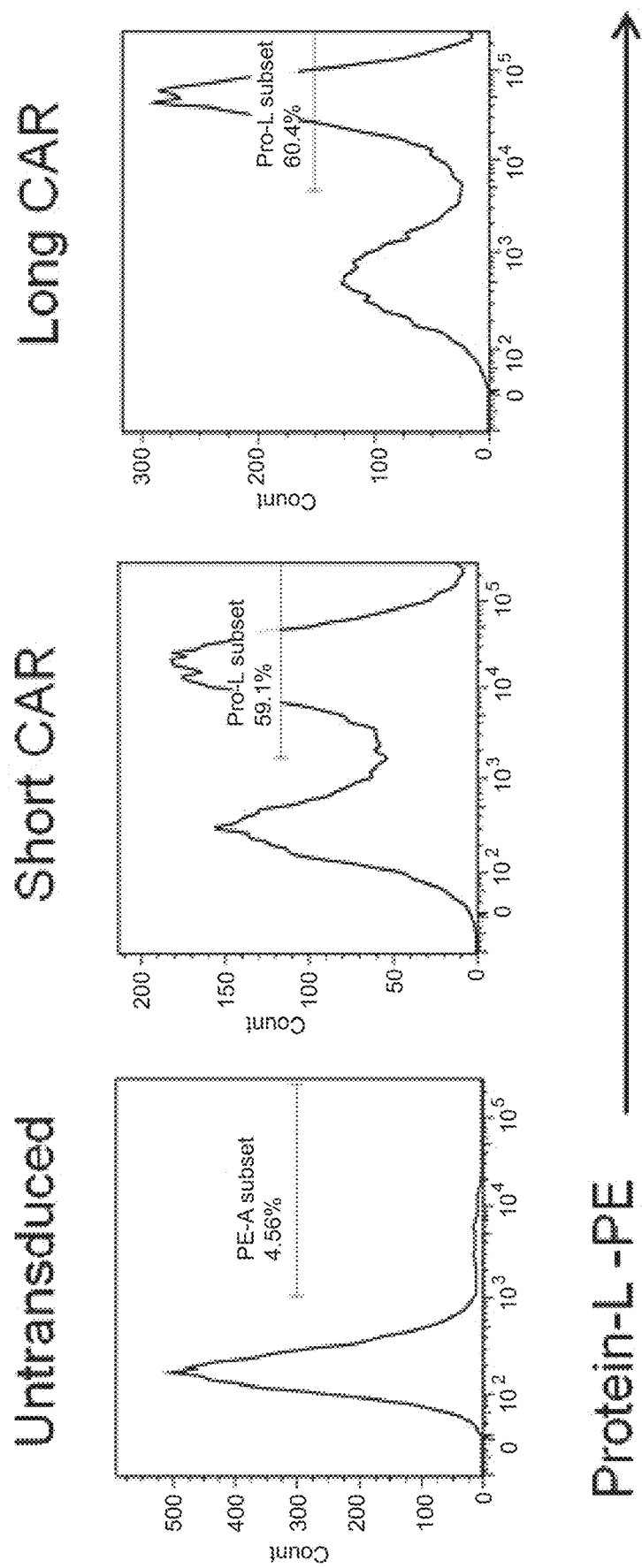

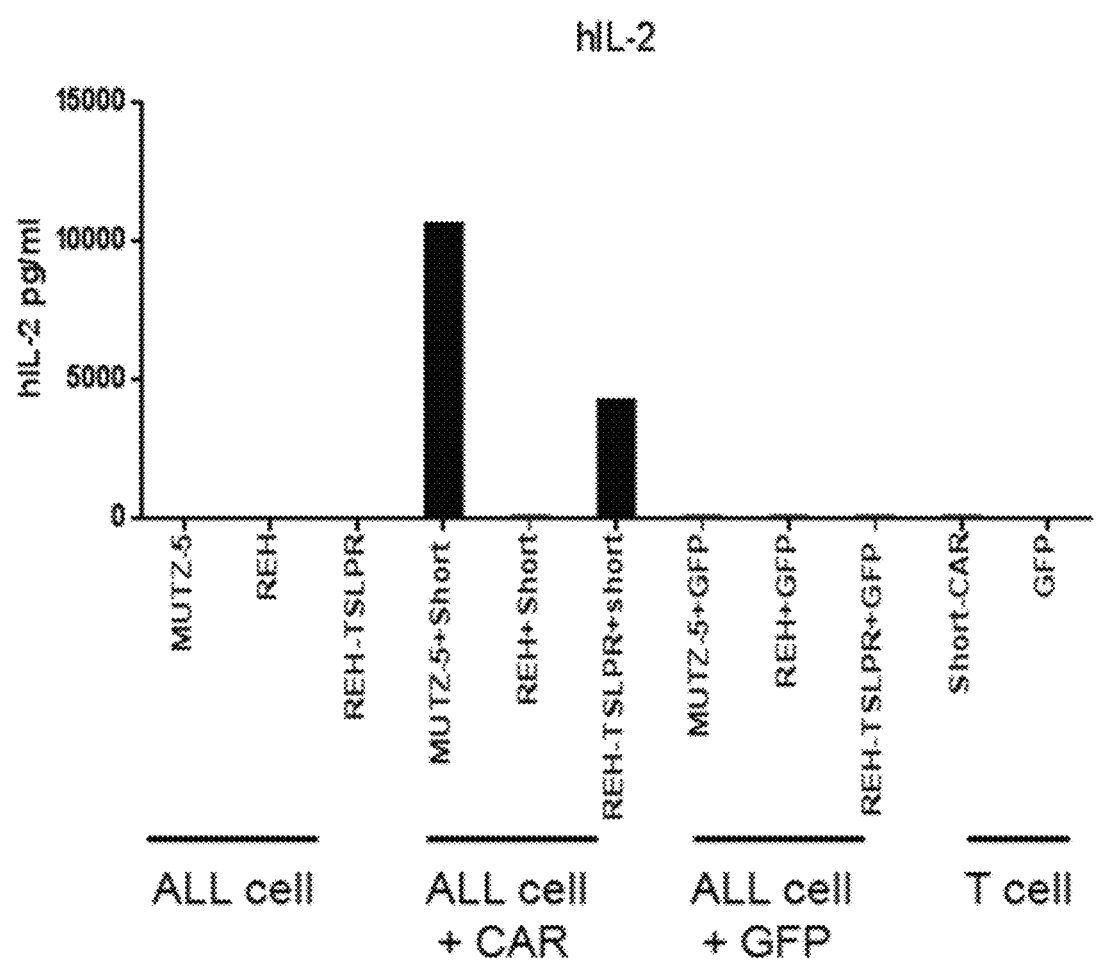

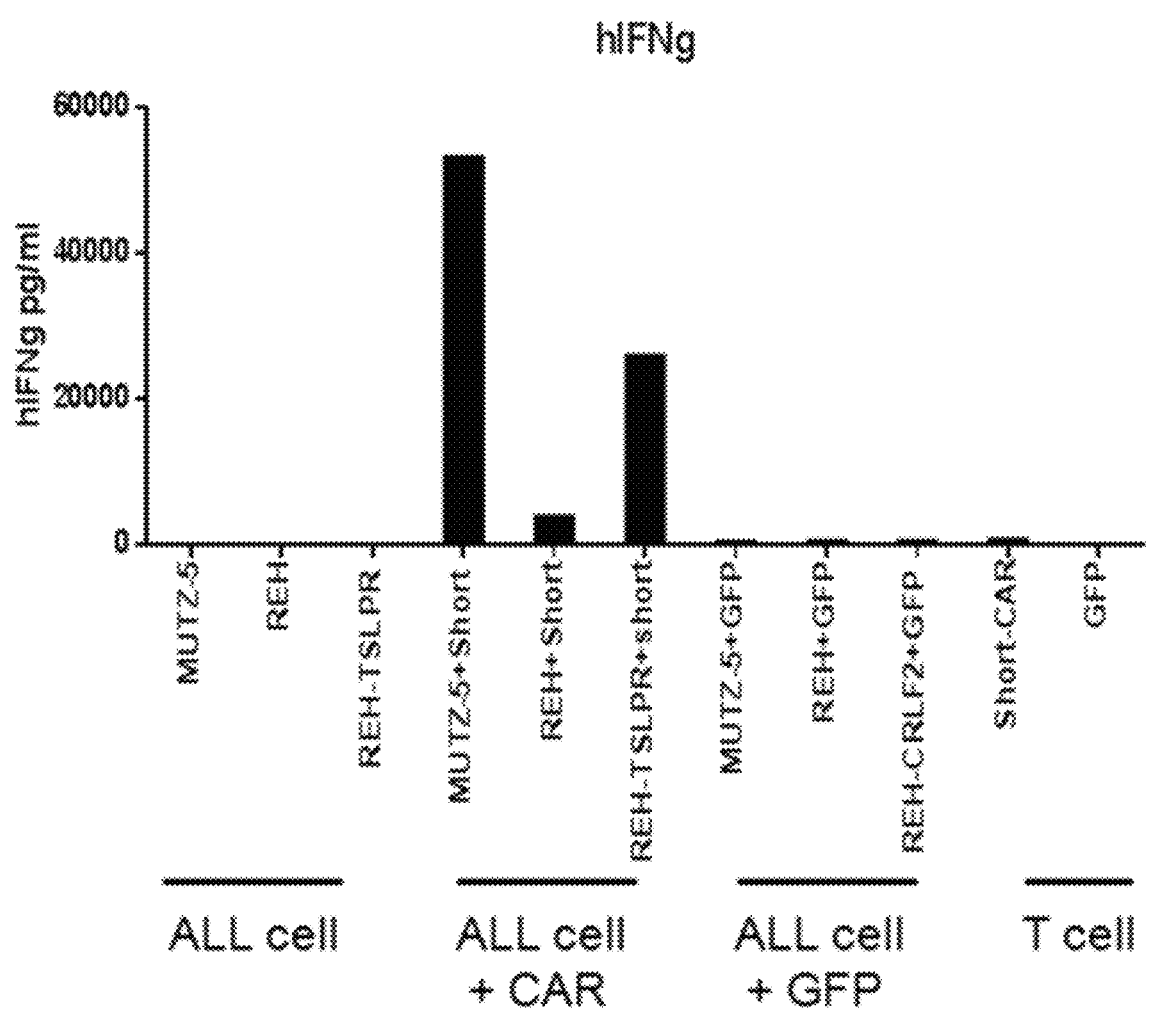

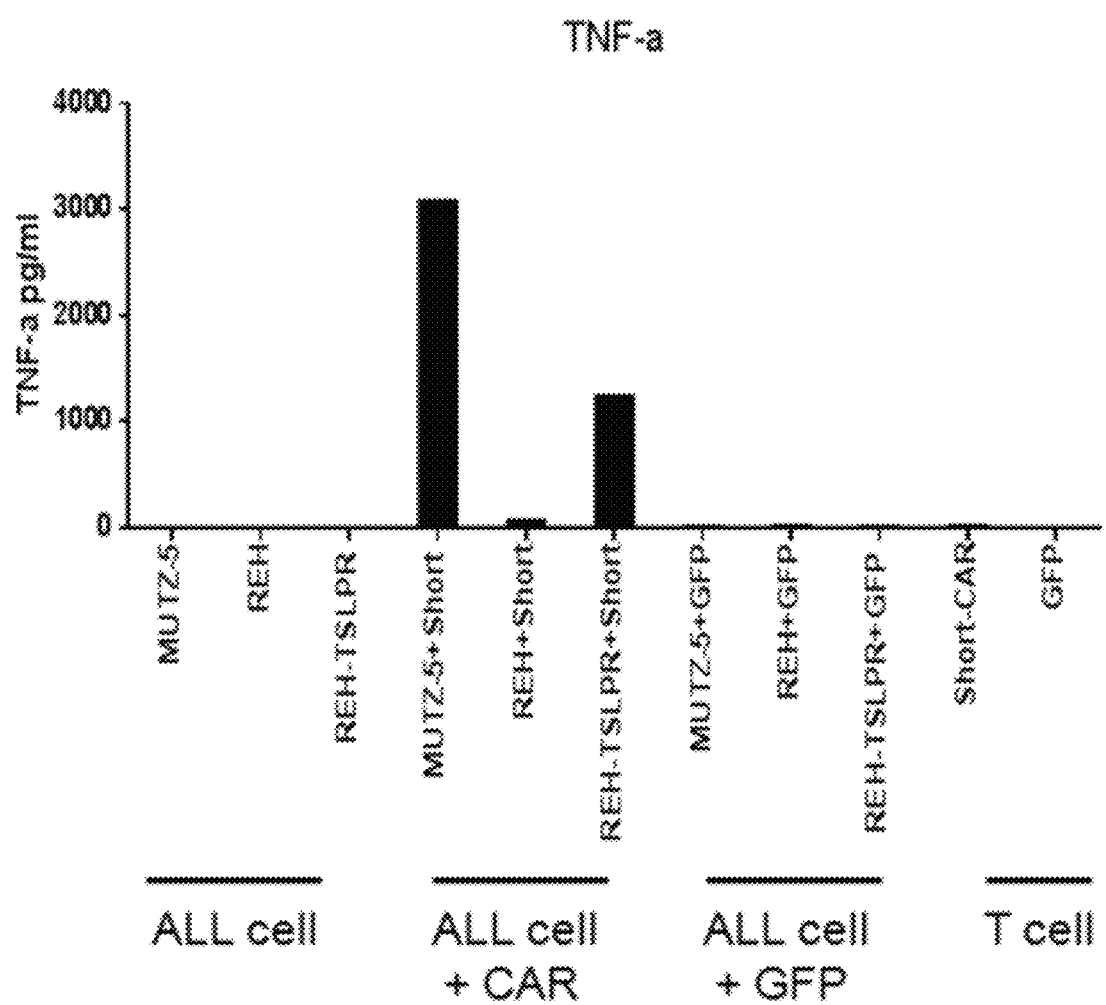

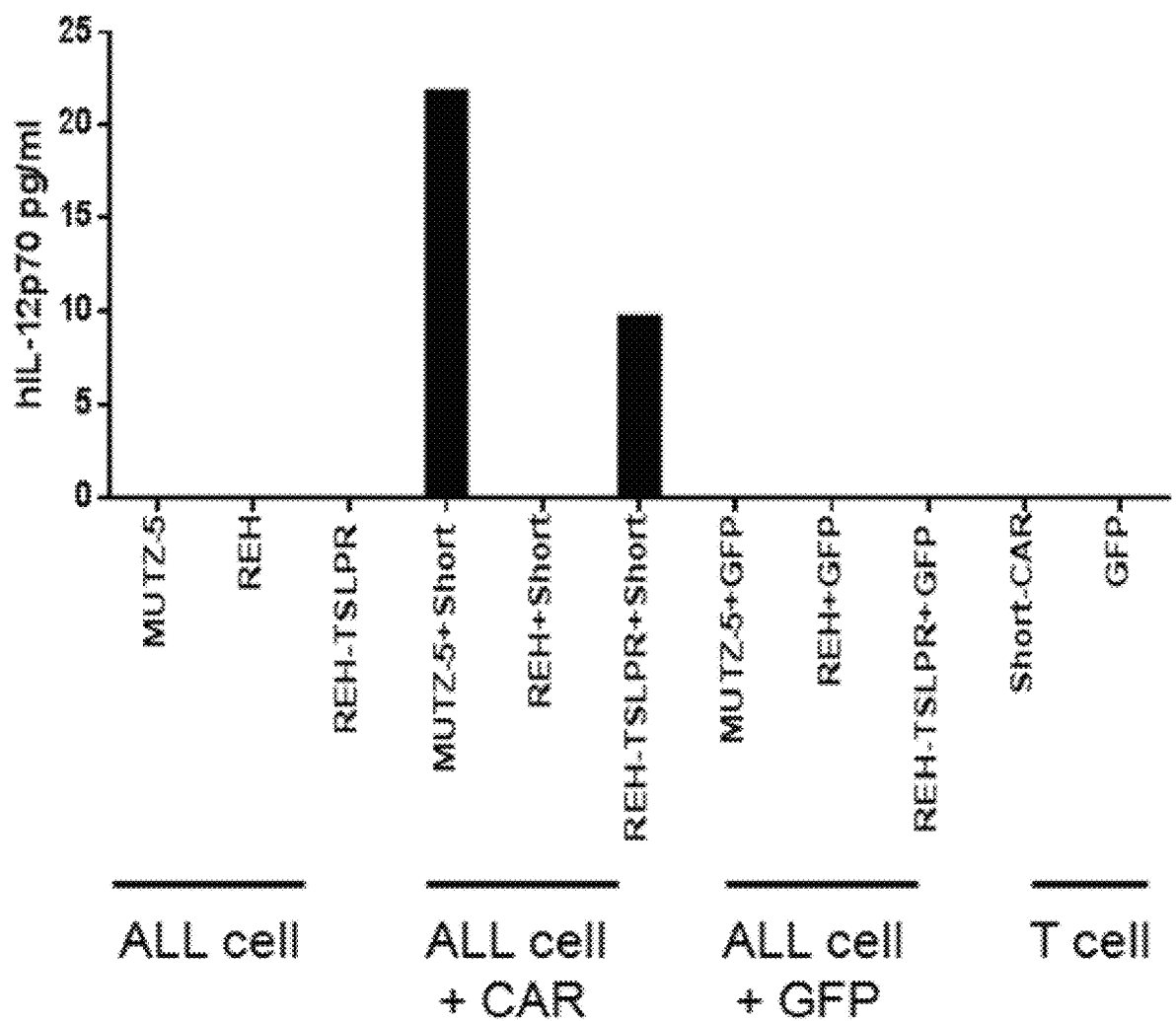

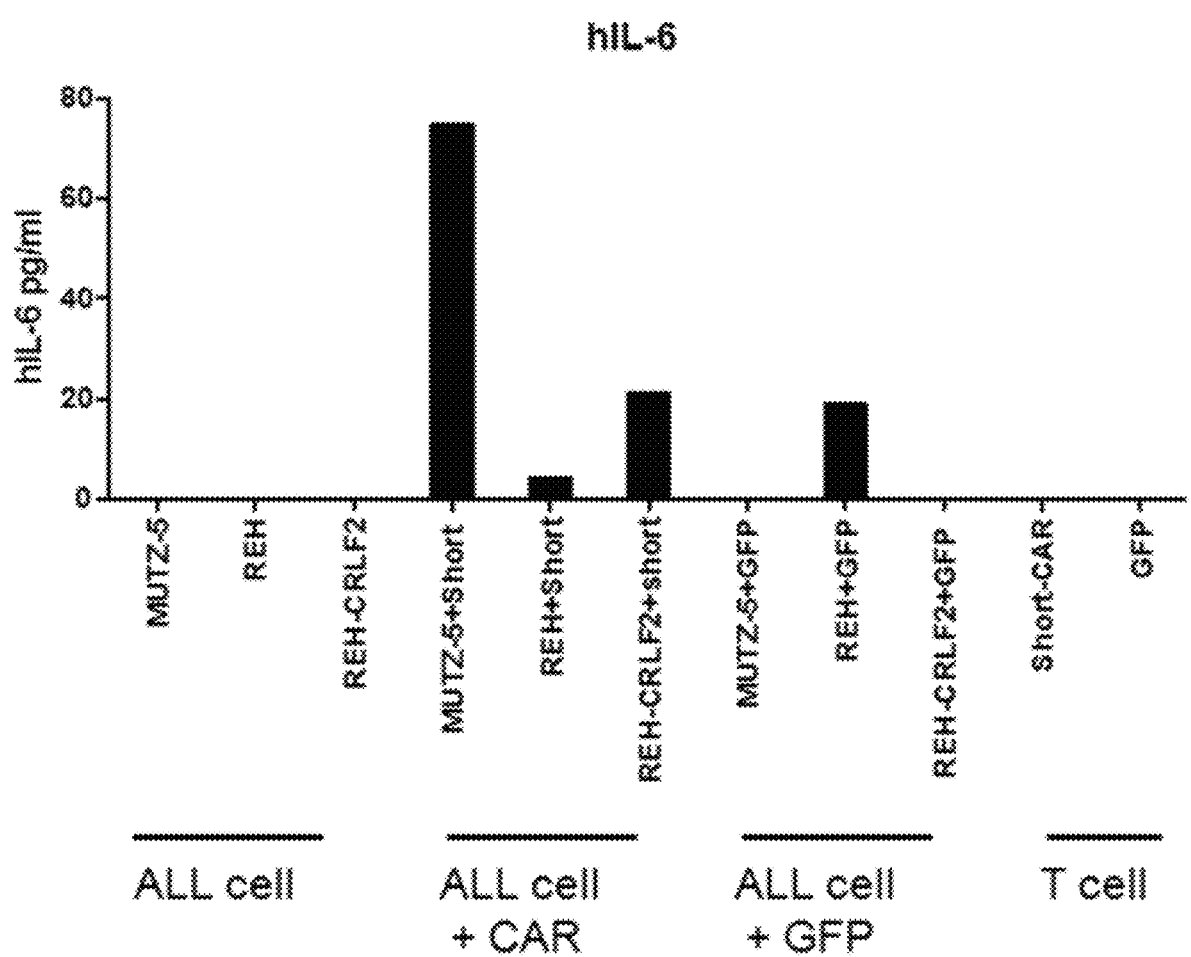

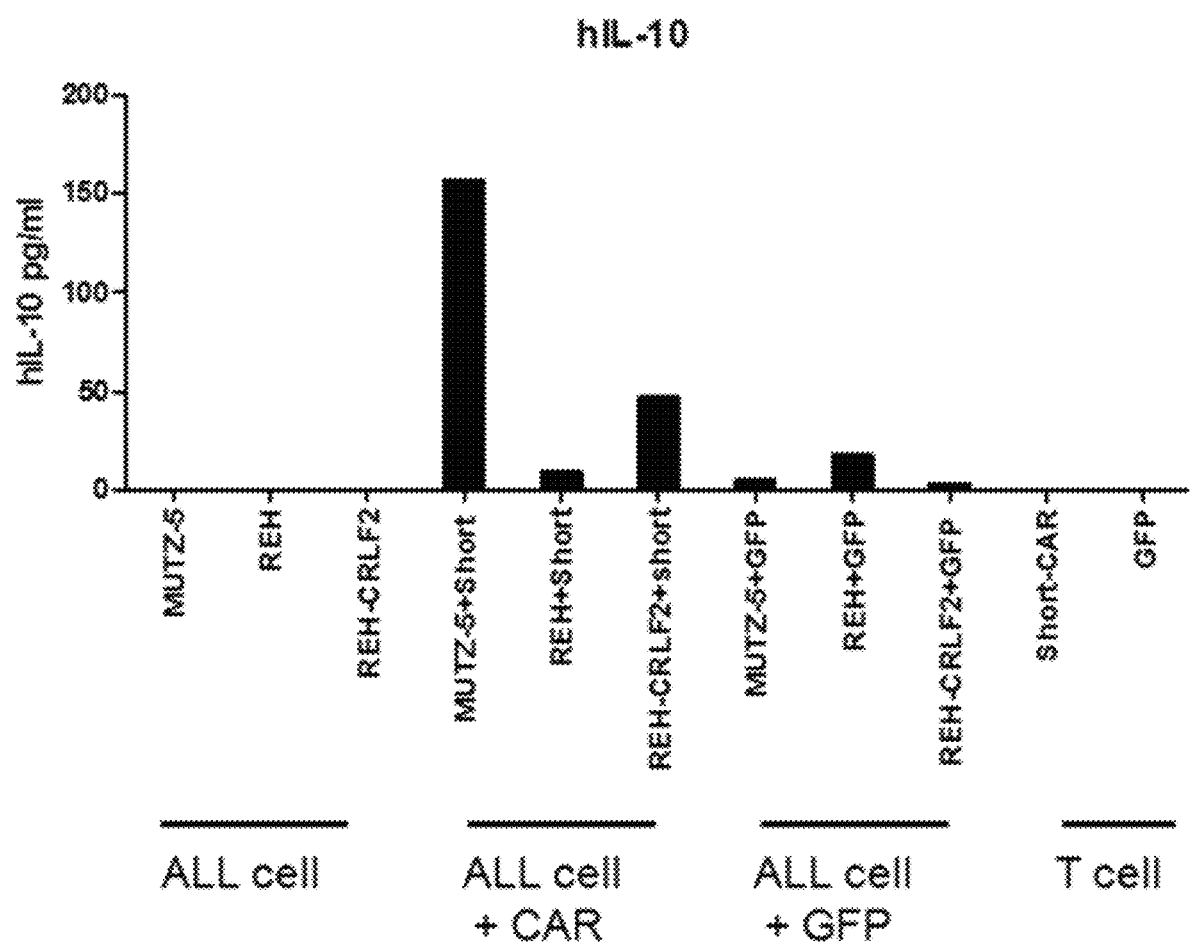

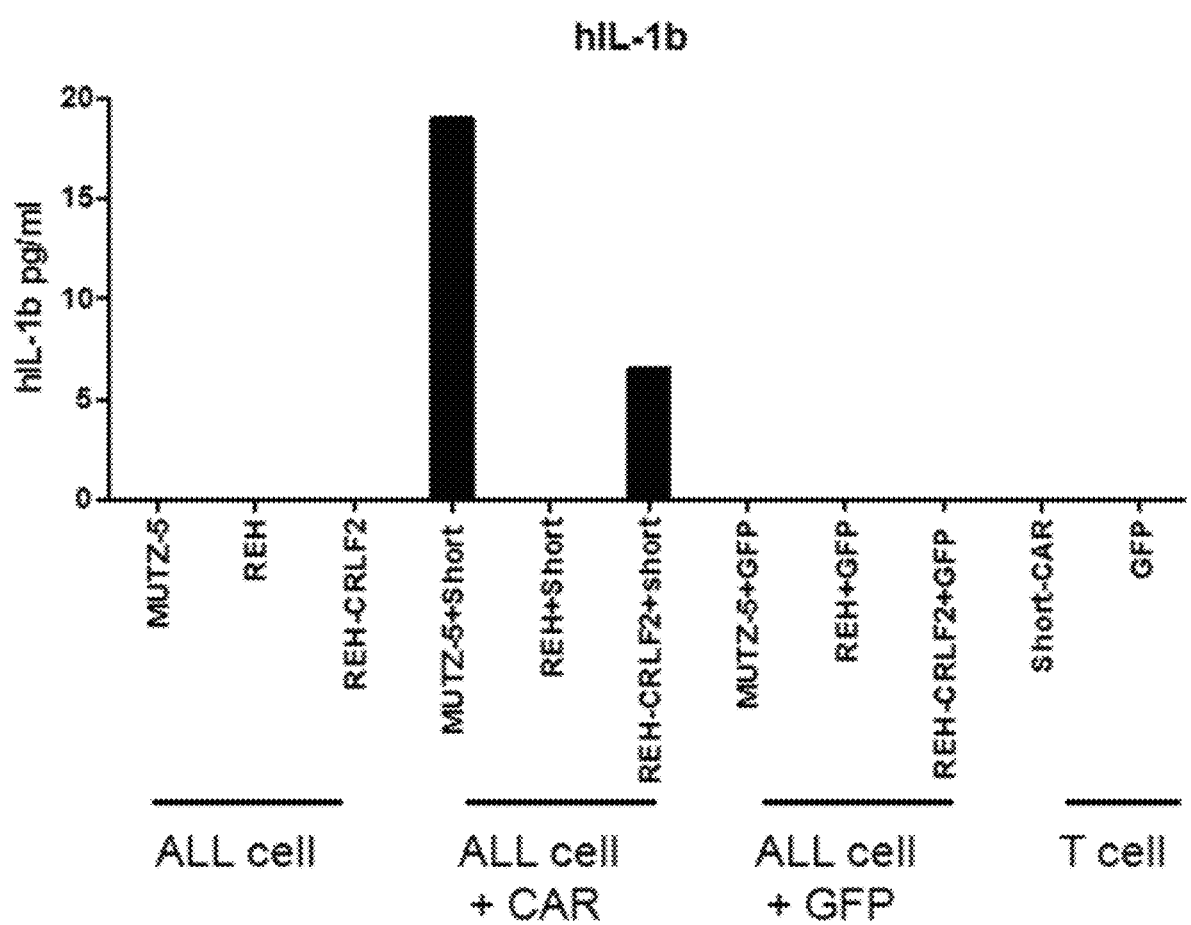

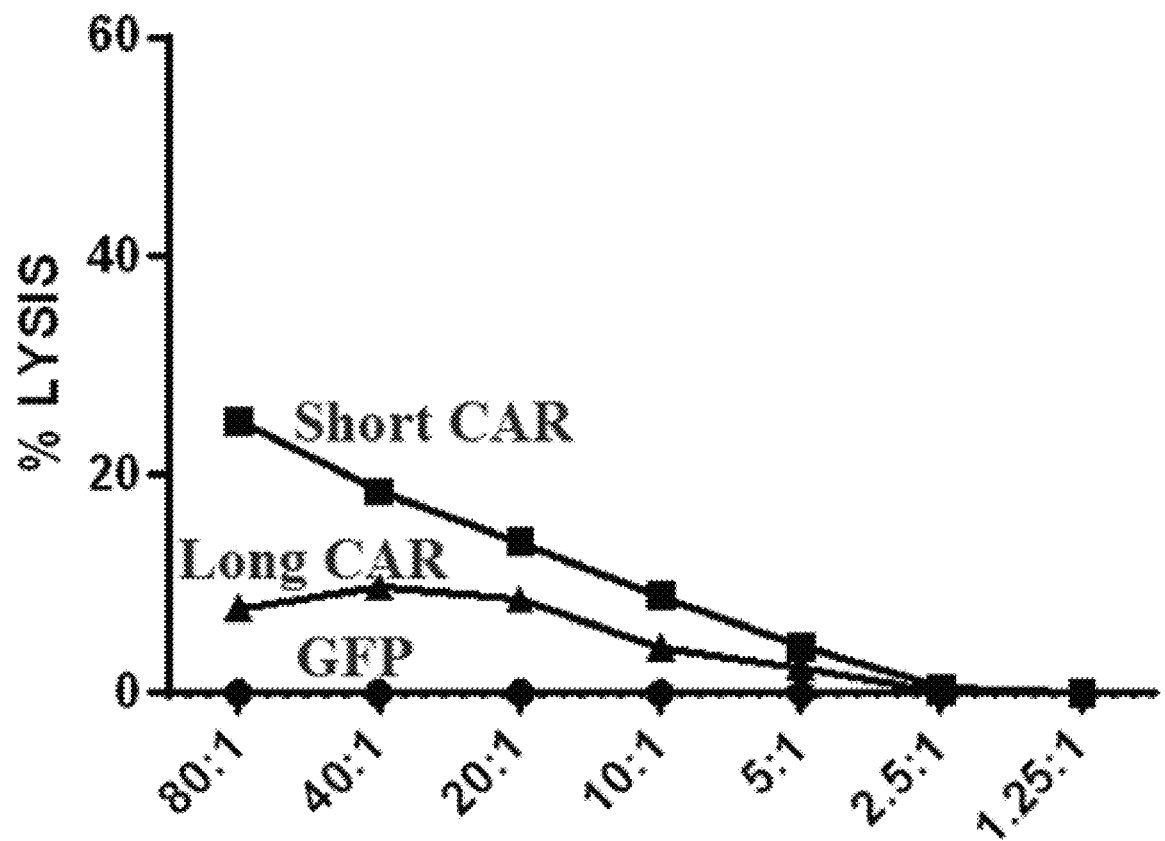

ly overexpressed TSLPR, and cannot
THYMIC STROMAL LYMPHOPOIETIN RECEPTOR-SPECIFIC CHIMERIC ANTIGEN RECEPTORS AND METHODS USING SAME

CROSS-REFERENCE TO RELATED APPLICATIONS

This patent application is a divisional application of U.S. patent application Ser. No. 15/101,583, filed Jun. 3, 2016, which is a U.S. National Phase of International Patent Application No. PCT/US2014/063096, filed Oct. 30, 2014, which claims the benefit of U.S. Provisional Patent Application No. 61/912,948, filed Dec. 6, 2013 and U.S. Provisional Patent Application No. 61/991,697, filed May 12, 2014, each of which is incorporated herein by reference in its entirety.

STATEMENT REGARDING FEDERALLY SPONSORED RESEARCH AND DEVELOPMENT

This invention was made with Government support under project number ZIA BC 011295 by the National Institutes of Health, National Cancer Institute. The Government has certain rights in the invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 58,092 Byte ASCII (Text) file named "749075_ST25.txt," created on Apr. 20, 2020.

BACKGROUND OF THE INVENTION

Cancer is a public health concern. Despite advances in treatments such as chemotherapy, the prognosis for many cancers continues to be poor. Accordingly, there exists an unmet need for additional treatments for cancer.

BRIEF SUMMARY OF THE INVENTION

The invention provides chimeric antigen receptors (CARs) comprising an antigen binding domain specific for thymic stromal lymphopoietin receptor (TSLPR), a transmembrane domain, and an intracellular T cell signaling domain. The CAR may further comprise a 4-1BB intracellular domain, a spacer, or both.

Further embodiments of the invention provide related nucleic acids, recombinant expression vectors, host cells, populations of cells, antibodies, or antigen binding portions thereof, and pharmaceutical compositions relating to the CARs of the invention.

Additional embodiments of the invention provide methods of detecting the presence of a proliferative disorder, e.g., cancer, and methods of treating or preventing a proliferative disorder, e.g., cancer, in a mammal.

BRIEF DESCRIPTION OF THE DRAWINGS

FIGS. 5A and 5B show flow cytometry graphs showing transduction of human T cells using CARs in accordance with certain embodiments of the present invention. FIG. 5A shows detection of CAR using Protein L. FIG. 5B shows detection of CAR using a CD22 protein Fc construct.

FIGS. 7A-7H and 8A-8E are bar graphs showing T cells with TSLPR CAR produce a broad range of inflammatory cytokines in the presence of both TSLPR-transduced and naturally overexpressing ALL cells in accordance with certain embodiments of the present invention.

FIGS. 9A-D are line graphs showing TSLPR CAR mediated tumor cell lysis in accordance with certain embodiments of the present invention.

DETAILED DESCRIPTION OF THE INVENTION

Figure 1:
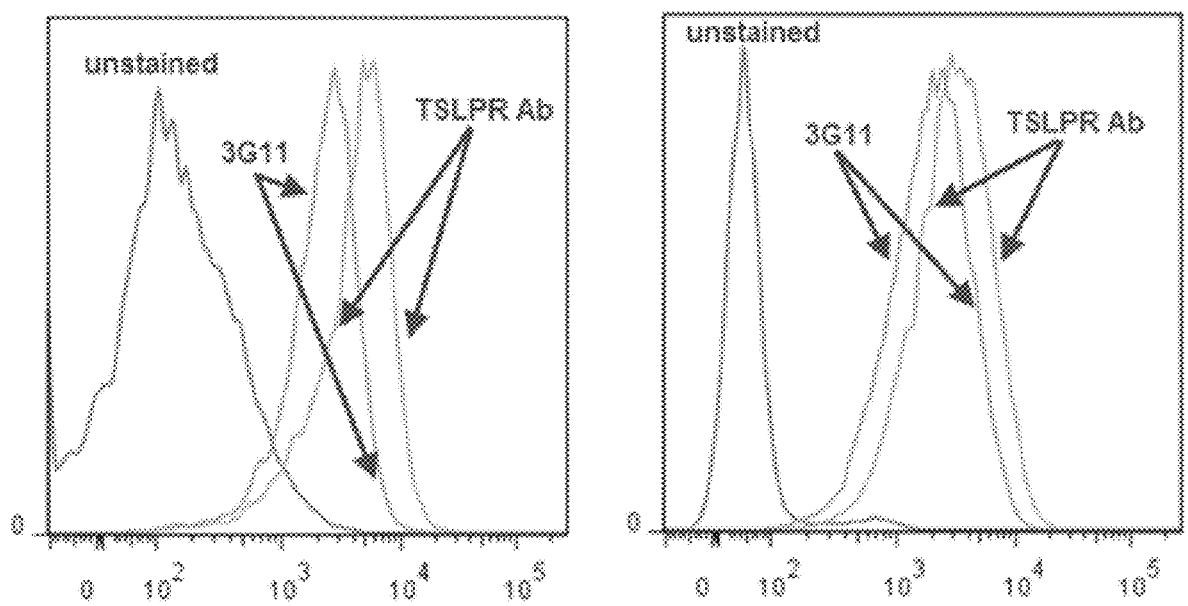
FIG. 1 presents flow cytometry graphs showing the binding of a 3G11 anti-TSLPR antibody and a commercially available anti-TSLPR antibody to precursor-B cell acute lymphoblastic leukemias overexpressing TSLPR. The y-axis is counts, x-axis is mean fluorescence intensity. Binding was detected using phycoerytherin-conjugated goat anti-mouse antibody.

Acute lymphoblastic leukemia (ALL) represents a common oncologic diagnosis in children. Substantial progress has been made in the upfront chemotherapy for pediatric ALL such that most of patients will be cured. Nonetheless, ALL remains a common cause of death from cancer in children due to relapse of disease that no longer responds to cytotoxic chemotherapy or due to refractoriness to upfront treatment. Furthermore, long-term therapy-induced morbidity remains a major issue, particularly in those patients deemed to be high-risk for relapse and thus treated with more intense regimens under current risk-adapted protocols. In adults, ALL occurs less commonly than in children but the prognosis for adult ALL is worse than in children undergoing standard cytotoxic chemotherapy. Treatment of young adults on pediatric-type regimens has improved outcome but not to the level achieved in children.

The adoptive cell transfer (ADT or ACT) of T cells genetically modified to express chimeric antigen receptors (CARs) targeting antigens expressed on lymphoid cells have demonstrated potent activity in B cell malignancies including ALL resulting in remissions in chemotherapy refractory patients. The surface protein being targeted in the majority of these trials is the CD19 antigen that is expressed on both malignant and non-malignant B cells. However, not all patients respond and relapses occur, in some cases due to loss of CD19 expression. Loss of CD19 also has been observed after treatment with bispecific antibody-based reagents targeting CD19 and CD3.

Substantial progress in genomics has resulted in the identification of genes and pathways that are dysregulated in ALL. One such category are those associated with cytokine signaling including IL-7 and, in particular, CD127 (IL-7Ralpha). Thymic stromal lymphopoietin (TSLP) is a cytokine that shares CD127 but utilizes a second receptor chain, TSLPR (gene name CRLF2) as part of the heterodimeric signaling complex. Overexpression of TSLPR has been identified in 5-10% of pediatric and adult ALL, largely due to translocations or deletions resulting in alternative promoters. Overexpression of TSLPR appears to be associated with poor prognosis in both children and adults with ALL, and it appears that activation of the TSLPR pathway as biologically important for ALL blasts. Also, in approximately 50% of cases, increased TSLPR expression is associated with mutations in the IKZF gene, a particularly high risk subgroup of patients. TSLPR seems to have restricted normal tissue expression.

An embodiment of the invention provides chimeric antigen receptors (CARs) comprising an antigen binding domain specific for TSLPR, a transmembrane domain, and an intracellular T cell signaling domain. The CAR may further comprise a 4-1BB intracellular domain, a spacer, or both.

A chimeric antigen receptor (CAR) is an artificially constructed hybrid protein or polypeptide containing the antigen binding domain of an antibody (e.g., single chain variable fragment (scFv)) linked to T-cell signaling domains. Characteristics of CARs include their ability to redirect T-cell specificity and reactivity toward a selected target in a non-MHC-restricted manner, exploiting the antigen-binding properties of monoclonal antibodies. The non-MHC-restricted antigen recognition gives T cells expressing CARs the ability to recognize antigen independent of antigen processing, thus bypassing a major mechanism of tumor escape. Moreover, when expressed in T-cells, CARs advantageously do not dimerize with endogenous T cell receptor (TCR) alpha and beta chains.

The phrases "have antigen specificity" and "elicit antigen-specific response" as used herein means that the CAR can specifically bind to and immunologically recognize an antigen, such that binding of the CAR to the antigen elicits an immune response.

The CARs of the invention have antigen specificity for Thymic Stromal Lymphopoietin Receptor (TSLPR). TSLPR is overexpressed on the surface of approximately 10% of adult and pediatric B cell precursor acute lymphoblastic leukemia (BCP-ALL). The expression of TSLPR by normal, non-tumor, or non-cancerous cells is not as robust as the expression by tumor or cancer cells. In this regard, the tumor or cancer cells can over-express TSLPR or express TSLPR at a significantly higher level, as compared to the expression of TSLPR by normal, non-tumor, or non-cancerous cells.

Without being bound to a particular theory or mechanism, it is believed that by eliciting an antigen-specific response against TSLPR, the inventive CARs provide for one or more of the following: targeting and destroying TSLPR-expressing cancer cells, reducing or eliminating cancer cells, facilitating infiltration of immune cells to tumor site(s), and enhancing/extending anti-cancer responses.

The invention provides a CAR comprising an antigen binding domain specific for TSLPR, based on the antibodies, e.g., 3G11 as described in Lu et al., J. Exp. Med., 2009, 206:2111-9 or 2D10 as described in Rochman et al., J. Immunol., 2007, 178:6720-6724 (each incorporated herein by reference in its entirety). The scFv of these antibodies comprise a light chain variable region and a heavy chain variable region. In embodiments of the invention, the light chain and heavy chain may comprise any suitable combination of light chain and heavy chain sequences, e.g., as listed in Table 1 below.

In an embodiment, the antigen binding domain comprises a linker. The linker connects the heavy chain variable region and the light chain variable region of the antigen binding domain. Any linker suitable for linking the heavy chain variable region and the light chain variable region may be used in the antigen binding domains of the invention. In an embodiment, the linker comprises, consists of, or consists essentially of a glycine-serine linker domain. Preferably, the antigen binding domain comprises a scFv comprising a heavy chain variable region, a light chain variable region, and a linker. In embodiments of the invention, the light chain, heavy chain, and linker may comprise any suitable combination of light chain, heavy chain, and linker sequences as listed in Table 1 below.

In an embodiment of the invention, the antigen binding domain that comprises an scFv comprising, consisting, or consisting essentially of (SEQ ID NO: 1)
QVTLKESGPGILKPSQTLSLTCSFSGFSLSTSGMGVGWIRQPSGKGLEWL

AHIWWDDDKYYNPSLKSQLTISKDTSRNQVFLKITSVDTADTATYYCSRR

PRGTMDAMDYWGQGTSVTVSSGGGGSGGGGSGGGGSDIVMTQAASSLSAS

LGDRVTISCRASQDISKYLNWYQQKPDGTVKLLIYYTSRLHSGVPSRFSG

SGSGTDYSLTIRNLEQEDIATYFCQQVYTLPWTFGGGTKLEIK or (SEQ ID NO: 2)
QVTLKESGPGILKPSQTLSLTCSFSGFSLNTSGMGVGWIRQPSGKGLEWL

AHIWWDDDKYYNPSLKSQLTISKDTSRNQVFLKITSVDTADSATYYCARR

ASHVSTVDSFDFWGQGTTLTVSSGGGGSGGGGSGGGGSDIQMTQTTSSLS

ASLGDRVTISCRASQDISNYLNWFQQKPDGTVKLLIYYTSRLHSGVPSKF

SGSGSGTDYSLTISNLEQEDIATYFCQQGYTLPWTFGGGTKLEIK.

A vector encoding the amino acid sequences described herein may comprise a nucleic acid sequence that would encode AS, AT, or both, such as ASAT (SEQ ID NO: 3) directly before the start codon. These sequences are not translated as part of the CARs.

In an embodiment, the antigen binding domain comprises a leader/signal sequence. The leader sequence may be positioned at the amino terminus of the heavy chain variable region. The leader sequence may comprise any suitable leader sequence. In embodiments of the invention, the leader/signal sequence may comprise the sequence as listed in Table 1 below. In the mature form of the T cell, the leader sequence may not be present.

In an embodiment of the invention, the CAR comprises a transmembrane domain. In an embodiment of the invention, the transmembrane domain comprises CD8. The CD8 can comprise the CD8α (CD8 alpha) hinge and transmembrane domain. In a preferred embodiment, the CD8 is human. The CD8 may comprise less than the whole CD8. In embodiments of the invention, the CD8 may comprise the sequence as listed in Table 1 below.

In an embodiment of the invention, the CAR comprises an intracellular T cell signaling domain comprising 4-1BB (CD137), CD3 zeta (ζ), or both. In a preferred embodiment, the CD3 zeta, 4-1BB, or both is/are human. 4-1BB transmits a potent costimulatory signal to T cells, promoting differentiation and enhancing long-term survival of T lymphocytes. CD3ζ associates with TCRs to produce a signal and contains immunoreceptor tyrosine-based activation motifs (ITAMs). In an embodiment, the CAR lacks a 4-1BB domain. In another embodiment, the CAR comprises a CD28 domain. CD28 is a T cell marker important in T cell co-stimulation. The 4-1BB, CD28, CD3 zeta, or any of these may comprise less than the whole 4-1BB or CD3 zeta, respectively. In embodiments of the invention, the 4-1BB may comprise the sequence as listed in Table 1 below. In embodiments of the invention, the CD3 zeta may comprise the sequence as listed in Table 1 below.

In an embodiment of the invention, the CAR comprises a spacer. The spacer may be between any aforementioned domains. In an embodiment, the CAR comprises an IgG heavy chain constant domain (CH2CH3) spacer. In a further embodiment, the spacer can be between the scFv and the transmembrane domain. In a preferred embodiment, the sequence of the spacer, e.g., CH2CH3, is human. In embodiments of the invention, the spacer may comprise the sequence as listed in Table 1 below.

Embodiments of the invention comprise sequences as provided in Table 1 below.

TABLE 1

| Sequence | SEQ ID NO: | Segment | Notes |
|---|---|---|---|
| M | 4 | | start methionine |
| ALPVTALLLPLALLLHAARP | 5 | | signal peptide |

TABLE 1-continued

| Sequence | SEQ ID NO: | Segment | Notes |
|---|---|---|---|
| QVTLKESGPGILKPSQTLSLTCSFS | 6 | scFv | heavy chain |
| GFSLX$^1$TSGMG | 7: X$^1$ as S<br>8: X$^1$ as N | scFv | heavy chain: CDR1 |
| VGWIRQPSGKGLEWLAH | 9 | scFv | heavy chain |
| IWWDDDK | 10 | scFv | heavy chain: CDR2 |
| YNPSLKSQLTISKDTSRNQVFLKITSVDTADX$^2$ATYYC | 11: X$^2$ as T<br>12: X$^2$ as S | scFv | heavy chain |
| X$^3$RRX$^4$X$^5$X$^6$X$^7$X$^8$TX$^9$DX$^{10}$X$^{11}$DX$^{12}$ | 13: X$^3$ as S; X$^4$ as P; X$^5$ as R; X$^6$ as no aa; X$^7$ as no aa; X$^8$ as G; X$^9$ as M; X$^{10}$ as A; X$^{11}$ as M; X12 as Y<br>14: X$^3$ as A; X$^4$ as A; X$^5$ as S; X$^6$ as H; X$^7$ as V; X$^8$ as S; X$^9$ as V; X$^{10}$ as S; X$^{11}$ as F; X$^{12}$ as F | scFv | heavy chain: J region (CDR3) |
| WGQGTX$^{13}$X$^{14}$TVSS | 15: X$^{13}$ as S; X$^{14}$ as V<br>16: X$^{13}$ as T; X$^{14}$ as L | scFv | heavy chain |
| GGGGSGGGGSGGGGS | 17 | scFv | linker |
| DIX$^{15}$MTQX$^{16}$X$^{17}$SSLSASLGDRVTISCRAS | 18: X$^{15}$ as V; X$^{16}$ as A; X$^{17}$ as A<br>19: X$^{15}$ as Q; X$^{16}$ as T; X$^{17}$ as T | scFv | light chain |
| QDISX$^{18}$Y | 20: X$^{18}$ as K<br>21: X$^{18}$ as N | scFv | light chain: CDR1 |
| LNWX$^{19}$QQKPDGTVKLLIY | 22: X$^{19}$ as Y<br>23: X$^{19}$ as F | scFv | light chain |
| YTS | 24 | scFv | light chain: CDR2 |
| RLHSGVPSX$^{20}$FSGSGSGTDYSLTIX$^{21}$NLEQEDIATYFC | 25: X$^{20}$ as R; X$^{21}$ as R<br>26: X$^{20}$ as K; X$^{21}$ as S | scFv | light chain |
| QQX$^{22}$YTLPWT | 27: X$^{22}$ as V<br>28: X$^{22}$ as G | scFv | light chain: J region (CDR3) |
| FGGGTKLEIK | 29 | scFv | light chain |
| LEDP | 30 | spacer | |
| AEPKSPDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAK | 31 | spacer | CH2 |
| GQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | 32 | spacer | CH3 |
| KDPK | 33 | spacer | |
| SG | 34 | | added amino acids due to vector design at BspEI site of vector |
| TTTPAPRPPTPAPTIASQPLSLRPEACRPAAGGAVHTRGLDFACD | 35 | CD8 | CD8α hinge |

TABLE 1-continued

| Sequence | SEQ ID NO: | Segment | Notes |
|---|---|---|---|
| IYIWAPLAGTCGVLLLSLVITLY C | 36 | CD8 | CD8 transmembrane domain |
| KRGRKKLLYIFKQPFMRPVQTT QEEDGCSCRFPEEEEGGCEL | 37 | 4-1BB | 4-1BB intracellular domain |
| RVKFSRSADAPAYKQGQNQLY NELNLGRREEYDVLDKRRGRD PEMGGKPRRKNPQEGLYNELQ KDKMAEAYSEIGMKGERRRGK GHDGLYQGLSTATKDTYDALH MQALPPR | 38 | CD3ζ | |

Embodiments of the invention include the following sequences in Table 2 that comprise the sequences presented in Table 1 above.

TABLE 2

| Name | Short 3G11 | Long 3G11 | Short 2D10 | Long 2D10 |
|---|---|---|---|---|
| SEQ ID NO: | 39 | 40 | 41 | 42 |
| Comprising | 4 | 4 | 4 | 4 |
| Table 1 | 5 | 5 | 5 | 5 |
| SEQ ID NOS: | 6 | 6 | 6 | 6 |
| | 7 | 7 | 8 | 8 |
| | 9 | 9 | 9 | 9 |
| | 10 | 10 | 10 | 10 |
| | 11 | 11 | 12 | 12 |
| | 13 | 13 | 14 | 14 |
| | 15 | 15 | 16 | 16 |
| | 17 | 17 | 17 | 17 |
| | 18 | 18 | 19 | 19 |
| | 20 | 20 | 21 | 21 |
| | 22 | 22 | 23 | 23 |
| | 24 | 24 | 24 | 24 |
| | 25 | 25 | 26 | 26 |
| | 27 | 27 | 28 | 28 |
| | 29 | 29 | 29 | 29 |
| | | 30 | | 30 |
| | | 31 | | 31 |
| | | 32 | | 32 |
| | | 33 | | 33 |
| | 34 | 34 | 34 | 34 |
| | 35 | 35 | 35 | 35 |
| | 36 | 36 | 36 | 36 |
| | 37 | 37 | 37 | 37 |
| | 38 | 38 | 38 | 38 |

Embodiments of the invention include the following sequences in Table 3 that comprise the sequences presented in Table 1 above, where the signal peptide is not present.

TABLE 3

| Name | Short 3G11 | Long 3G11 | Short 2D10 | Long 2D10 |
|---|---|---|---|---|
| SEQ ID NO: | 43 | 44 | 45 | 46 |
| Comprising | 6 | 6 | 6 | 6 |
| Table 1 | 7 | 7 | 8 | 8 |
| SEQ ID NOS: | 9 | 9 | 9 | 9 |
| | 10 | 10 | 10 | 10 |
| | 11 | 11 | 12 | 12 |
| | 13 | 13 | 14 | 14 |
| | 15 | 15 | 16 | 16 |
| | 17 | 17 | 17 | 17 |
| | 18 | 18 | 19 | 19 |
| | 20 | 20 | 21 | 21 |
| | 22 | 22 | 23 | 23 |
| | 24 | 24 | 24 | 24 |
| | 25 | 25 | 26 | 26 |
| | 27 | 27 | 28 | 28 |
| | 29 | 29 | 29 | 29 |
| | | 30 | | 30 |
| | | 31 | | 31 |
| | | 32 | | 32 |
| | | 33 | | 33 |
| | 34 | 34 | 34 | 34 |
| | 35 | 35 | 35 | 35 |
| | 36 | 36 | 36 | 36 |
| | 37 | 37 | 37 | 37 |
| | 38 | 38 | 38 | 38 |

Included in the scope of the invention are functional portions of the inventive CARs described herein. The term "functional portion" when used in reference to a CAR refers to any part or fragment of the CAR of the invention, which part or fragment retains the biological activity of the CAR of which it is a part (the parent CAR). Functional portions encompass, for example, those parts of a CAR that retain the ability to recognize target cells, or detect, treat, or prevent a disease, to a similar extent, the same extent, or to a higher extent, as the parent CAR. In reference to the parent CAR, the functional portion can comprise, for instance, about 10%, 25%, 30%, 50%, 68%, 80%, 90%, 95%, or more, of the parent CAR.

The functional portion can comprise additional amino acids at the amino or carboxy terminus of the portion, or at both termini, which additional amino acids are not found in the amino acid sequence of the parent CAR. Desirably, the additional amino acids do not interfere with the biological function of the functional portion, e.g., recognize target cells, detect cancer, treat or prevent cancer, etc. More desirably, the additional amino acids enhance the biological activity, as compared to the biological activity of the parent CAR.

Included in the scope of the invention are functional variants of the inventive CARs described herein. The term "functional variant" as used herein refers to a CAR, polypeptide, or protein having substantial or significant sequence identity or similarity to a parent CAR, which functional variant retains the biological activity of the CAR of which it is a variant. Functional variants encompass, for example, those variants of the CAR described herein (the parent CAR) that retain the ability to recognize target cells to a similar extent, the same extent, or to a higher extent, as the parent CAR. In reference to the parent CAR, the functional variant can, for instance, be at least about 30%, 50%, 75%, 80%, 90%, 98% or more identical in amino acid sequence to the parent CAR.

A functional variant can, for example, comprise the amino acid sequence of the parent CAR with at least one conservative amino acid substitution. Alternatively or additionally, the functional variants can comprise the amino acid sequence of the parent CAR with at least one non-conservative amino acid substitution. In this case, it is preferable for the non-conservative amino acid substitution to not interfere with or inhibit the biological activity of the functional variant. The non-conservative amino acid substitution may enhance the biological activity of the functional variant, such that the biological activity of the functional variant is increased as compared to the parent CAR.

Amino acid substitutions of the inventive CARs are preferably conservative amino acid substitutions. Conservative amino acid substitutions are known in the art, and include amino acid substitutions in which one amino acid having certain physical and/or chemical properties is exchanged for another amino acid that has the same or similar chemical or physical properties. For instance, the conservative amino acid substitution can be an acidic/negatively charged polar amino acid substituted for another acidic/negatively charged polar amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Cys, Val, etc.), a basic/positively charged polar amino acid substituted for another basic/positively charged polar amino acid (e.g. Lys, His, Arg, etc.), an uncharged amino acid with a polar side chain substituted for another uncharged amino acid with a polar side chain (e.g., Asn, Gln, Ser, Thr, Tyr, etc.), an amino acid with a beta-branched side-chain substituted for another amino acid with a beta-branched side-chain (e.g., Ile, Thr, and Val), an amino acid with an aromatic side-chain substituted for another amino acid with an aromatic side chain (e.g., His, Phe, Trp, and Tyr), etc.

Also, amino acids may be added or removed from the sequence based on vector design. For example, SEQ ID NO: 34, added amino acids due to vector design at BspEI site of vector, may be removed from the CARs as described herein, e.g., removed from the sequences in Table 2, Table 3, or both.

The CAR can consist essentially of the specified amino acid sequence or sequences described herein, such that other components, e.g., other amino acids, do not materially change the biological activity of the functional variant.

The CARs of embodiments of the invention (including functional portions and functional variants) can be of any length, i.e., can comprise any number of amino acids, provided that the CARs (or functional portions or functional variants thereof) retain their biological activity, e.g., the ability to specifically bind to antigen, detect diseased cells in a mammal, or treat or prevent disease in a mammal, etc. For example, the CAR can be about 50 to about 5000 amino acids long, such as 50, 70, 75, 100, 125, 150, 175, 200, 300, 400, 500, 600, 700, 800, 900, 1000 or more amino acids in length.

The CARs of embodiments of the invention (including functional portions and functional variants of the invention) can comprise synthetic amino acids in place of one or more naturally-occurring amino acids. Such synthetic amino acids are known in the art, and include, for example, aminocyclohexane carboxylic acid, norleucine, α-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, α-(2-amino-2-norbornane)-carboxylic acid, α,γ-diaminobutyric acid, α,β-diaminopropionic acid, homophenylalanine, and α-tert-butylglycine.

The CARs of embodiments of the invention (including functional portions and functional variants) can be glycosylated, amidated, carboxylated, phosphorylated, esterified, N-acylated, cyclized via, e.g., a disulfide bridge, or converted into an acid addition salt and/or optionally dimerized or polymerized, or conjugated.

The CARs of embodiments of the invention (including functional portions and functional variants thereof) can be obtained by methods known in the art. The CARs may be made by any suitable method of making polypeptides or proteins. Suitable methods of de novo synthesizing polypeptides and proteins are described in references, such as Chan et al., *Fmoc Solid Phase Peptide Synthesis*, Oxford University Press, Oxford, United Kingdom, 2000; *Peptide and Protein Drug Analysis*, ed. Reid, R., Marcel Dekker, Inc., 2000; *Epitope Mapping*, ed. Westwood et al., Oxford University Press, Oxford, United Kingdom, 2001; and U.S. Pat. No. 5,449,752. Also, polypeptides and proteins can be recombinantly produced using the nucleic acids described herein using standard recombinant methods. See, for instance, Sambrook et al., *Molecular Cloning: A Laboratory Manual*, 3$^{rd}$ ed., Cold Spring Harbor Press, Cold Spring Harbor, NY 2001; and Ausubel et al., *Current Protocols in Molecular Biology*, Greene Publishing Associates and John Wiley & Sons, NY, 1994. Further, some of the CARs of the invention (including functional portions and functional variants thereof) can be isolated and/or purified from a source, such as a plant, a bacterium, an insect, a mammal, e.g., a rat, a human, etc. Methods of isolation and purification are well-known in the art. Alternatively, the CARs described herein (including functional portions and functional variants thereof) can be commercially synthesized by companies. In this respect, the inventive CARs can be synthetic, recombinant, isolated, and/or purified.

An embodiment of the invention further provides an antibody, or antigen binding portion thereof, which specifically binds to an epitope of the CARs of the invention. The antibody can be any type of immunoglobulin that is known in the art. For instance, the antibody can be of any isotype, e.g., IgA, IgD, IgE, IgG, IgM, etc. The antibody can be monoclonal or polyclonal. The antibody can be a naturally-occurring antibody, e.g., an antibody isolated and/or purified from a mammal, e.g., mouse, rabbit, goat, horse, chicken, hamster, human, etc. Alternatively, the antibody can be a genetically-engineered antibody, e.g., a humanized antibody or a chimeric antibody. The antibody can be in monomeric or polymeric form. Also, the antibody can have any level of affinity or avidity for the functional portion of the inventive CAR.

Methods of testing antibodies for the ability to bind to any functional portion of the inventive CAR are known in the art and include any antibody-antigen binding assay, such as, for example, radioimmunoassay (RIA), ELISA, Western blot, immunoprecipitation, and competitive inhibition assays (see, e.g., Janeway et al., infra, U.S. Patent Application Publication No. 2002/0197266 A1, and U.S. Pat. No. 7,338, 929).

Suitable methods of making antibodies are known in the art. For instance, standard hybridoma methods are described in, e.g., Kohler and Milstein, *Eur. J. Immunol.*, 5, 511-519 (1976), Harlow and Lane (eds.), *Antibodies: A Laboratory Manual*, CSH Press (1988), and C. A. Janeway et al. (eds.), *Immunobiology*, 5$^{th}$ Ed., Garland Publishing, New York, NY (2001)). Alternatively, other methods, such as EBV-hybridoma methods (Haskard and Archer, *J. Immunol. Methods*, 74(2), 361-67 (1984), and Roder et al., *Methods Enzymol.*, 121, 140-67 (1986)), and bacteriophage vector expression systems (see, e.g., Huse et al., *Science*, 246, 1275-81 (1989)) are known in the art. Further, methods of producing antibodies in non-human animals are described in, e.g., U.S. Pat. Nos. 5,545,806, 5,569,825, and 5,714,352, U.S. Patent Application Publication No. 2002/0197266 A1, and U.S. Pat. No. 7,338,929).

Phage display furthermore can be used to generate an antibody. In this regard, phage libraries encoding antigen-binding variable (V) domains of antibodies can be generated using standard molecular biology and recombinant DNA techniques (see, e.g., Sambrook et al., supra, and Ausubel et al., supra). Phage encoding a variable region with the desired specificity are selected for specific binding to the desired antigen, and a complete or partial antibody is reconstituted comprising the selected variable domain. Nucleic acid sequences encoding the reconstituted antibody are introduced into a suitable cell line, such as a myeloma cell used for hybridoma production, such that antibodies having the characteristics of monoclonal antibodies are secreted by the cell (see, e.g., Janeway et al., supra, Huse et al., supra, and U.S. Pat. No. 6,265,150).

Antibodies can be produced by transgenic mice that are transgenic for specific heavy and light chain immunoglobulin genes. Such methods are known in the art and described in, for example U.S. Pat. Nos. 5,545,806 and 5,569,825, and Janeway et al., supra.

Methods for generating humanized antibodies are well known in the art and are described in detail in, for example, Janeway et al., supra, U.S. Pat. Nos. 5,225,539, 5,585,089 and 5,693,761, European Patent No. 0239400 B1, and United Kingdom Patent No. 2188638. Humanized antibodies can also be generated using the antibody resurfacing technology described in U.S. Pat. No. 5,639,641 and Pedersen et al., *J. Mol. Biol.*, 235, 959-973 (1994).

An embodiment of the invention also provides antigen binding portions of any of the antibodies described herein. The antigen binding portion can be any portion that has at least one antigen binding site, such as Fab, F(ab')$_2$, dsFv, sFv, diabodies, and triabodies.

A single-chain variable region fragment (sFv) antibody fragment can be generated using routine recombinant DNA technology techniques (see, e.g., Janeway et al., supra). Similarly, disulfide-stabilized variable region fragments (dsFv) can be prepared by recombinant DNA technology (see, e.g., Reiter et al., *Protein Engineering*, 7, 697-704 (1994)). Antibody fragments of the invention, however, are not limited to these exemplary types of antibody fragments.

Also, the antibody, or antigen binding portion thereof, can be modified to comprise a detectable label, such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

Further provided by an embodiment of the invention is a nucleic acid comprising a nucleotide sequence encoding any of the CARs described herein (including functional portions and functional variants thereof). The nucleic acids of the invention may comprise a nucleotide sequence encoding any of the leader sequences, antigen binding domains, transmembrane domains, and/or intracellular T cell signaling domains described herein.

In some embodiments, the nucleotide sequence may be codon-optimized. Without being bound to a particular theory, it is believed that codon optimization of the nucleotide sequence increases the translation efficiency of the mRNA transcripts. Codon optimization of the nucleotide sequence may involve substituting a native codon for another codon that encodes the same amino acid, but can be translated by tRNA that is more readily available within a cell, thus increasing translation efficiency. Optimization of the nucleotide sequence may also reduce secondary mRNA structures that would interfere with translation, thus increasing translation efficiency.

In an embodiment of the invention, the nucleic acid may comprise a codon-optimized nucleotide sequence that encodes the antigen binding domain of the inventive CAR. In another embodiment of the invention, the nucleic acid may comprise a codon-optimized nucleotide sequence that encodes any of the CARs described herein (including functional portions and functional variants thereof).

"Nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. In some embodiments, the nucleic acid does not comprise any insertions, deletions, inversions, and/or substitutions. However, it may be suitable in some instances, as discussed herein, for the nucleic acid to comprise one or more insertions, deletions, inversions, and/or substitutions.

The nucleic acids of an embodiment of the invention may be recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication.

A recombinant nucleic acid may be one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques, such as those described in Sambrook et al., supra. The nucleic acids can be constructed based on chemical synthesis and/or enzymatic ligation reactions using procedures known in the art. See, for example, Sambrook et al., supra, and Ausubel et al., supra. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, $N^6$-isopentenyladenine, 1-methylguanine, 1-methylinosine, 2,2-dimethylguanine, 2-methyladenine, 2-methylguanine, 3-methylcytosine, 5-methylcytosine, $N^6$-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-$N^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the invention can be purchased from companies, such as Integrated DNA Technologies (Coralville, IA, USA).

The nucleic acid can comprise any isolated or purified nucleotide sequence which encodes any of the CARs or functional portions or functional variants thereof. Alternatively, the nucleotide sequence can comprise a nucleotide sequence which is degenerate to any of the sequences or a combination of degenerate sequences.

An embodiment of the invention also provides an isolated or purified nucleic acid comprising a nucleotide sequence which is complementary to the nucleotide sequence of any of the nucleic acids described herein or a nucleotide sequence which hybridizes under stringent conditions to the nucleotide sequence of any of the nucleic acids described herein.

The nucleotide sequence which hybridizes under stringent conditions may hybridize under high stringency conditions. By "high stringency conditions" is meant that the nucleotide sequence specifically hybridizes to a target sequence (the nucleotide sequence of any of the nucleic acids described herein) in an amount that is detectably stronger than non-specific hybridization. High stringency conditions include conditions which would distinguish a polynucleotide with an exact complementary sequence, or one containing only a few scattered mismatches from a random sequence that happened to have a few small regions (e.g., 3-10 bases) that matched the nucleotide sequence. Such small regions of complementarity are more easily melted than a full-length complement of 14-17 or more bases, and high stringency hybridization makes them easily distinguishable. Relatively high stringency conditions would include, for example, low salt and/or high temperature conditions, such as provided by about 0.02-0.1 M NaCl or the equivalent, at temperatures of about 50-70° C. Such high stringency conditions tolerate little, if any, mismatch between the nucleotide sequence and the template or target strand, and are particularly suitable for detecting expression of any of the inventive CARs. It is generally appreciated that conditions can be rendered more stringent by the addition of increasing amounts of formamide.

The invention also provides a nucleic acid comprising a nucleotide sequence that is at least about 70% or more, e.g., about 80%, about 90%, about 91%, about 92%, about 93%, about 94%, about 95%, about 96%, about 97%, about 98%, or about 99% identical to any of the nucleic acids described herein.

In an embodiment, the nucleic acids of the invention can be incorporated into a recombinant expression vector. In this regard, an embodiment of the invention provides recombinant expression vectors comprising any of the nucleic acids of the invention. For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors of the invention are not naturally-occurring as a whole. However, parts of the vectors can be naturally-occurring. The inventive recombinant expression vectors can comprise any type of nucleotides, including, but not limited to DNA and RNA, which can be single-stranded or double-stranded, synthesized or obtained in part from natural sources, and which can contain natural, non-natural or altered nucleotides. The recombinant expression vectors can comprise naturally-occurring or non-naturally-occurring internucleotide linkages, or both types of linkages. Preferably, the non-naturally occurring or altered nucleotides or internucleotide linkages do not hinder the transcription or replication of the vector.

In an embodiment, the recombinant expression vector of the invention can be any suitable recombinant expression vector, and can be used to transform or transfect any suitable host cell. Suitable vectors include those designed for propagation and expansion or for expression or both, such as plasmids and viruses. The vector can be selected from the group consisting of the pUC series (Fermentas Life Sciences, Glen Burnie, MD), the pBluescript series (Stratagene, LaJolla, CA), the pET series (Novagen, Madison, WI), the pGEX series (Pharmacia Biotech, Uppsala, Sweden), and the pEX series (Clontech, Palo Alto, CA). Bacteriophage vectors, such as λGT10, λGT11, λZapII (Stratagene), λEMBL4, and λNM1149, also can be used. Examples of plant expression vectors include pBI01, pBI101.2, pBI101.3, pBI121 and pBIN19 (Clontech). Examples of animal expression vectors include pEUK-Cl, pMAM, and pMAMneo (Clontech). The recombinant expression vector may be a viral vector, e.g., a retroviral vector or a lentiviral vector.

A number of transfection techniques are generally known in the art (see, e.g., Graham et al., *Virology*, 52: 456-467 (1973); Sambrook et al., supra; Davis et al., *Basic Methods in Molecular Biology*, Elsevier (1986); and Chu et al., *Gene*, 13: 97 (1981). Transfection methods include calcium phosphate co-precipitation (see, e.g., Graham et al., supra), direct micro injection into cultured cells (see, e.g., Capecchi, *Cell*, 22: 479-488 (1980)), electroporation (see, e.g., Shigekawa et al., *BioTechniques*, 6: 742-751 (1988)), liposome mediated gene transfer (see, e.g., Mannino et al., *BioTechniques*, 6: 682-690 (1988)), lipid mediated transduction (see, e.g., Felgner et al., *Proc. Natl. Acad. Sci. USA*, 84: 7413-7417 (1987)), and nucleic acid delivery using high velocity microprojectiles (see, e.g., Klein et al., *Nature*, 327: 70-73 (1987)).

In an embodiment, the recombinant expression vectors of the invention can be prepared using standard recombinant DNA techniques described in, for example, Sambrook et al., supra, and Ausubel et al., supra. Constructs of expression vectors, which are circular or linear, can be prepared to contain a replication system functional in a prokaryotic or eukaryotic host cell. Replication systems can be derived, e.g., from ColEl, 2µ plasmid, λ, SV40, bovine papilloma virus, and the like.

The recombinant expression vector may comprise regulatory sequences, such as transcription and translation initiation and termination codons, which are specific to the type of host cell (e.g., bacterium, fungus, plant, or animal) into which the vector is to be introduced, as appropriate, and taking into consideration whether the vector is DNA- or RNA-based. The recombinant expression vector may comprise restriction sites to facilitate cloning.

The recombinant expression vector can include one or more marker genes, which allow for selection of transformed or transfected host cells. Marker genes include biocide resistance, e.g., resistance to antibiotics, heavy metals, etc., complementation in an auxotrophic host to provide prototrophy, and the like. Suitable marker genes for the inventive expression vectors include, for instance, neomycin/G418 resistance genes, hygromycin resistance genes, histidinol resistance genes, tetracycline resistance genes, and ampicillin resistance genes.

The recombinant expression vector can comprise a native or nonnative promoter operably linked to the nucleotide sequence encoding the CAR (including functional portions and functional variants thereof), or to the nucleotide sequence which is complementary to or which hybridizes to the nucleotide sequence encoding the CAR. The selection of promoters, e.g., strong, weak, inducible, tissue-specific and developmental-specific, is within the ordinary skill of the artisan. Similarly, the combining of a nucleotide sequence with a promoter is also within the skill of the artisan. The promoter can be a non-viral promoter or a viral promoter, e.g., a cytomegalovirus (CMV) promoter, an SV40 promoter, an RSV promoter, or a promoter found in the long-terminal repeat of the murine stem cell virus.

The inventive recombinant expression vectors can be designed for either transient expression, for stable expression, or for both. Also, the recombinant expression vectors can be made for constitutive expression or for inducible expression.

Further, the recombinant expression vectors can be made to include a suicide gene. As used herein, the term "suicide gene" refers to a gene that causes the cell expressing the suicide gene to die. The suicide gene can be a gene that confers sensitivity to an agent, e.g., a drug, upon the cell in which the gene is expressed, and causes the cell to die when the cell is contacted with or exposed to the agent. Suicide genes are known in the art (see, for example, *Suicide Gene Therapy: Methods and Reviews*, Springer, Caroline J. (Cancer Research UK Centre for Cancer Therapeutics at the Institute of Cancer Research, Sutton, Surrey, UK), Humana Press, 2004) and include, for example, the Herpes Simplex Virus (HSV) thymidine kinase (TK) gene, cytosine daminase, purine nucleoside phosphorylase, and nitroreductase.

Included in the scope of the invention are conjugates, e.g., bioconjugates, comprising any of the inventive CARs (including any of the functional portions or variants thereof), nucleic acids, recombinant expression vectors, host cells, populations of host cells, or antibodies, or antigen binding portions thereof. Conjugates, as well as methods of synthesizing conjugates in general, are known in the art (See, for instance, Hudecz, F., *Methods Mol. Biol.* 298: 209-223 (2005) and Kirin et al., *Inorg Chem.* 44(15): 5405-5415 (2005)).

An embodiment of the invention further provides a host cell comprising any of the recombinant expression vectors described herein. As used herein, the term "host cell" refers to any type of cell that can contain the inventive recombinant expression vector. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. Suitable host cells are known in the art and include, for instance, DH5α *E. coli* cells, Chinese hamster ovarian cells, monkey VERO cells, COS cells, HEK293 cells, and the like. For purposes of amplifying or replicating the recombinant expression vector, the host cell may be a prokaryotic cell, e.g., a DH5α cell. For purposes of producing a recombinant CAR, the host cell may be a mammalian cell. The host cell may be a human cell. While the host cell can be of any cell type, can originate from any type of tissue, and can be of any developmental stage, the host cell may be a peripheral blood lymphocyte (PBL) or a peripheral blood mononuclear cell (PBMC). The host cell may be a T cell.

For purposes herein, the T cell can be any T cell, such as a cultured T cell, e.g., a primary T cell, or a T cell from a cultured T cell line, e.g., Jurkat, SupT1, etc., or a T cell obtained from a mammal. If obtained from a mammal, the T cell can be obtained from numerous sources, including but not limited to blood, bone marrow, lymph node, the thymus, or other tissues or fluids. T cells can also be enriched for or purified. The T cell may be a human T cell. The T cell may be a T cell isolated from a human. The T cell can be any type of T cell and can be of any developmental stage, including but not limited to, $CD4^+/CD8^+$ double positive T cells, $CD4^+$ helper T cells, e.g., $Th_1$ and $Th_2$ cells, $CD8^+$ T cells (e.g., cytotoxic T cells), tumor infiltrating cells, memory T cells, naïve T cells, and the like. The T cell may be a $CD8^+$ T cell or a $CD4^+$ T cell.

In an embodiment, the CARs as described herein can be used in suitable non-T cells. Such cells are those with an immune-effector function, such as, for example, NK cells, and T-like cells generated from pluripotent stem cells.

Also provided by an embodiment of the invention is a population of cells comprising at least one host cell described herein. The population of cells can be a heterogeneous population comprising the host cell comprising any of the recombinant expression vectors described, in addition to at least one other cell, e.g., a host cell (e.g., a T cell), which does not comprise any of the recombinant expression vectors, or a cell other than a T cell, e.g., a B cell, a macrophage, a neutrophil, an erythrocyte, a hepatocyte, an endothelial cell, an epithelial cell, a muscle cell, a brain cell, etc. Alternatively, the population of cells can be a substantially homogeneous population, in which the population comprises mainly host cells (e.g., consisting essentially of) comprising the recombinant expression vector. The population also can be a clonal population of cells, in which all cells of the population are clones of a single host cell comprising a recombinant expression vector, such that all cells of the population comprise the recombinant expression vector. In one embodiment of the invention, the population of cells is a clonal population comprising host cells comprising a recombinant expression vector as described herein.

CARs (including functional portions and variants thereof), nucleic acids, recombinant expression vectors, host cells (including populations thereof), and antibodies (including antigen binding portions thereof), all of which are collectively referred to as "inventive CAR materials" hereinafter, can be isolated and/or purified. The term "isolated" as used herein means having been removed from its natural environment. The term "purified" or "isolated" does not require absolute purity or isolation; rather, it is intended as a relative term. Thus, for example, a purified (or isolated) host cell preparation is one in which the host cell is more pure than cells in their natural environment within the body. Such host cells may be produced, for example, by standard purification techniques. In some embodiments, a preparation of a host cell is purified such that the host cell represents at least about 50%, for example at least about 70%, of the total cell content of the preparation. For example, the purity can be at least about 50%, can be greater than about 60%, about 70% or about 80%, or can be about 100%.

The inventive CAR materials can be formulated into a composition, such as a pharmaceutical composition. In this regard, an embodiment of the invention provides a pharmaceutical composition comprising any of the CARs, functional portions, functional variants, nucleic acids, expression vectors, host cells (including populations thereof), and antibodies (including antigen binding portions thereof), and a pharmaceutically acceptable carrier. The inventive pharmaceutical compositions containing any of the inventive CAR materials can comprise more than one inventive CAR material, e.g., a CAR and a nucleic acid, or two or more different CARs. Alternatively, the pharmaceutical composition can comprise an inventive CAR material in combination with other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc. In a preferred embodiment, the pharmaceutical composition comprises the inventive host cell or populations thereof.

The inventive CAR materials can be provided in the form of a salt, e.g., a pharmaceutically acceptable salt. Suitable pharmaceutically acceptable acid addition salts include those derived from mineral acids, such as hydrochloric, hydrobromic, phosphoric, metaphosphoric, nitric, and sulphuric acids, and organic acids, such as tartaric, acetic, citric, malic, lactic, fumaric, benzoic, glycolic, gluconic, succinic, and arylsulphonic acids, for example, p-toluenesulphonic acid.

With respect to pharmaceutical compositions, the pharmaceutically acceptable carrier can be any of those conventionally used and is limited only by chemico-physical considerations, such as solubility and lack of reactivity with the active agent(s), and by the route of administration. The pharmaceutically acceptable carriers described herein, for example, vehicles, adjuvants, excipients, and diluents, are well-known to those skilled in the art and are readily available to the public. It is preferred that the pharmaceutically acceptable carrier be one which is chemically inert to the active agent(s) and one which has no detrimental side effects or toxicity under the conditions of use.

The choice of carrier will be determined in part by the particular inventive CAR material, as well as by the particular method used to administer the inventive CAR material. Accordingly, there are a variety of suitable formulations of the pharmaceutical composition of the invention. Preservatives may be used. Suitable preservatives may include, for example, methylparaben, propylparaben, sodium benzoate, and benzalkonium chloride. A mixture of two or more preservatives optionally may be used. The preservative or mixtures thereof are typically present in an amount of about 0.0001% to about 2% by weight of the total composition.

Suitable buffering agents may include, for example, citric acid, sodium citrate, phosphoric acid, potassium phosphate, and various other acids and salts. A mixture of two or more buffering agents optionally may be used. The buffering agent or mixtures thereof are typically present in an amount of about 0.001% to about 4% by weight of the total composition.

The concentration of inventive CAR material in the pharmaceutical formulations can vary, e.g., from less than about 1%, usually at or at least about 10%, to as much as about 20% to about 50% or more by weight, and can be selected primarily by fluid volumes, and viscosities, in accordance with the particular mode of administration selected.

Methods for preparing administrable (e.g., parenterally administrable) compositions are known or apparent to those skilled in the art and are described in more detail in, for example, *Remington: The Science and Practice of Pharmacy*, Lippincott Williams & Wilkins; 21st ed. (May 1, 2005).

The following formulations for oral, aerosol, parenteral (e.g., subcutaneous, intravenous, intraarterial, intramuscular, intradermal, interperitoneal, and intrathecal), and topical administration are merely exemplary and are in no way limiting. More than one route can be used to administer the inventive CAR materials, and in certain instances, a particular route can provide a more immediate and more effective response than another route.

Formulations suitable for oral administration can comprise or consist of (a) liquid solutions, such as an effective amount of the inventive CAR material dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant. Capsule forms can be of the ordinary hard or softshelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and other pharmacologically compatible excipients. Lozenge forms can comprise the inventive CAR material in a flavor, usually sucrose and acacia or tragacanth, as well as pastilles comprising the inventive CAR material in an inert base, such as gelatin and glycerin, or sucrose and acacia, emulsions, gels, and the like containing, in addition to, such excipients as are known in the art.

Formulations suitable for parenteral administration include aqueous and nonaqueous isotonic sterile injection solutions, which can contain antioxidants, buffers, bacteriostats, and solutes that render the formulation isotonic with the blood of the intended recipient, and aqueous and nonaqueous sterile suspensions that can include suspending agents, solubilizers, thickening agents, stabilizers, and preservatives. The inventive CAR material can be administered in a physiologically acceptable diluent in a pharmaceutical carrier, such as a sterile liquid or mixture of liquids, including water, saline, aqueous dextrose and related sugar solutions, an alcohol, such as ethanol or hexadecyl alcohol, a glycol, such as propylene glycol or polyethylene glycol, dimethylsulfoxide, glycerol, ketals such as 2,2-dimethyl-1, 3-dioxolane-4-methanol, ethers, poly(ethyleneglycol) 400, oils, fatty acids, fatty acid esters or glycerides, or acetylated fatty acid glycerides with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations, include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkyl-imidazoline quaternary ammonium salts, and (e) mixtures thereof.

The parenteral formulations will typically contain, for example, from about 0.5% to about 25% by weight of the inventive CAR material in solution. Preservatives and buffers may be used. In order to minimize or eliminate irritation at the site of injection, such compositions may contain one or more nonionic surfactants having, for example, a hydrophile-lipophile balance (HLB) of from about 12 to about 17. The quantity of surfactant in such formulations will typically range, for example, from about 5% to about 15% by weight. Suitable surfactants include polyethylene glycol sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Injectable formulations are in accordance with an embodiment of the invention. The requirements for effective pharmaceutical carriers for injectable compositions are well-known to those of ordinary skill in the art (see, e.g., *Pharmaceutics and Pharmacy Practice*, J.B. Lippincott Company, Philadelphia, PA, Banker and Chalmers, eds., pages 238-250 (1982), and *ASHP Handbook on Injectable Drugs*, Toissel, 4th ed., pages 622-630 (1986)).

Topical formulations, including those that are useful for transdermal drug release, are well known to those of skill in the art and are suitable in the context of embodiments of the invention for application to skin. The inventive CAR material, alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer. Such spray formulations also may be used to spray mucosa.

An "effective amount" or "an amount effective to treat" refers to a dose that is adequate to prevent or treat cancer in an individual. Amounts effective for a therapeutic or prophylactic use will depend on, for example, the stage and severity of the disease or disorder being treated, the age, weight, and general state of health of the patient, and the judgment of the prescribing physician. The size of the dose will also be determined by the active selected, method of administration, timing and frequency of administration, the existence, nature, and extent of any adverse side-effects that might accompany the administration of a particular active, and the desired physiological effect. It will be appreciated by one of skill in the art that various diseases or disorders could require prolonged treatment involving multiple administrations, perhaps using the inventive CAR materials in each or various rounds of administration. By way of example and not intending to limit the invention, the dose of the inventive CAR material can be about 0.001 to about 1000 mg/kg body weight of the subject being treated/day, from about 0.01 to about 10 mg/kg body weight/day, about 0.01 mg to about 1 mg/kg body weight/day. In an embodiment of the invention, the dose may be from about $1 \times 10^4$ to about $1 \times 10^8$ cells expressing the inventive CAR material per kg body weight. When the inventive CAR material is a host cell, an exemplary dose of host cells may be a minimum of one million cells (1 mg cells/dose). When the inventive CAR material is a nucleic acid packaged in a virus, an exemplary dose of virus may be 1 ng/dose.

For purposes of the invention, the amount or dose of the inventive CAR material administered should be sufficient to effect a therapeutic or prophylactic response in the subject or animal over a reasonable time frame. For example, the dose of the inventive CAR material should be sufficient to bind to antigen, or detect, treat or prevent disease in a period of from about 2 hours or longer, e.g., about 12 to about 24 or more hours, from the time of administration. In certain embodiments, the time period could be even longer. The dose will be determined by the efficacy of the particular inventive CAR material and the condition of the animal (e.g., human), as well as the body weight of the animal (e.g., human) to be treated.

For purposes of the invention, an assay, which comprises, for example, comparing the extent to which target cells are lysed and/or IFN-γ is secreted by T cells expressing the inventive CAR upon administration of a given dose of such T cells to a mammal, among a set of mammals of which is each given a different dose of the T cells, could be used to determine a starting dose to be administered to a mammal. The extent to which target cells are lysed and/or IFN-γ is secreted upon administration of a certain dose can be assayed by methods known in the art.

In addition to the aforedescribed pharmaceutical compositions, the inventive CAR materials can be formulated as inclusion complexes, such as cyclodextrin inclusion complexes, or liposomes. Liposomes can serve to target the inventive CAR materials to a particular tissue. Liposomes also can be used to increase the half-life of the inventive CAR materials. Many methods are available for preparing liposomes, as described in, for example, Szoka et al., Ann. Rev. Biophys. Bioeng., 9, 467 (1980) and U.S. Pat. Nos. 4,235,871, 4,501,728, 4,837,028, and 5,019,369.

The delivery systems useful in the context of embodiments of the invention may include time-released, delayed release, and sustained release delivery systems such that the delivery of the inventive composition occurs prior to, and with sufficient time to cause, sensitization of the site to be treated. The inventive composition can be used in conjunction with other therapeutic agents or therapies. Such systems can avoid repeated administrations of the inventive composition, thereby increasing convenience to the subject and the physician, and may be particularly suitable for certain composition embodiments of the invention.

Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are lipids including sterols such as cholesterol, cholesterol esters, and fatty acids or neutral fats such as mono-di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which the active composition is contained in a form within a matrix such as those described in U.S. Pat. Nos. 4,452,775, 4,667,014, 4,748,034, and 5,239,660 and (b) diffusional systems in which an active component permeates at a controlled rate from a polymer such as described in U.S. Pat. Nos. 3,832,253 and 3,854,480. In addition, pump-based hardware delivery systems can be used, some of which are adapted for implantation.

One of ordinary skill in the art will readily appreciate that the inventive CAR materials of the invention can be modified in any number of ways, such that the therapeutic or prophylactic efficacy of the inventive CAR materials is increased through the modification. For instance, the inventive CAR materials can be conjugated either directly or indirectly through a linking moiety to a targeting moiety. The practice of conjugating compounds, e.g., inventive CAR materials, to targeting moieties is known in the art. See, for instance, Wadwa et al., *J. Drug Targeting* 3: 111 (1995) and U.S. Pat. No. 5,087,616.

Alternatively, the inventive CAR materials can be modified into a depot form, such that the manner in which the inventive CAR materials is released into the body to which it is administered is controlled with respect to time and location within the body (see, for example, U.S. Pat. No. 4,450,150). Depot forms of inventive CAR materials can be, for example, an implantable composition comprising the inventive CAR materials and a porous or non-porous material, such as a polymer, wherein the inventive CAR materials are encapsulated by or diffused throughout the material and/or degradation of the non-porous material. The depot is then implanted into the desired location within the body and the inventive CAR materials are released from the implant at a predetermined rate.

When the inventive CAR materials are administered with one or more additional therapeutic agents, one or more additional therapeutic agents can be coadministered to the mammal. By "coadministering" is meant administering one or more additional therapeutic agents and the inventive CAR materials sufficiently close in time such that the inventive CAR materials can enhance the effect of one or more additional therapeutic agents, or vice versa. In this regard, the inventive CAR materials can be administered first and the one or more additional therapeutic agents can be administered second, or vice versa. Alternatively, the inventive CAR materials and the one or more additional therapeutic agents can be administered simultaneously.

An exemplary therapeutic agent that can be co-administered with the CAR materials is a T cell active cytokine, such as IL-2. It is believed that IL-2 enhances the therapeutic effect of the inventive CAR materials. Without being bound by a particular theory or mechanism, it is believed that IL-2 enhances therapy by enhancing the in vivo expansion of the numbers and/or effector function of cells expressing the inventive CARs. Other exemplary cytokines include IL-7 and IL-15. For purposes of the inventive methods, wherein host cells or populations of cells are administered to the mammal, the cells can be cells that are allogeneic or autologous to the mammal.

It is contemplated that the inventive CARs materials can be used in methods of treating or preventing a disease in a mammal. Without being bound to a particular theory or mechanism, the inventive CARs have biological activity, e.g., ability to recognize antigen, e.g., TSLPR, such that the CAR when expressed by a cell is able to mediate an immune response against the cell expressing the antigen, e.g., TSLPR, for which the CAR is specific. In this regard, an embodiment of the invention provides a method of treating or preventing cancer in a mammal, comprising administering to the mammal the CARs, the nucleic acids, the recombinant expression vectors, the host cells, the population of cells, the antibodies and/or the antigen binding portions thereof, and/or the pharmaceutical compositions of the invention in an amount effective to treat or prevent cancer in the mammal.

An embodiment of the invention further comprises lymphodepleting the mammal prior to administering the inventive CAR materials. Examples of lymphodepletion include, but may not be limited to, nonmyeloablative lymphodepleting chemotherapy, myeloablative lymphodepleting chemotherapy, total body irradiation, etc.

For purposes of the inventive methods, wherein host cells or populations of cells are administered, the cells can be cells that are allogeneic or autologous to the mammal. Preferably, the cells are autologous to the mammal.

The mammal referred to herein can be any mammal. As used herein, the term "mammal" refers to any mammal, including, but not limited to, mammals of the order Rodentia, such as mice and hamsters, and mammals of the order Logomorpha, such as rabbits. The mammals may be from the order Carnivora, including Felines (cats) and Canines (dogs). The mammals may be from the order Artiodactyla, including Bovines (cows) and Swines (pigs) or of the order Perssodactyla, including Equines (horses). The mammals may be of the order Primates, Ceboids, or Simoids (monkeys) or of the order Anthropoids (humans and apes). Preferably, the mammal is a human.

With respect to the inventive methods, the cancer can be any cancer, including any of acute lymphocytic cancer, acute myeloid leukemia, alveolar rhabdomyosarcoma, bladder cancer (e.g., bladder carcinoma), bone cancer, brain cancer (e.g., medulloblastoma), breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, esophageal cancer, cervical cancer, fibrosarcoma, gastrointestinal carcinoid tumor, head and neck cancer (e.g., head and neck squamous cell carcinoma), Hodgkin lymphoma, hypopharynx cancer, kidney cancer, larynx cancer, leukemia, liquid tumors, liver cancer, lung cancer (e.g., non-small cell lung carcinoma and lung adenocarcinoma), lymphoma, mesothelioma, mastocytoma, melanoma, multiple myeloma, nasopharynx cancer, non-Hodgkin lymphoma, B-chronic lymphocytic leukemia, hairy cell leukemia, acute lymphocytic leukemia (ALL), and Burkitt's lymphoma, ovarian cancer, pancreatic cancer, peritoneum, omentum, and mesentery cancer, pharynx cancer, prostate cancer, rectal cancer, renal cancer, skin cancer, small intestine cancer, soft tissue cancer, solid tumors, synovial sarcoma, gastric cancer, testicular cancer, thyroid cancer, and ureter cancer. Preferably, the cancer is characterized by the expression of TSLPR.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount or any level of treatment or prevention of cancer in a mammal. Furthermore, the treatment or prevention provided by the inventive method can include treatment or prevention of one or more conditions or symptoms of the disease, e.g., cancer, being treated or prevented. Also, for purposes herein, "prevention" can encompass delaying the onset of the disease, or a symptom or condition thereof.

Another embodiment of the invention provides a method of detecting the presence of cancer in a mammal, comprising: (a) contacting a sample comprising one or more cells from the mammal with the CARs, the nucleic acids, the recombinant expression vectors, the host cells, the population of cells, the antibodies, and/or the antigen binding portions thereof, or the pharmaceutical compositions of the invention, thereby forming a complex, (b) and detecting the complex, wherein detection of the complex is indicative of the presence of cancer in the mammal.

Another embodiment of the invention includes a method of determining whether a subject with a proliferative disorder is a candidate for treatment with a chimeric antigen receptor comprising an antigen binding domain specific for TSLPR, the method comprising measuring TSLPR expression levels in a biological sample from the subject; and determining if the TSLPR expression levels of the biological sample are increased compared to a sample from a control subject without the proliferative disorder.

The sample may be obtained by any suitable method, e.g., biopsy or necropsy. A biopsy is the removal of tissue and/or cells from an individual. Such removal may be to collect tissue and/or cells from the individual in order to perform experimentation on the removed tissue and/or cells. This experimentation may include experiments to determine if the individual has and/or is suffering from a certain condition or disease-state. The condition or disease may be, e.g., cancer.

With respect to an embodiment of the inventive method of detecting the presence of a proliferative disorder, e.g., cancer, in a mammal, the sample comprising cells of the mammal can be a sample comprising whole cells, lysates thereof, or a fraction of the whole cell lysates, e.g., a nuclear or cytoplasmic fraction, a whole protein fraction, or a nucleic acid fraction. If the sample comprises whole cells, the cells can be any cells of the mammal, e.g., the cells of any organ or tissue, including blood cells or endothelial cells.

The contacting can take place in vitro or in vivo with respect to the mammal. Preferably, the contacting is in vitro.

Also, detection of the complex can occur through any number of ways known in the art. For instance, the inventive CARs, polypeptides, proteins, nucleic acids, recombinant expression vectors, host cells, populations of cells, or antibodies, or antigen binding portions thereof, described herein, can be labeled with a detectable label such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

Methods of testing a CAR for the ability to recognize target cells and for antigen specificity are known in the art. For instance, Clay et al., *J. Immunol.*, 163: 507-513 (1999), teaches methods of measuring the release of cytokines (e.g., interferon-γ, granulocyte/monocyte colony stimulating factor (GM-CSF), tumor necrosis factor a (TNF-α) or interleukin 2 (IL-2)). In addition, CAR function can be evaluated by measurement of cellular cytotoxicity, as described in Zhao et al., *J. Immunol.*, 174: 4415-4423 (2005).

Another embodiment of the invention provides the use of the CARs, nucleic acids, recombinant expression vectors, host cells, populations of cells, antibodies, or antigen binding portions thereof, and/or pharmaceutical compositions of the invention, for the treatment or prevention of a proliferative disorder, e.g., cancer, in a mammal. The cancer may be any of the cancers described herein. Preferably, the cancer is BCP-ALL.

The following examples further illustrate the invention but, of course, should not be construed as in any way limiting its scope.

Example 1

This example demonstrates the generation and testing of the 3G11 TSLPR CARs—Short 3G11 (SEQ ID NOS: 39 and 43) and Long 3G11 (SEQ ID NOS: 40 and 44). The leader sequence is initially encoded and enhances trafficking to the cell surface. It is likely to be cleaved off in the mature form.

The following B cell acute lymphoblastic leukemia (ALL) cell lines were used: MUTZ-5 (DSMZ ACC 490), REH-TSLPR (transduced with human TSLPR) and REH as a TSLPR negative control. Cell line cultures in media were supplemented with 10% heat-inactivated FBS (Gemini Bioproducts, West Sacramento, CA, USA), 10 mM HEPES, 100 U/mL penicillin, 100 ug/mL streptomycin, 2 mM L-glutamine (Invitrogen, Carlsbad, CA, USA). The 293T retroviral vector packaging cell line (Clonetech, Mountain View, CA, USA) was cultured in DMEM (Invitrogen). In addition, pre-B cell ALL xenografts JH331, JH352, NH362 which naturally overexpress TSLPR were used as in vivo models. These are patient-derived ALL xenografts established after patient consent on an IRB-approved protocol. Human PBMCs from healthy donors were obtained from the Department of Transfusion Medicine at the NIH Clinical Center, under an NIH IRB approved protocol after informed consent in accordance with the Declaration of Helsinki. The human PBMC were cultured in AIMV with 5% FBS.

Construction of TSLPR chimeric antigen receptors. TSLPR binding single chain fragment variable (scFv) sequences were determined from the anti-TSLPR producing hybridoma 3G11 (Lu et al., *J. Exp. Med.*, 2009, 206:2111-2119, incorporated herein by reference). 3G11 was cultured in RPMI 1640 medium with sodium pyruvate (1 mM), penicillin streptomycin (pen/strep) and 10% Fetal Bovine serum. When the cells were ready to split, the medium was changed to RPMI medium plus sodium pyruvate, pen/strep, and 5% of ultra-low IgG FBS from GIBCO (Grand Island, NY, USA; Cat #16250) for antibody production or harvesting the cells for total RNA extraction. 3G11 total RNA were extracted with RNeasy Mini kit (Qiagen, Valencia, CA, USA) and then reverse transcribed into cDNA with SuperScript III (Invitrogen). The cDNA were subsequently used for PCR amplification with the combination of the degenerated primers from the variable region of the heavy chain and the constant gamma chain for the variable region of the heavy chain ($V_H$), and similarly, with the degenerated primer from the kappa variable region and the specific primer from the kappa chain constant region for the kappa light chain ($V_L$) (Kettleborough et al., Eur. J. Immunol., 1993, 23:206-211, incorporated by reference herein in its entirety). The PCR reagents were either purchased from Roche Diagnostics (PCR Buffer Set, Indianapolis, IN, USA) or from New England BioLabs (One Taq DNA Polymerase, Ipswich, MA, USA). The following PCR conditions were applied for the amplification: 95° C. for 1 min, 35 cycles of (95° C. for 15 sec, 50° C. for 30 sec, 68° C. for 45 sec), final extension at 68° C. for 5 min. The resulting PCR products were gel purified and cloned into TOPO vector (TOPO TA Cloning Kit for Sequencing, Invitrogen) and then transformed into One Shot® TOP10 Chemically Competent *E. coli* (Invitrogen). Single clones were picked for mini-prep and the resulting plasmids were sent for sequencing analysis. To overcome the secondary structure at the beginning of the heavy chain variable region, a new antibody subtype specific reverse primer was designed which is closer to the beginning of the 5' to combine with the degenerated primer at the 5' end for amplification of the 5' region of the $V_H$. A PCR enhancer Betaine was used at 1 M to facilitate the PCR reaction. For construction of the long CAR constructs, the CH2CH3 domains from IGHG1 (gb|AAC82527.1 aa 98-329) were included. The leader sequence for the scFv coding for T-cell surface glycoprotein CD8 alpha chain was included to facilitate membrane trafficking. The CAR-encoding amino acid sequences were reverse translated, codon optimized, and synthesized as single constructs (DNA 2.0, Menlo Park, CA, USA). These constructs were then subcloned into a third generation lentivirial plasmid (pELNS-19BBzeta) containing a CD8 transmembrane domain, a 41BB (CD137) signaling domain and a CD3zeta domain (previously described in Hudecek et al., "The non-signaling extracellular spacer domain of chimeric antigen receptors is decisive for in vivo antitumor activity," Cancer Immunol. Res., 2014 and Milone et al., Molecular Therapy, 2009, 17(8): 1453-1464, each of which are incorporated herein by reference).

Lentiviral vector production and T cell transduction. TSLPR CAR-encoding lentiviral vectors were produced by transient transfection of the 293T cell line as previously described in Hudecek et al., supra, and Milone et al., supra. Briefly, 293T cells were plated into poly-D lysine coated 15 cm plates (BD Bioscience, San Jose, CA, USA). The following day, 293T cells were transfected using lipofectamine 2000 (Invitrogen) with plasmids encoding the TSLPR CAR along with packaging and envelope vectors pMDLg/pRRE, pMD-G, and pRSV-Rev which were kindly provided by Dr. R. Morgan (Surgery Branch, Center for Cancer Research, NCI, NIH). Lenti-viral supernatants were collected 48 to 72 hours post-transfection, centrifuged at 3000 RPM for 10 minutes to remove cell debris, then stored at −80° C. Human PBMCs from normal donors were activated with a 1:1 ratio of CD3/CD28 microbeads (Invitrogen) in AIM-V media containing 40 IU/mL recombinant IL-2 (teceleukin, rhIL-2; Roche, Indianapolis, IN, USA) for 24 hours. Activated T cells were resuspended at 2 million cells per 3 ml of lentiviral supernatants plus 1 ml of fresh AIM-V media with 10 μg/ml protamine sulfate and 40 IU/ml IL2 and cultured in 6-well plates. Plates were centrifuged at 1000 g for 2 hours at 32° C. and then were incubated at 37° C. overnight. A second transduction was performed the following day. On the third day following transduction, the CD3/CD28 beads were removed and the cells were cultured at 300,000 cells/mL in AIM-V containing 100 IU/mL IL-2 with fresh IL2-containing media added every 2 to 3 days until harvest at day 8 or 9.

Flow cytometry analysis. Surface expression of CAR-transduced T cells was determined by flow cytometry using a TSLPR-Fc (R&D Systems, Minneapolis, MN, USA) followed by incubation with PE-F(ab)$_2$ or APC-F(ab)$_2$ specific for human IgG-Fc (Jackson ImmunoResearch Laboratories, West Grove, PA, USA). Alternatively, biotin-conjugated protein L (Thermo Scientific, Waltham, MA, USA) was used to detect CAR expression after incubation with streptavidin-conjugated PE (BD Bioscience). Expression of CD19, CD22, and TSLPR on leukemia lines were detected using the following anti-human antibodies: CD45-PerCP-Cy5.5 (eBioscience, San Diego, CA, USA), CD19-Pac-Blue, CD19-APC-Cy7, CD10_PE-Cy7, and CD22-PE, TSLPR-APC (BioLegend, San Diego, CA, USA), and the T cells were characterized with the following antibodies: CD3-APC-Cy7, CCR7-FITC (CD197), CD45RA-APC, CD4-PacBlue, (BioLegend), CD45-PerCP-Cy5.5 (eBioscience), CD8-V500 (BD, Franklin Lakes, NJ, USA). The binding of the 3G11 hybridoma supernatant to the TSLPR expression ALL lines was detected with Goat-anti-mouse-PE (BD Bioscience). Dead cells were excluded by staining with Fixable Viability Dye eFluor® 506 (eBioscience).

Cellular cytotoxicity and cytokine assays. Both REH-TSLPR and MUTZS cell lines express high level of TSLPR. REH was used as negative control for TSLPR expression. Target cells were labeled with 100 uCi $^{51}$Cr (Perkin Elmer, Waltham, MA, USA) for 1 hour. After washing, 5,000 targets per well were coincubated for 4 to 6 hours with bead-purified Pan T Cell II isolation kit (Miltenyi Biotec, San Diego, CA, USA) transduced T cells at various effector to target (E:T) ratios. Assay supernatants were counted for $^{51}$Cr release using LumaPlates (Perkin Elmer) and a Top Count Reader (Packard, Meriden, CT). Specific lysis was calculated as follows: % Lysis=(experimental Lysis−spontaneous lysis)/(maximum lysis−spontaneous lysis)×100. Cytokine levels in supernatants were determined after 24-hours using a multiplex assay (Meso Scale Discovery, Rockville, MD, USA). For studies including K562 cells. K562 cells are immortalized human myelogenous erythroleukemia. They do not express TSLPR on the cell surface and are normally used for detecting NK activity. K562 and REH were used as negative target controls, the REH-TSLPR and MUTZ5 were used as the positive target controls. The CAR transduced T cells were NK depleted with Pan-T isolation kit and then incubated with the different target cells. For cytokine production, the following protocol was used: count the target cell and wash 3× times and resuspend in RPMI at 1E6/ml, and put 100 ul into each well in 96-well plate (Final 1E5/well); count transduced T cell and wash 3× times and resuspend in RPMI at 1E6/ml, and put 100 ul into each well in 96-well plate (final 1E5/well); set up a T cell only and tumor cell only; incubate for 24 hours at 37° C. and harvest 100 ul of the supernatant for testing of the cytokines production. All samples were in triplicate.

In vivo studies. Animal studies were carried out under protocols approved by the NCI Bethesda Animal Care and Use Committee. Pre B cell ALL cell lines and xenografts were IV injected into NSG mice (NOD scid gamma, NOD·Cg-Prkdcscid Il2rgtm1Wjl/SzJ JAX, Jackson ImmunoResearch Laboratories). For luciferase-expressing lines, leukemia was detected using the Xenogen IVIS Lumina (Caliper Life Sciences). NSG mice were injected intraperitoneally with 3 mg D-luciferin (Caliper Life Sciences) and were imaged 6 minutes later with an exposure time of 3 min.

Living Image Version 4.1 software (Caliper Life Sciences, Hopkinton, MA, USA) was used to analyze the bioluminescent signals for each mouse as photons/s/cm$^2$/sr. Non-luciferase expressing xenografts were tracked with flow cytometry of peripheral blood or bone marrow.

Figure 2:
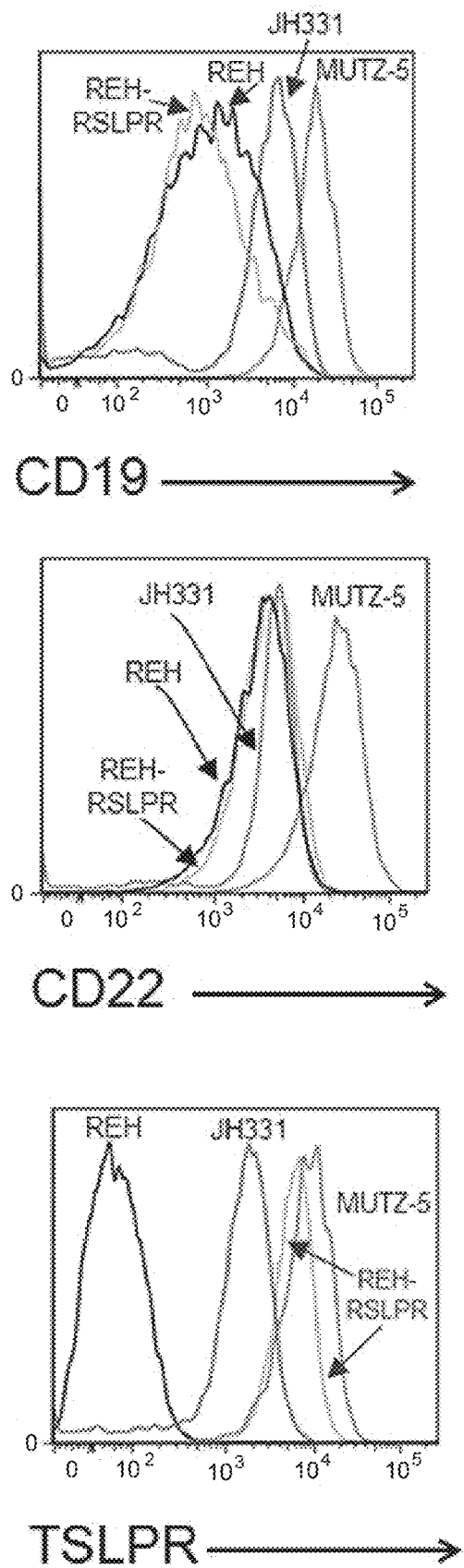
FIG. 2 presents flow cytometry graphs showing the surface expression of CD19, CD22, and TSLPR on stable leukemia cell lines and JH331, which is derived from patient leukemia blast, naturally overexpressed TSLPR, and cannot be cultured in vitro. The y-axis is counts, x-axis is mean fluorescence intensity.
Figure 3:
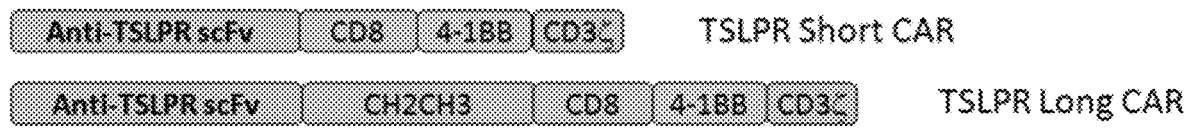
FIG. 3 presents diagrammatic representations of short and long CARs in accordance with certain embodiments of the present invention.
Figure 4:
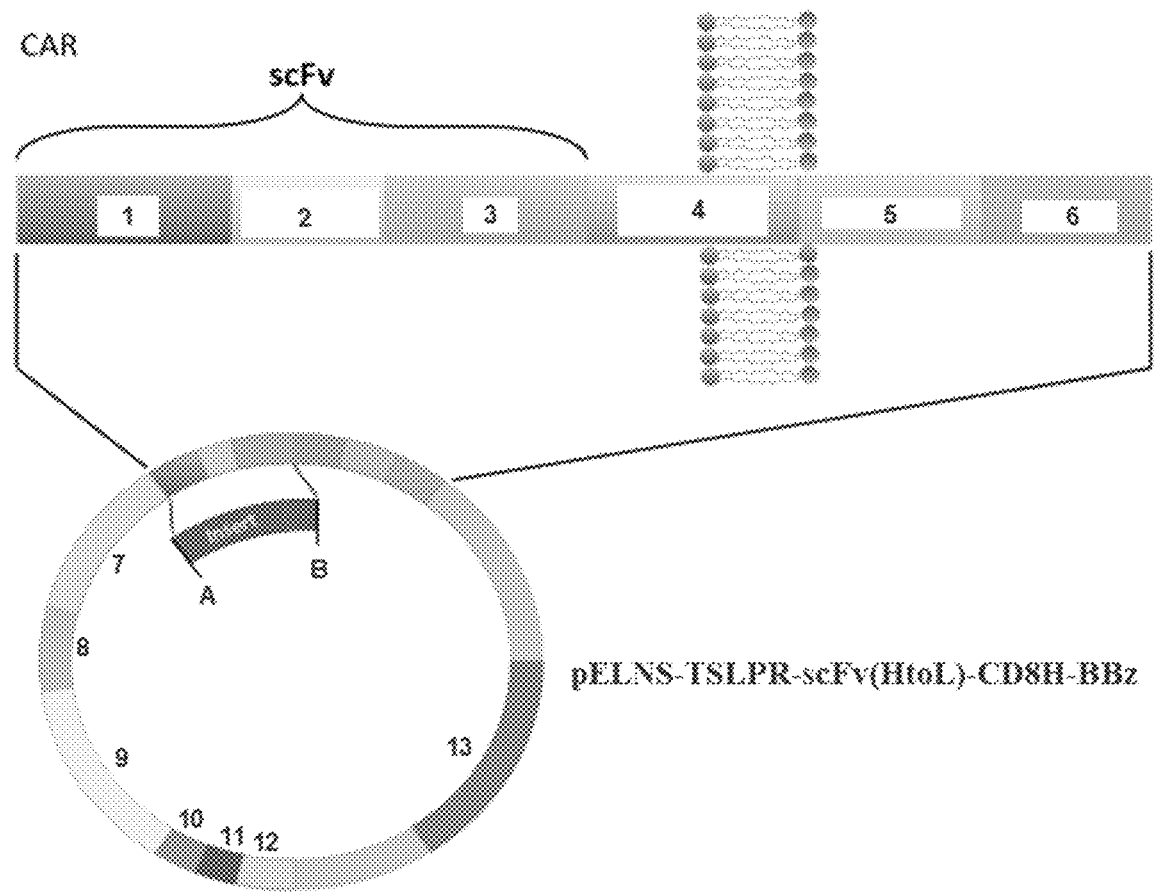
FIG. 4 presents a diagrammatic representation of construction of a vector encoding a CAR in accordance with certain embodiments of the present invention.
Figure 5B:
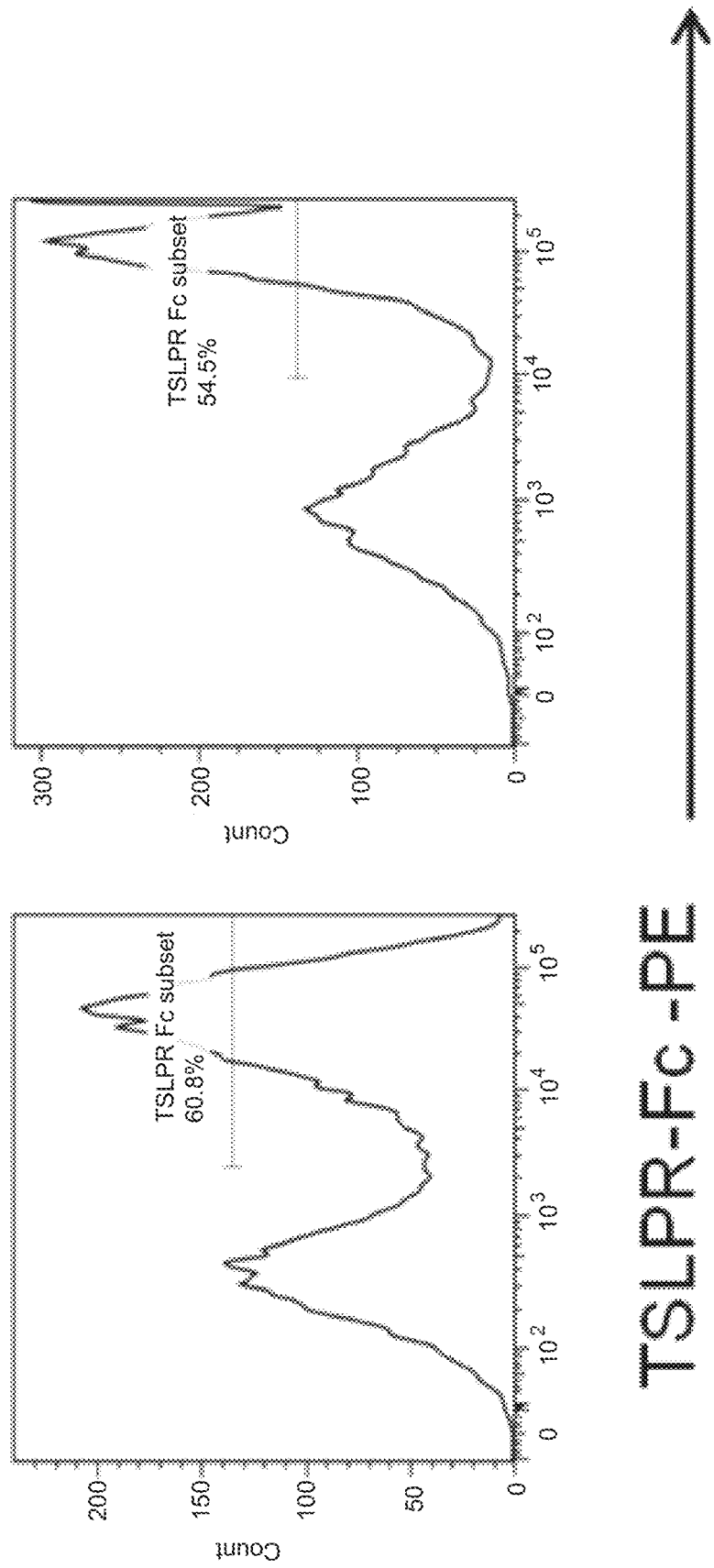

Binding of an anti-TSLPR antibody, produced by the 3G11 hybridoma, to TSLPR-overexpressing precursor-B cell acute lymphoblastic leukemias ("TSLPRhi ALL") was confirmed (FIG. 1). FIG. 2 shows expression determined by a commercial TSLPR antibody. The sequences for the heavy and light chain variable regions (Fv) were then determined. Single chain Fv (scFv) sequences were constructed using a glycine linker and inserted into a chimeric antigen receptor lentiviral vector backbone encoding CD8α hinge and CD8 transmembrane regions with CD3zeta and 41BB (CD137) intracellular domains (FIGS. 3 and 4). Because distance of the scFv from the T cell surface may affect CAR function, a construct containing an immunoglobulin CH2CH3 spacer domain between the scFv and the transmembrane sequence was also generated for the "long" CAR. Lentiviral vectors encoding the TSLPR CARs were then used to transduce CD3/CD28 bead-activated human T cells resulting in a high efficiency of gene transfer as detected by both protein L and a TSLPR Fc fusion protein (FIGS. 5A and 5B). Although transduction occurred on days 2 and 3 of culture, the fraction of CAR-expressing T cells increased during subsequent culture, suggesting preferential survival or enhanced expansion of T cells expressing the CAR construct. TSLPR has limited expression in normal tissues outside of the immune system. It has been found on dendritic cells and subsets of activated T cells. Based on immunohistochemistry on a normal pediatric tissue microarray, where there were scattered rare cells in lymphoid tissues with robust membraneous expression, possibly representing dendritic cells. There was also some staining in pancreas, renal tubular cells, and colonic mucosa, where the staining in these tissues was not consistent with cell surface expression. There was no staining in the heart. As has been shown with some primary preB ALL, a TSLPRhi ALL cell line (MUTZ5) and a human TSLPRhi xenograph (JHH331) express TSLPR at comparable levels to CD19 and CD22 (FIG. 2).

Figure 6:
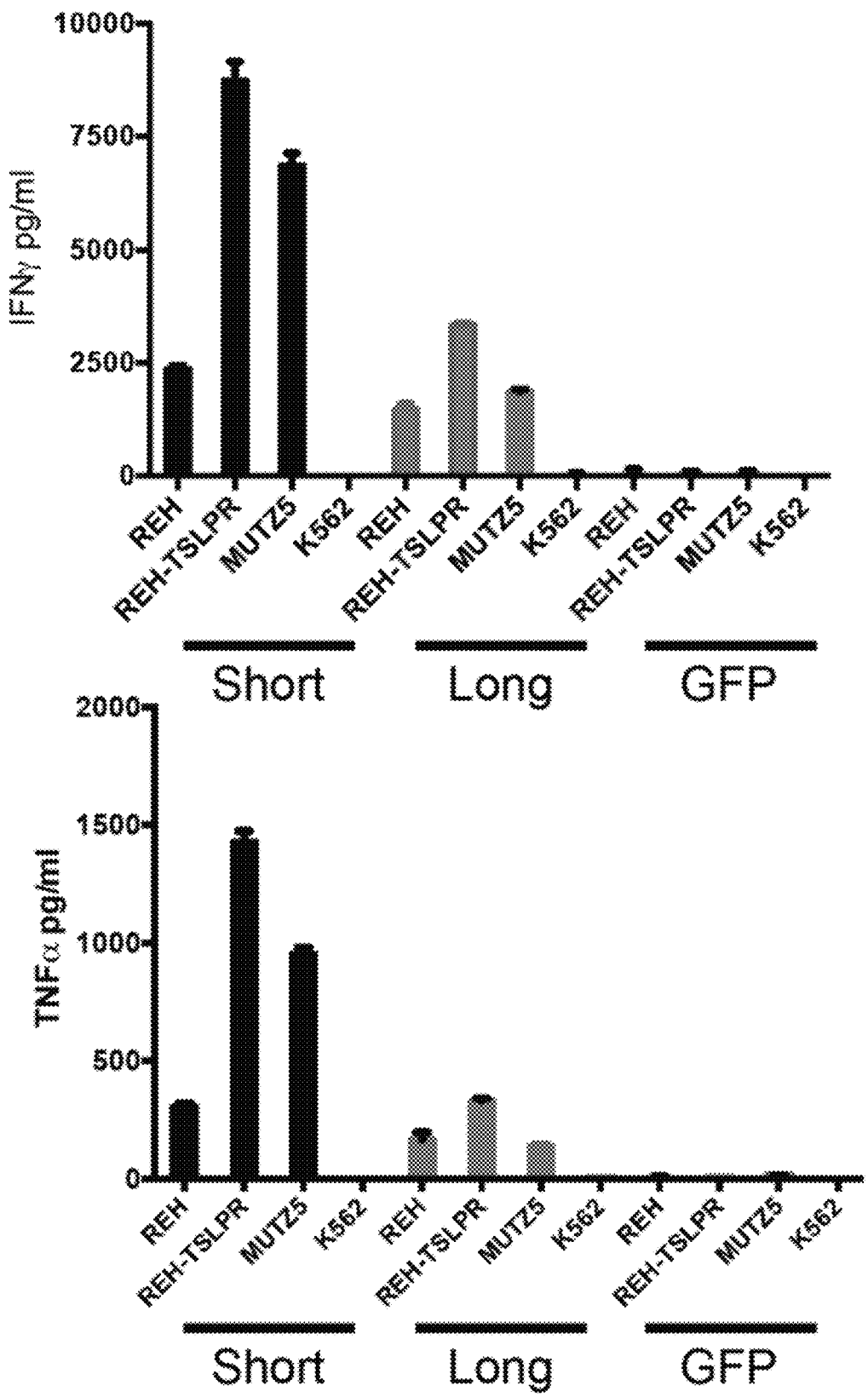
FIG. 6 is a bar graph showing cytolytic cytokine release by TSLPR CAR transduced T cells in accordance with certain embodiments of the present invention.
Figure 7E:
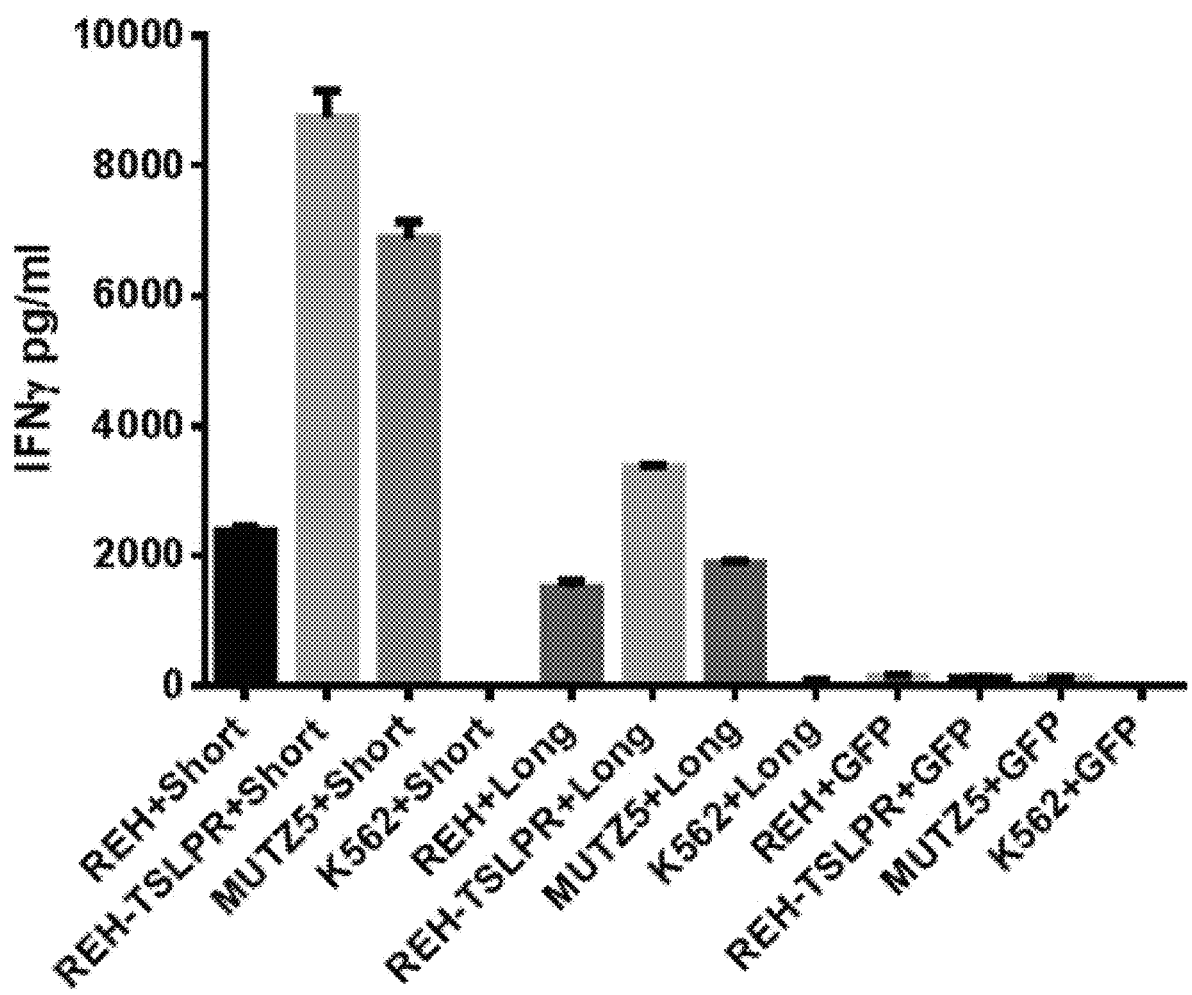
Figure 7F:
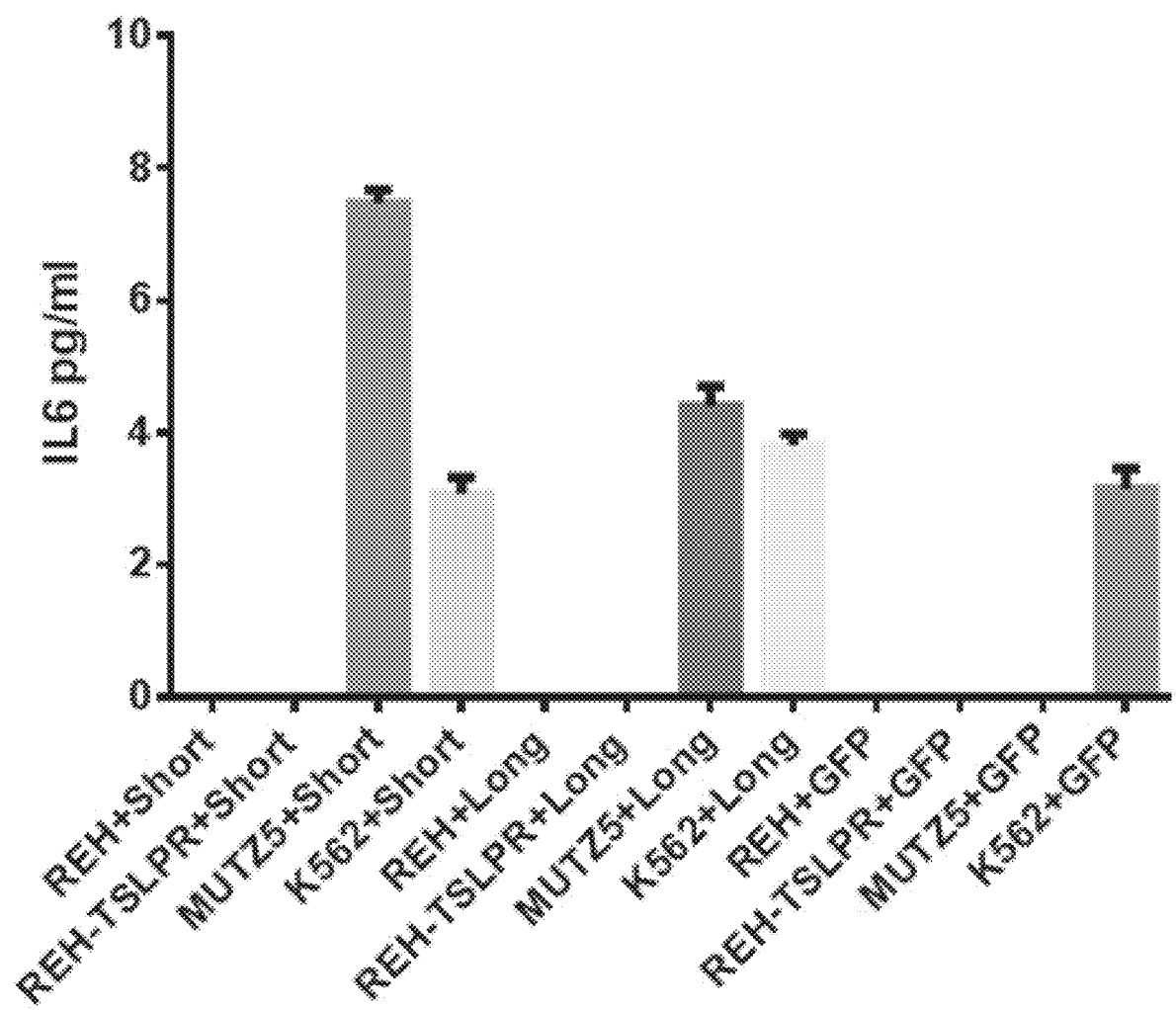
Figure 7G:
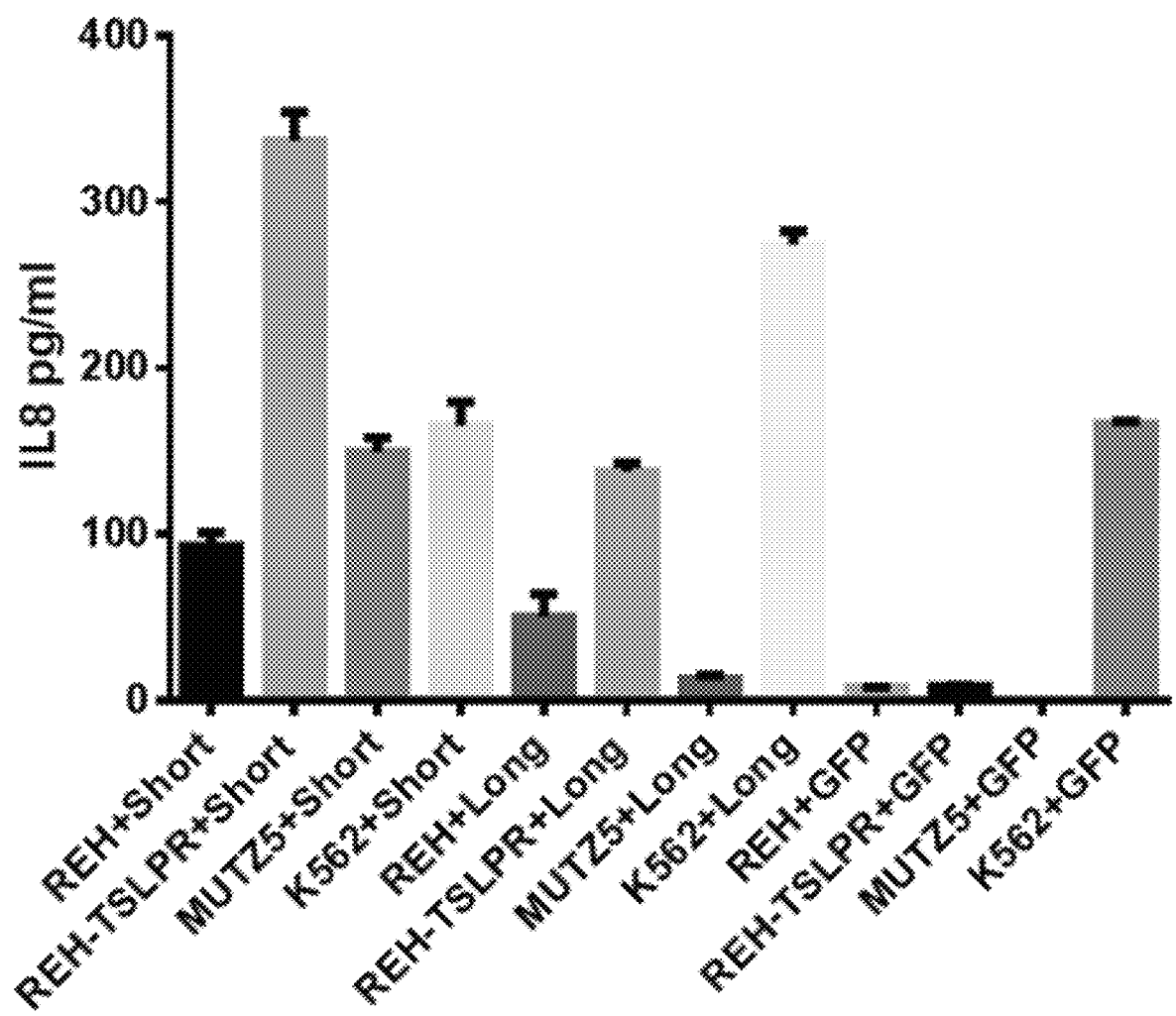
Figure 7H:
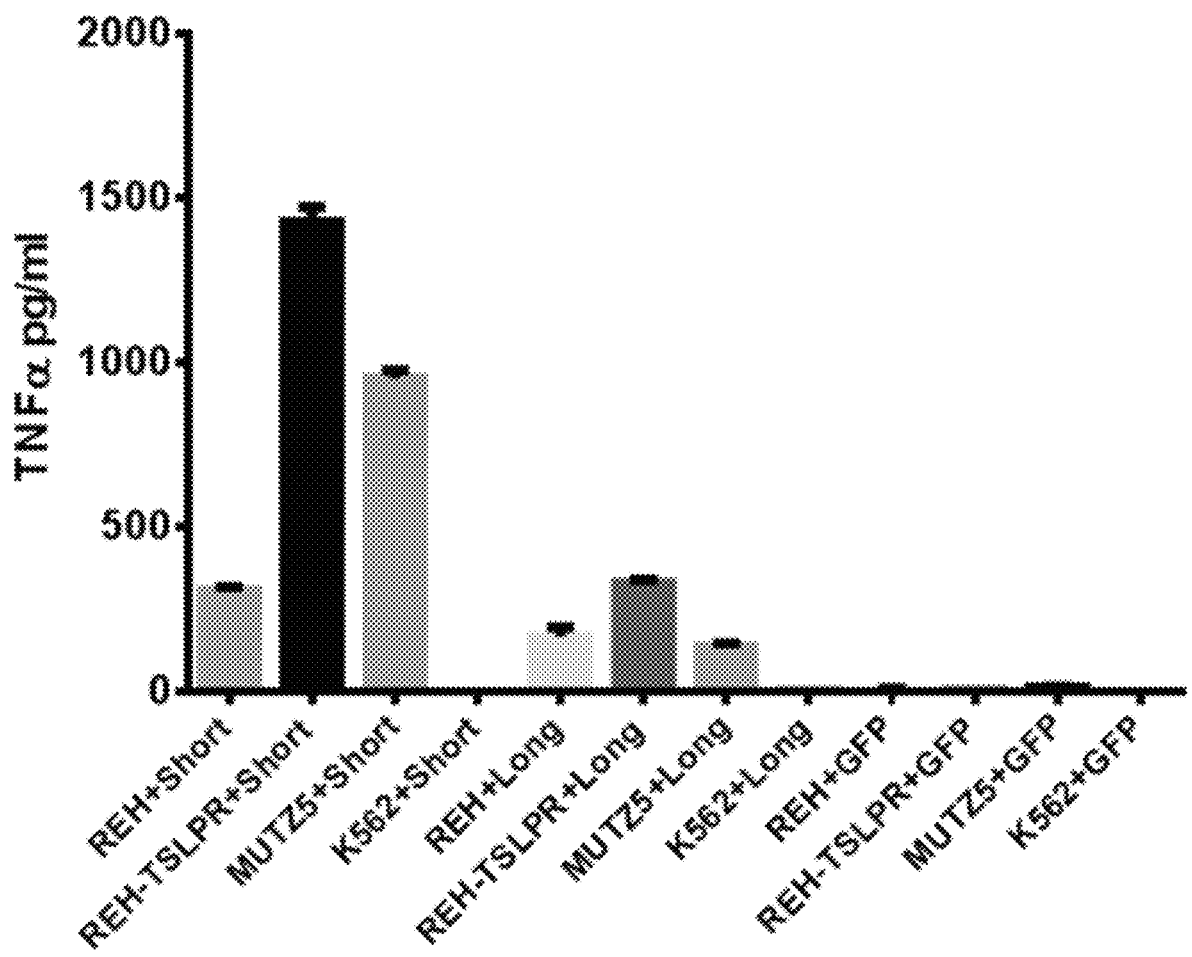
Figure 8A:
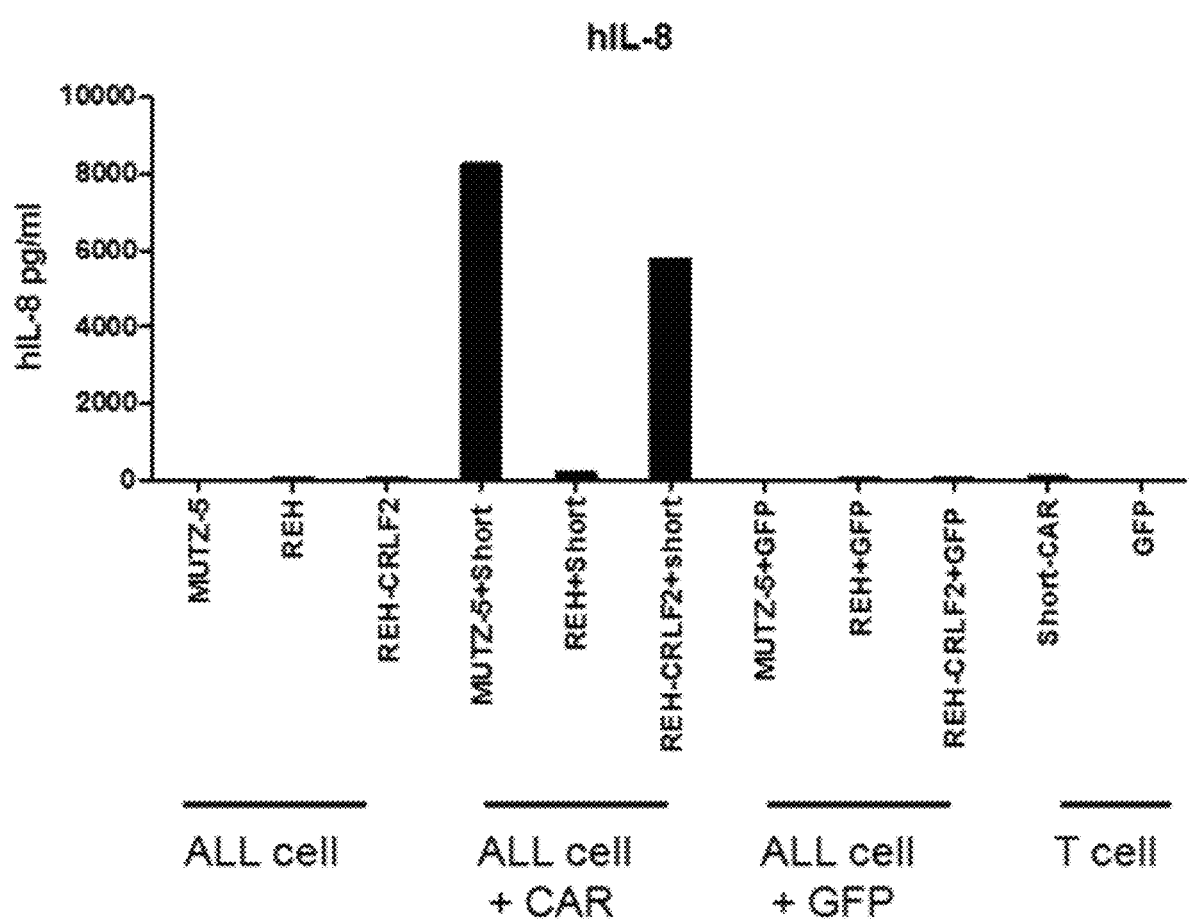
Figure 8E:
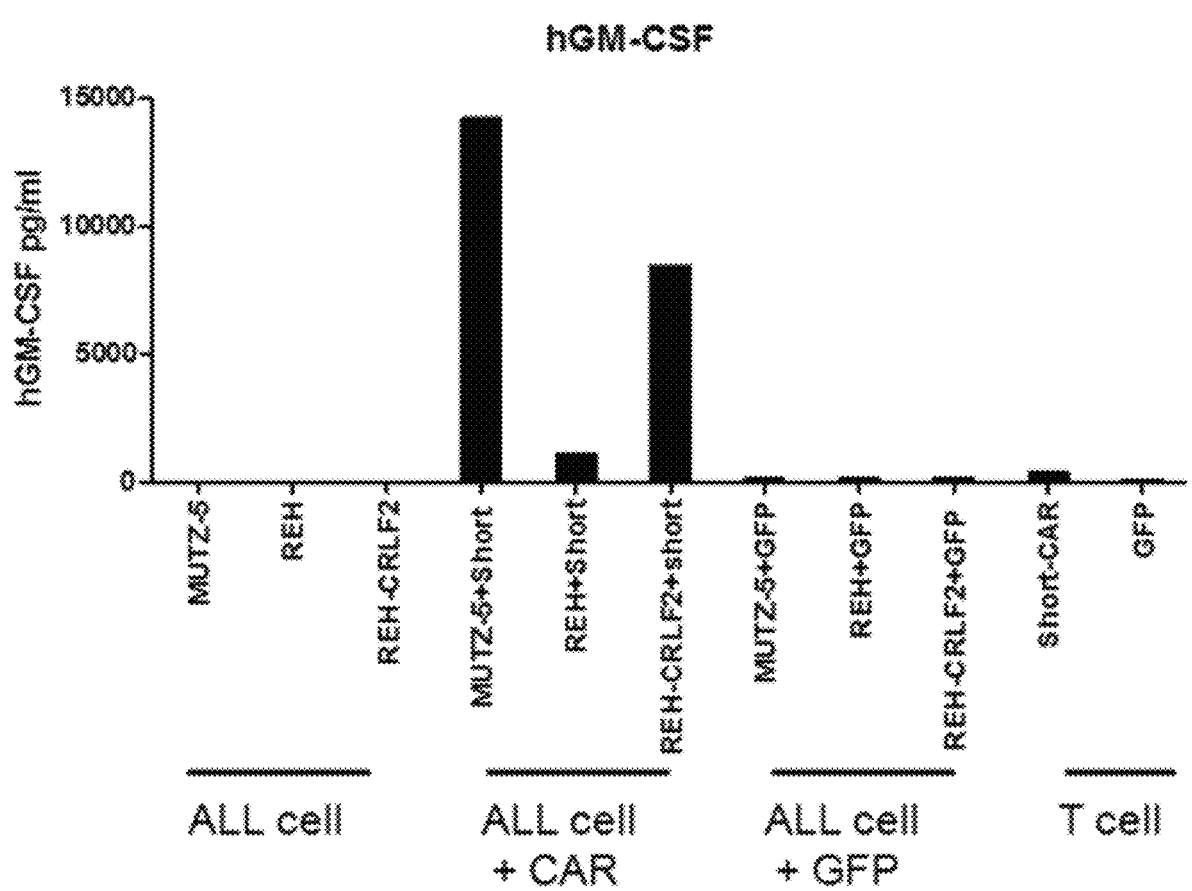
Figure 9A:
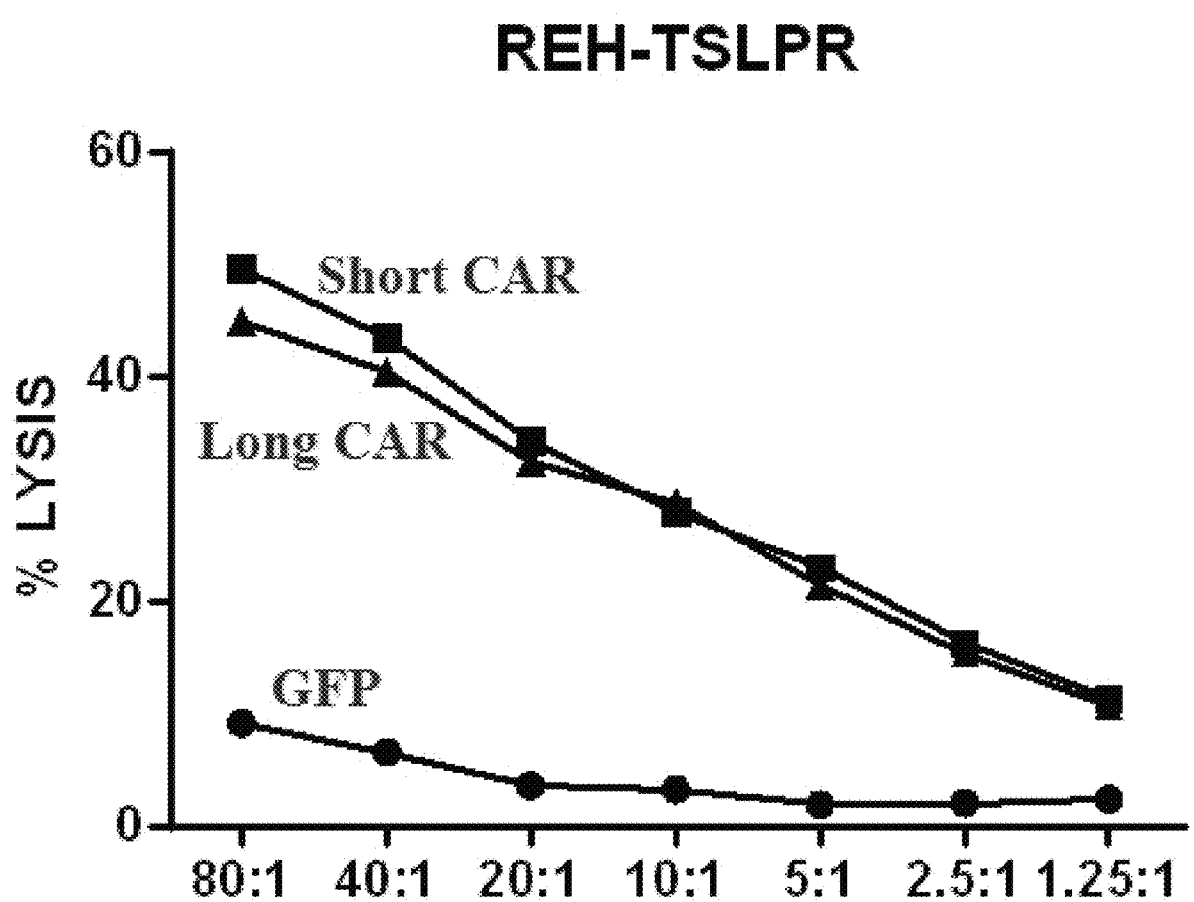
Figure 9B:
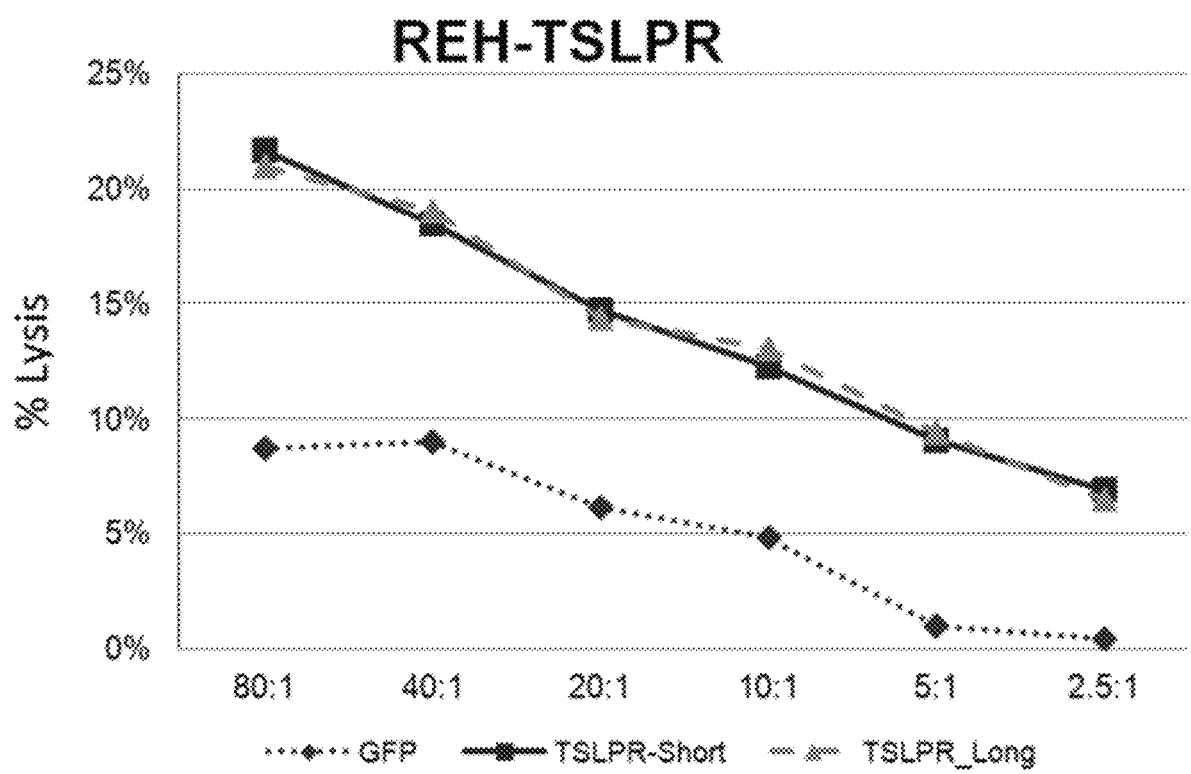
Figure 9D:
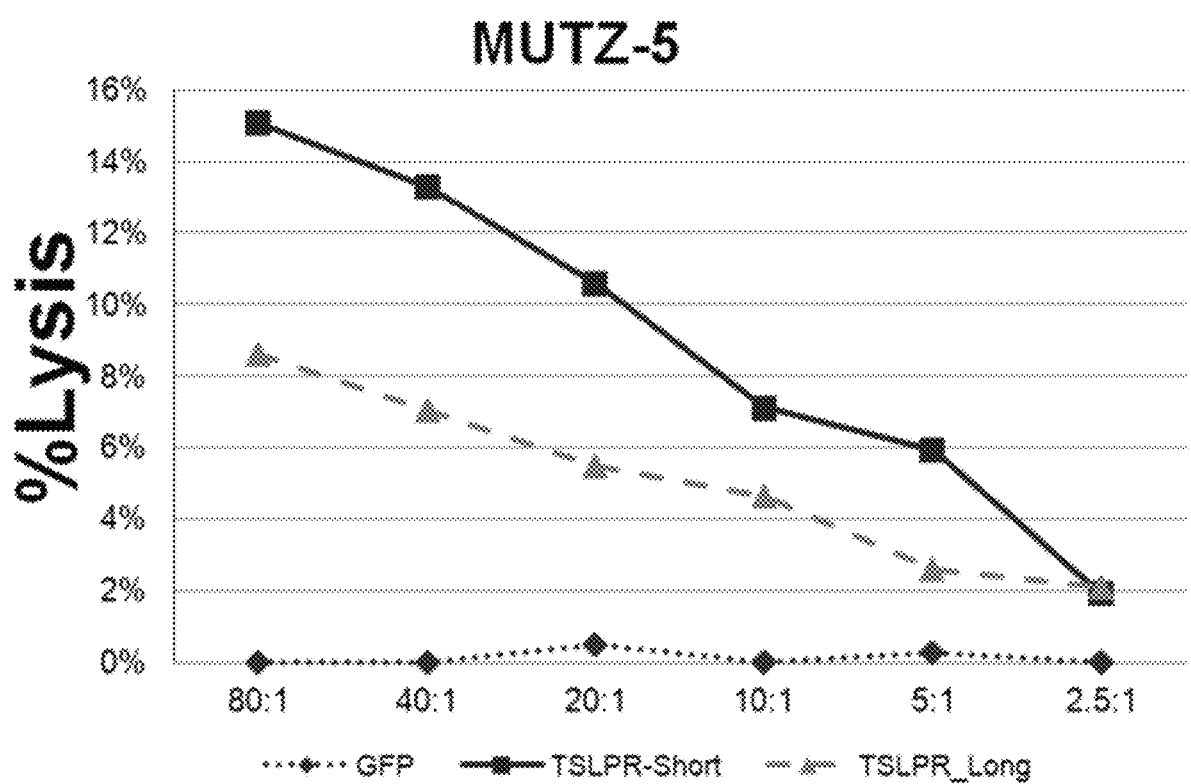

Testing was performed to determine whether T cells transduced with the TSLPR CAR constructs demonstrate activity against the pre B ALL cell line REH transduced to express TSLPR (REH-TSLPR) as well as a naturally TSLPR over-expressing ALL line (MUTZ5). As shown in FIG. 6, both short and long CAR T cells produce high levels of interferon gamma (IFNγ) and tumor necrosis factor alpha (TNFα) when incubated with REH-TSLPR. In addition, T cells with TSLPR CAR produce a broad range of inflammatory cytokines in the presence of both TSLPR-transduced and naturally overexpressing ALL cells (FIGS. 7A-7H and 8A-8E). When the lytic capacity of TSLPR CAR T cells was measured, the short and long constructs demonstrated equivalent activity against REH-TSLPR. However, the short TSLPR CAR mediated greater lysis of MUTZ5 than the long CAR despite comparable levels of TSLPR on both REH-TSLPR and MUTZ5 (FIGS. 2 and 9A-D).

Figure 10:
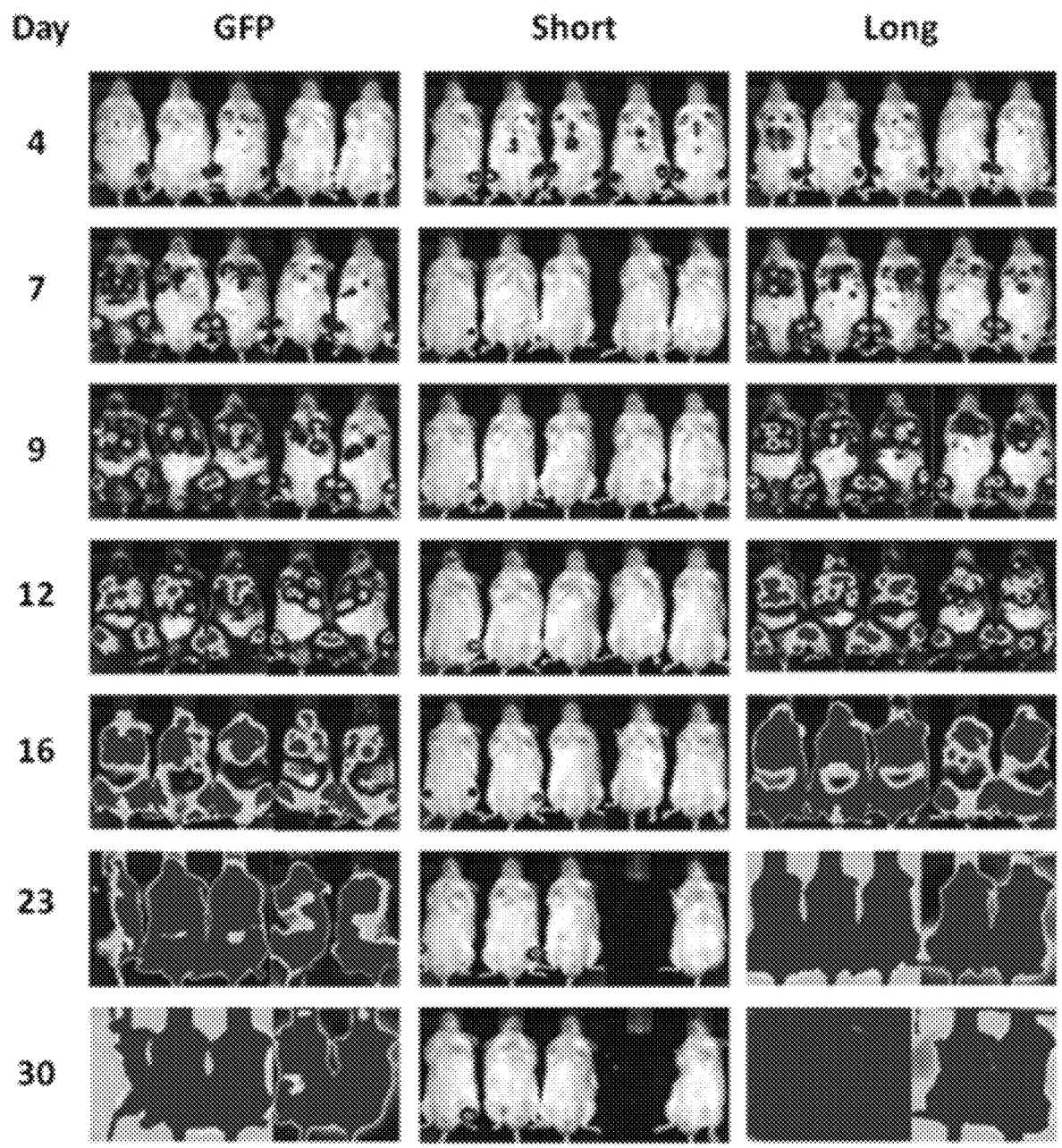
FIG. 10 shows images of leukemia reduction in vivo with short TSLPR CARs in accordance with certain embodiments of the present invention. Day 0: 5E5 cells REH-TSLPR, Day 4: 15E6 cells CAR T. The fourth animal in the short CAR column at Day 23 and Day 30 is not shown since the animal died due to a wasting syndrome consistent with xenographic graph versus host disease.
Figure 11:
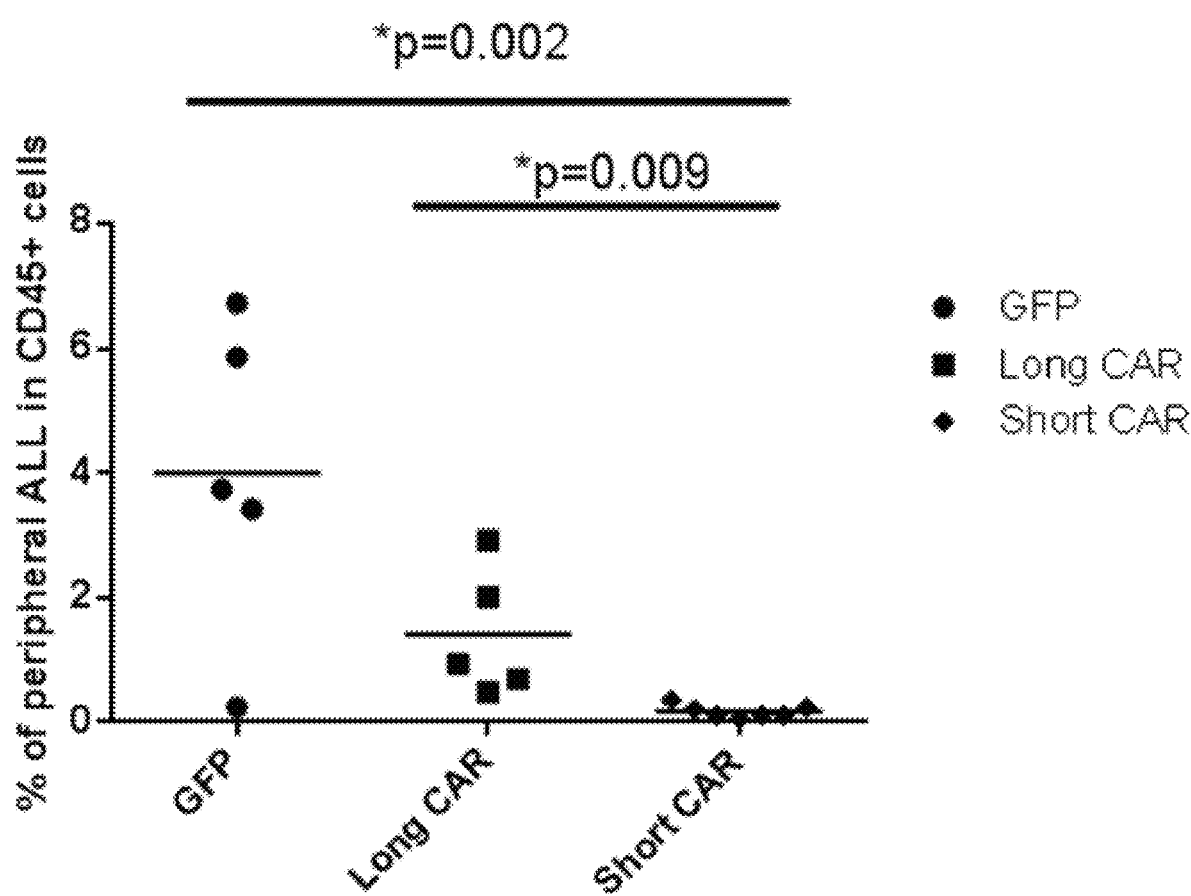
FIG. 11 is a dot plot showing comparison of the ALL in blood with the treatment of T cells transduced with different types of constructs in accordance with certain embodiments of the present invention. Peripheral ALL Burden on day 27 Post ADT (adoptive transfer).
Figure 12A:
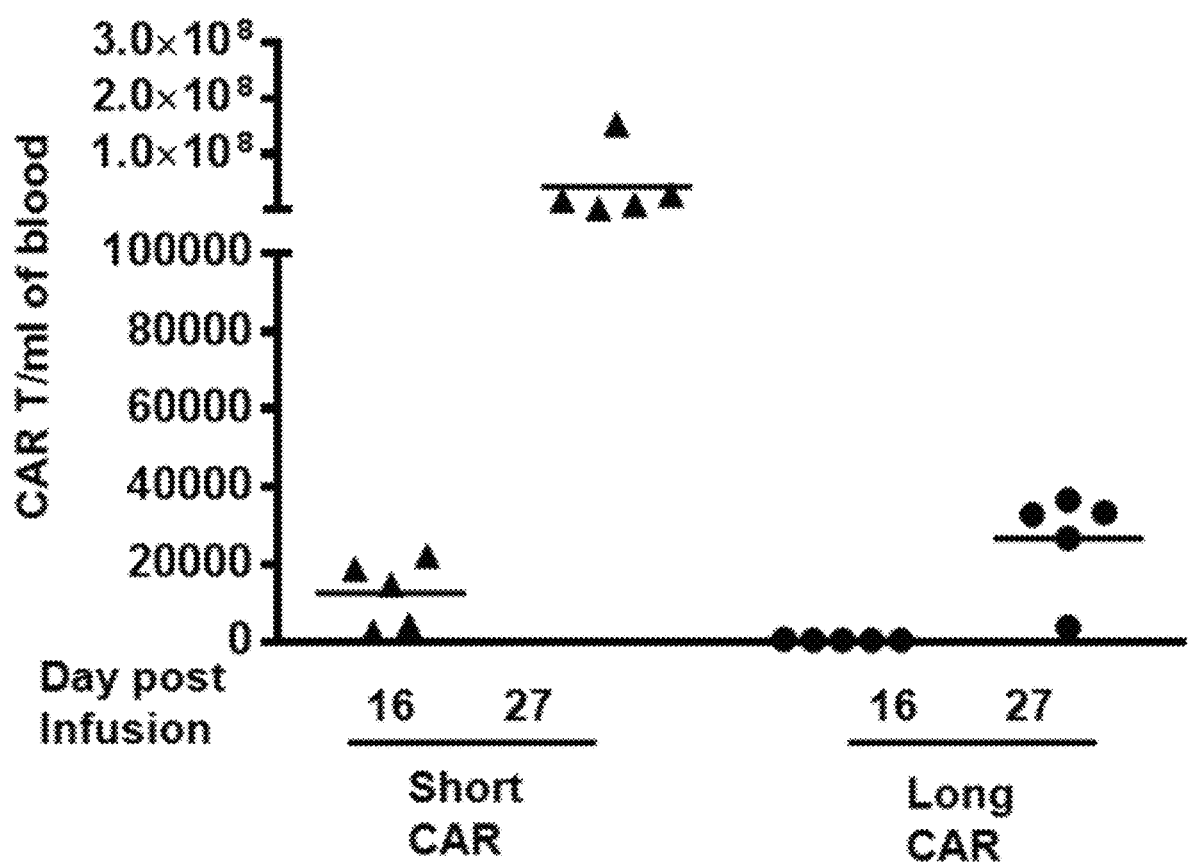
FIG. 12A is a dot plot showing percentage and persistence of CART cells in vivo post adoptive transfer in accordance with certain embodiments of the present invention. p=0.0008 for short CAR day 27 and long CAR days 16 and 27. There is evidence for increased numbers of short CAR T cells on day 16, although this is not significant.
Figure 12B:
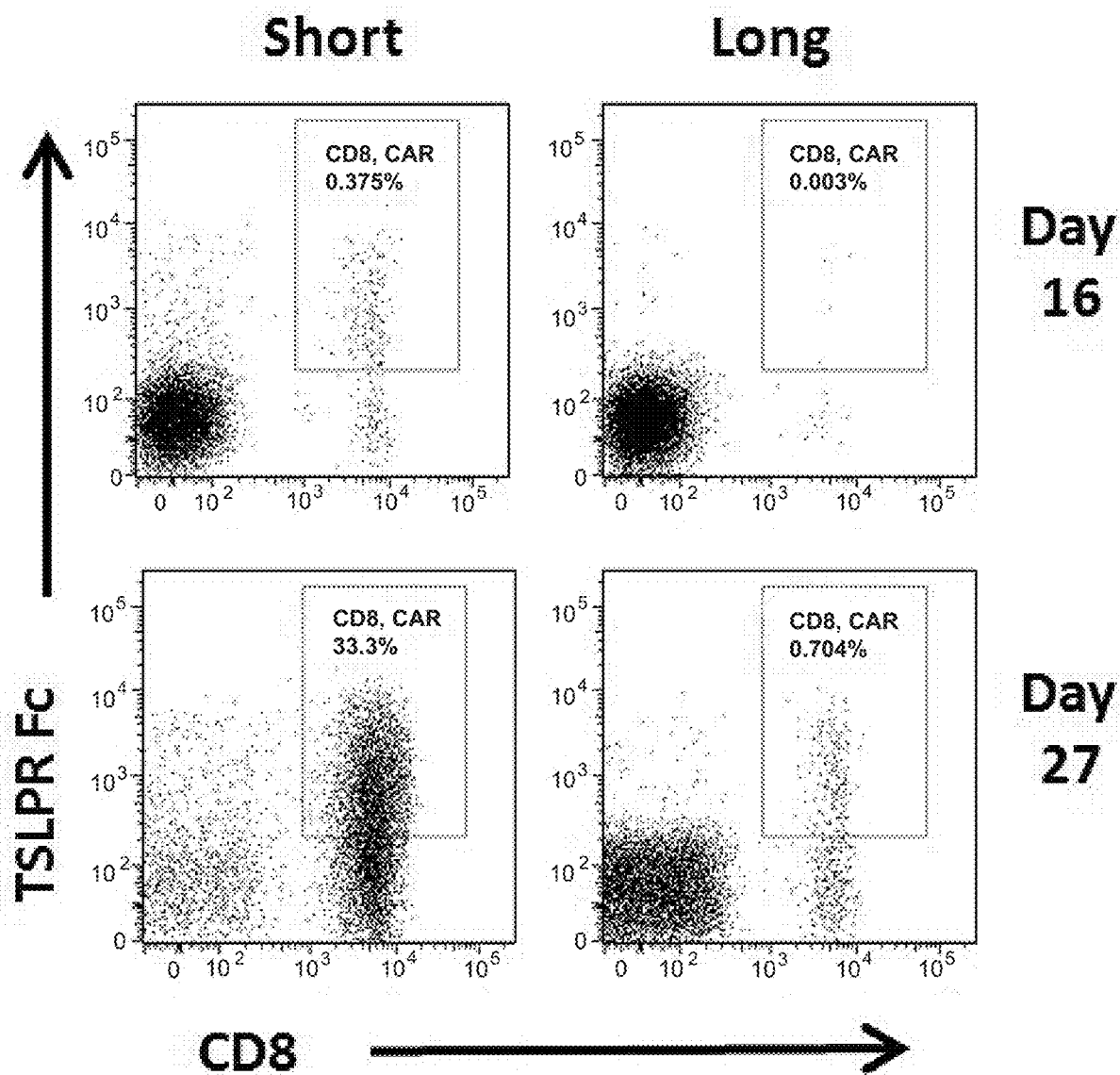
FIG. 12B is a dot plot of flow analysis displaying a typical quantity of CAR T cells in blood in accordance with certain embodiments of the present invention.

The ability for TSLPR CAR T cells to reduce ALL when infused into mice bearing TSLPR-overexpressing ALL was tested next. Four days after IV injection of luciferase-expressing REH-TSLPR, leukemia was detectable at low levels. Injection of 15×10$^6$ short CART cells appeared to completely reduce ALL assessed by imaging (FIG. 10) and by flow cytometry of peripheral blood for the presence of CD45+/GFP+ cells at day 12 following leukemia injection. (FIG. 11). Interestingly, despite equivalent in vitro activity against REH-TSLPR, long CAR T cells had minimal impact on leukemia progression in mice assessed by imaging with some evidence for reduced leukemic burden in peripheral blood when compared to mice receiving GFP-transduced T cells (albeit not statistically different). To determine the reason for the disparate activity of the long and short CAR constructs CAR T cell persistence by flow cytometry were investigated, and it was found that short CAR T cells were present in greater numbers in the peripheral blood compared to long CAR T cells (FIGS. 12A-B). FIG. 12B shows TSLPR Fc v. CD8. CAR T v. CD45 showed the following results: on Day 16, the short CART cells were at 3.02% (CD45 subset of 5.36%) and the long CAR T cells were at 0.038% (CD45 subset 0.213%), on Day 27, the short CAR T cells were at 44.1% (CD45 subset of 89.4%) and the long CART cells were at 2.14% (CD45 subset 7.54%). Interestingly, the presence in greater numbers in the peripheral blood of short CAR T cells was most notable at later time points despite progression of ALL that maintained expression of TSLPR in mice receiving long TSLPR CAR T cells. Thus, the marked increase in activity seen with the short TSLPR CAR construct compared to the long construct was associated with greater persistence of short CAR-expressing T cells.

Figure 13:
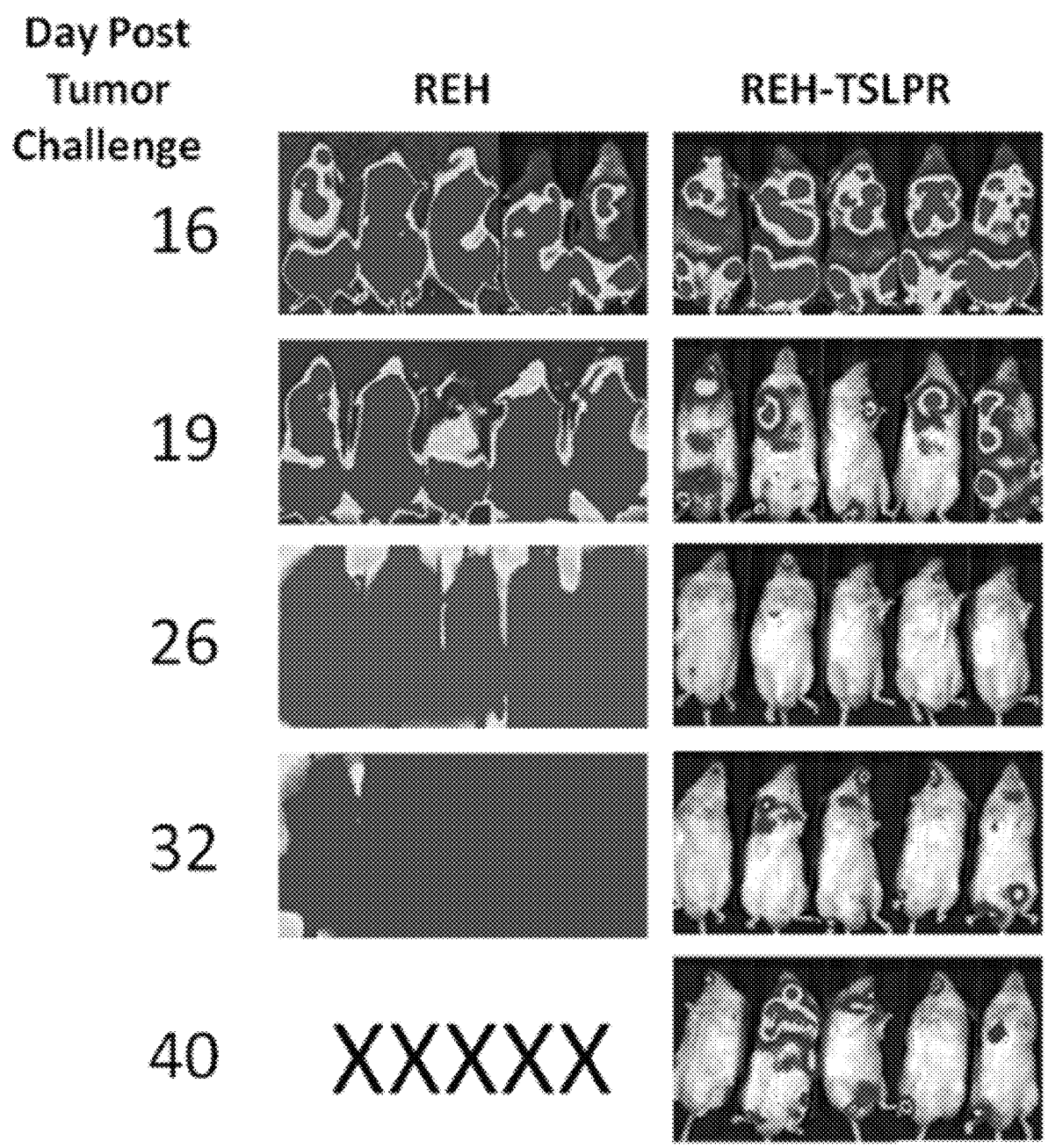
FIG. 13 presents images showing that reduction of leukemia in vivo with TSLPR CAR is target specific in accordance with certain embodiments of the present invention. On day 0: 1E6 tumor cells; on day 16: treated with 10E6 cells short CAR.
Figure 14:
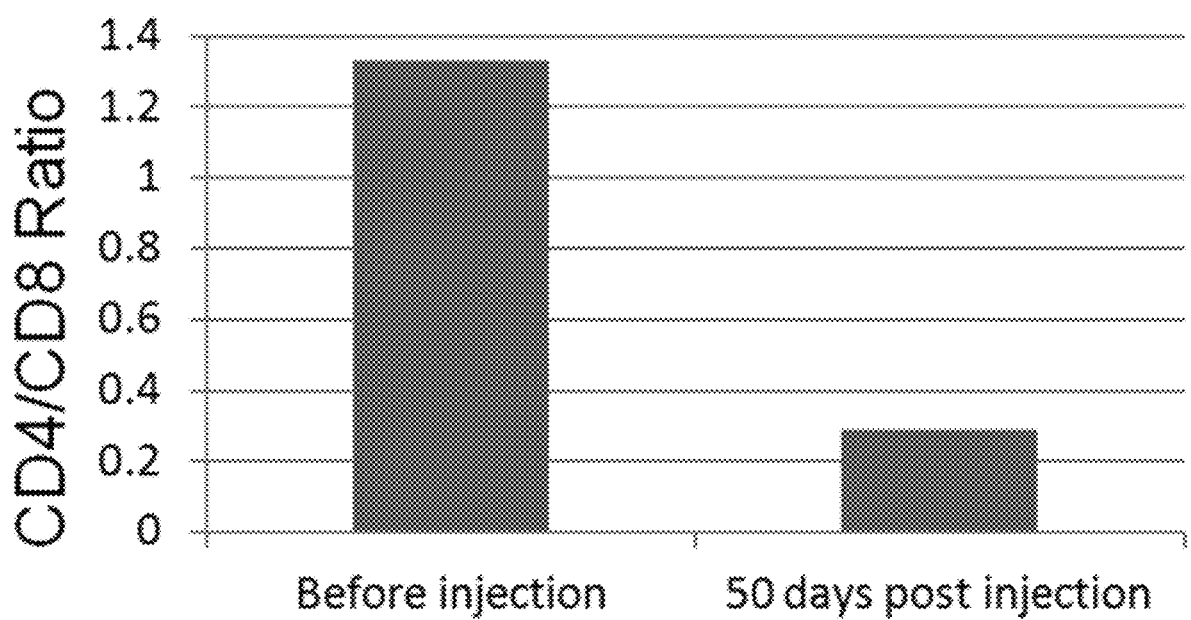
FIG. 14 is a bar graph showing TSLPR CAR transduced T cells are skewed to CD8 post ADT (on day 50) in accordance with certain embodiments of the present invention. The slightly increased relative number of CD4+ CAR T cells following CD3/CD28 bead-mediated expansion prior to infusion converts to a predominance of CD8+/TSLPR CAR+ (measured by TSLPR Fc) at day 50 following injection.
Figure 15:
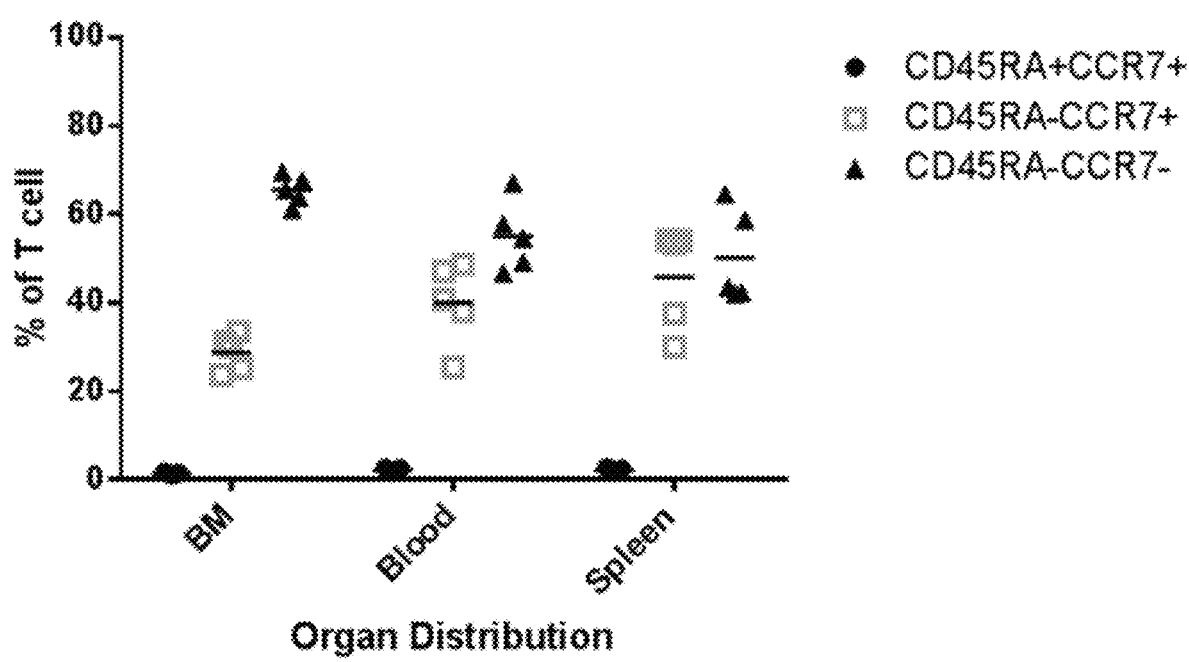
FIG. 15 is a dot plot showing the physical distribution of the TSLPR CAR in accordance with certain embodiments of the present invention. CD45RA+CCR7+ are naive, CD45RA−CCR7+ are central memory, and CD45RA+CCR7− are effector memory phenotypes of the T cells.

To test the short TSLPR CAR T cells in more established leukemia, infusion was delayed until day 16 after REH-TSLPR injection (FIG. 13). Remarkably, 10×10$^6$ short TSLPR CAR T cells were still able to induce rapid clearance of TSLPRhi ALL that was maintained in the majority of mice through day 40 (FIG. 13). Importantly, there was no evidence for any alteration in the progression of TSLPR when not over-expressed ("TSLPRlo ALL") by TSLPR CAR T cells demonstrating that activity is dependent on expression of the CAR target. Analysis of the relapses in mice treated with the short TSLPR CAR T cells demonstrated retained expression of CD19, CD10 and TSLPR indicating that failure is not due to loss of antigen. CD8+ T cells generally exhibit greater in vitro lytic function and are thought to be important mediators of direct anti-tumor activity in vivo when compared to CD4+ T cells. Interestingly, although the in vitro expansion protocol utilized in these experiments resulted in a predominance of CD4+ T cells prior to infusion, by day 50, CD8+ T cells expanded markedly and represented the largest T cell subset in vivo (FIG. 14). This expansion of CD8+ CAR-expressing T cells was associated with expression of surface markers associated with effector phenotypes by day 50 (FIG. 15, showing the physical distribution of the TSLPR CAR). There were also a substantial percentage of CAR T cells with a CCR7+/CD45RA phenotype, consistent with central memory subset, thought to be important for persistence and sustained anti-tumor activity.

Figure 16A:
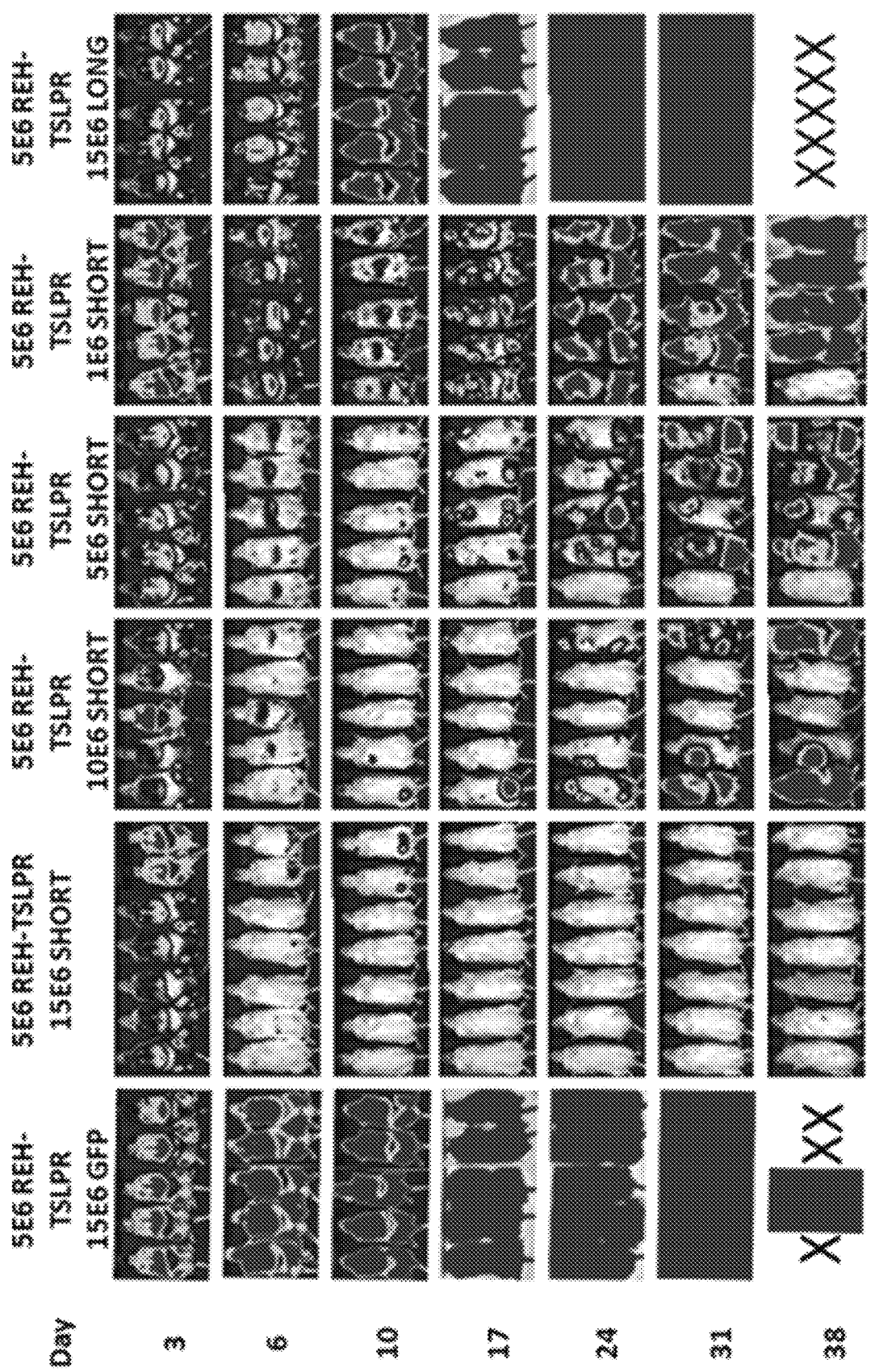
FIG. 16A presents bioluminescent images tracking leukemia progression with different treatments in vivo in accordance with certain embodiments of the present invention.
Figure 16B:
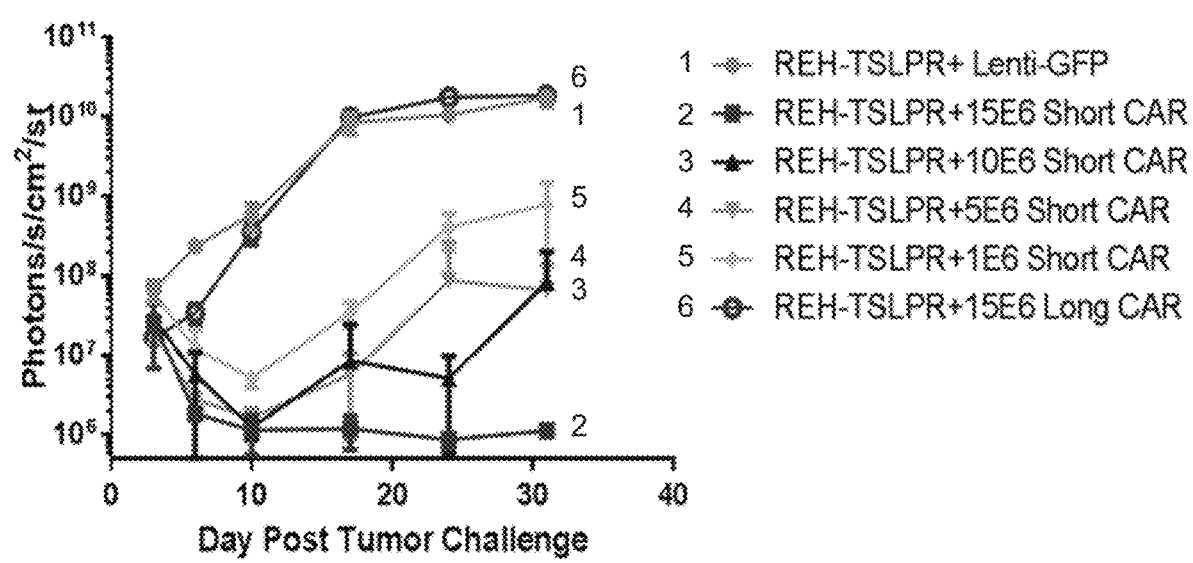
FIG. 16B is a line graph showing quantitation of leukemia progression in accordance with certain embodiments of the present invention.
Figure 16C:
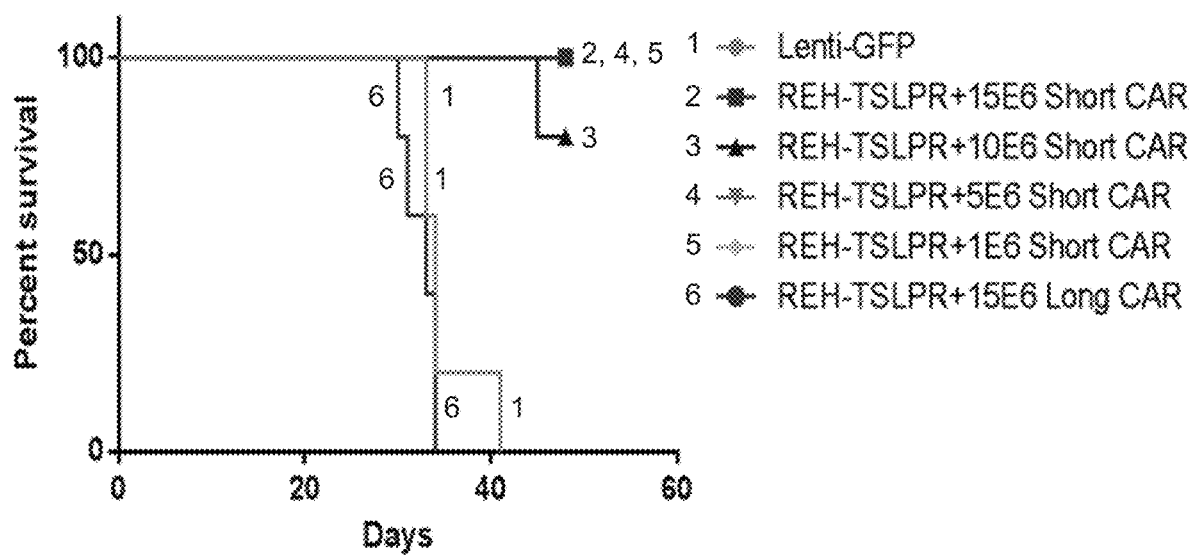
FIG. 16C is a line graph showing a survival plot of TSLPR CAR treatment in accordance with certain embodiments of the present invention.

An in vivo short CAR T cell dose titration was performed to define the range over which activity is observed and whether short TSLPR could reduce established leukemia. As shown in FIGS. 16A-C, short TSLPR CAR cells at 15×10$^6$ cells per mouse greatly reduced ALL with clear activity at 5-10×10$^6$ per mouse and some activity as low as 1×10$^6$ per mouse, particularly noted as improved survival (FIG. 16C). Again, there was minimal activity seen following infusion of the long CAR T cells with only a slight decrease in leukemic burden in the peripheral blood (FIG. 11) and luciferase activity at day 6 (FIG. 16B) compared to GFP T cells but no difference between the two groups at any of the later time points consistent with the failure of the long CAR T cells to persist.

Figure 17:
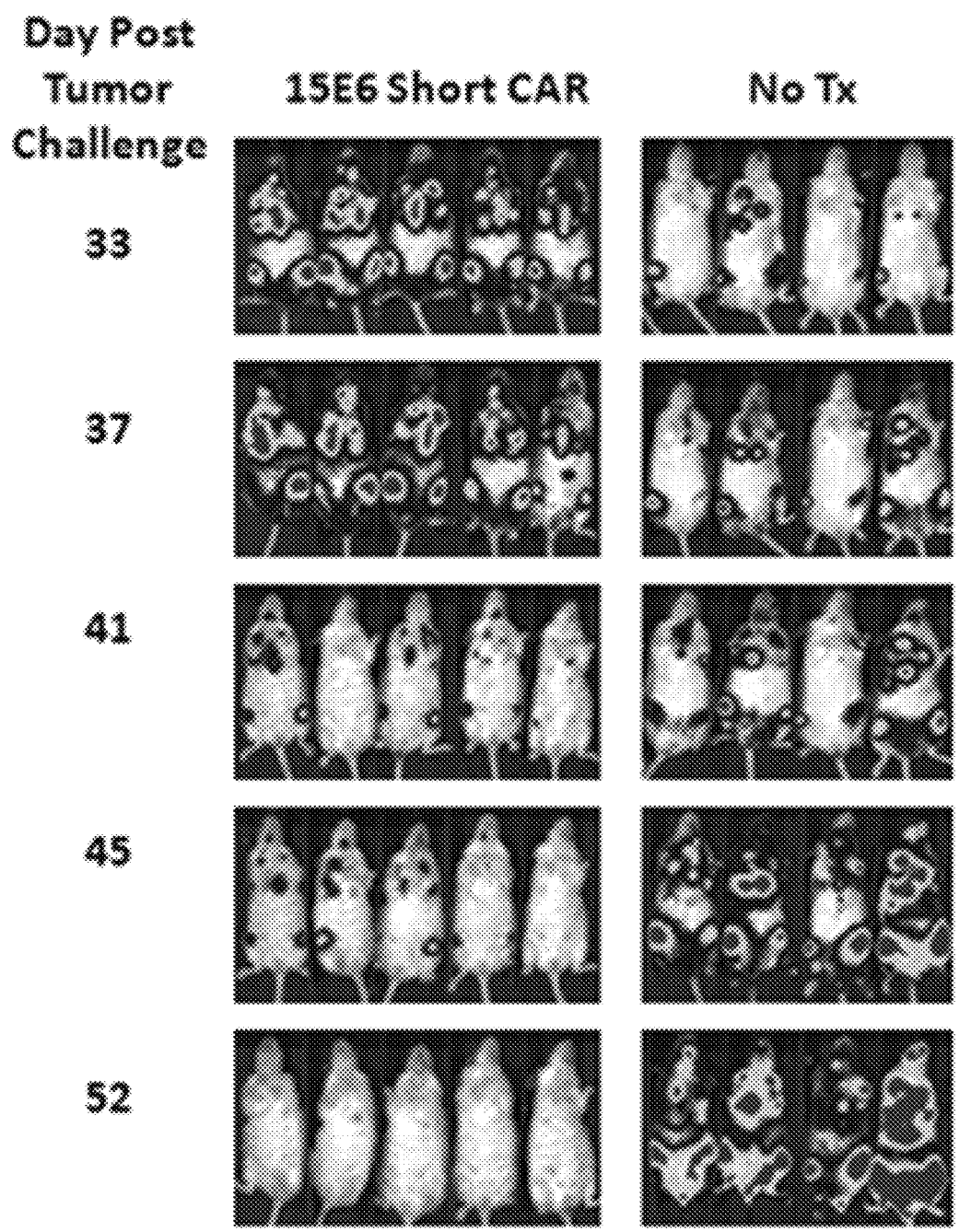
FIG. 17 presents images showing reduction of high burden in patient TSLPRhi xenografts using TSLPR short CAR in accordance with certain embodiments of the present invention.
Figure 18A:
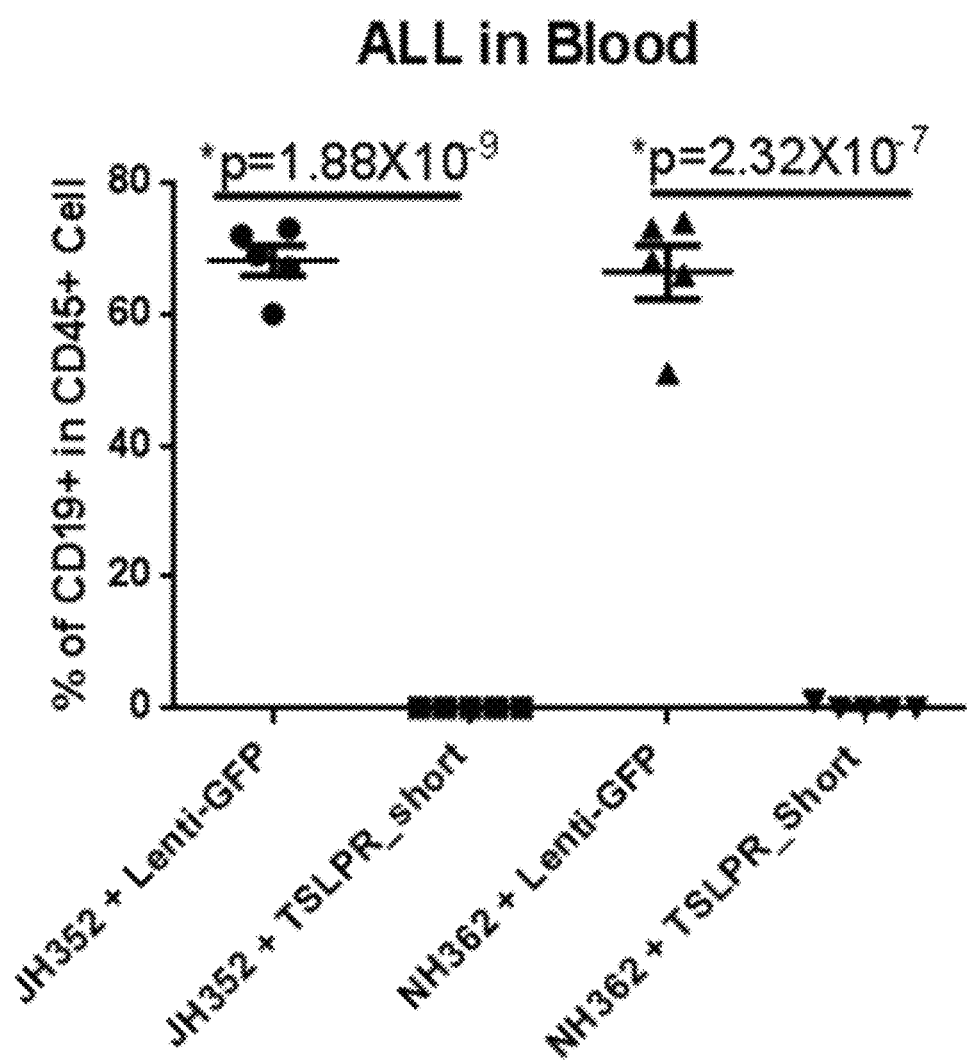
FIG. 18A is a dot plot showing analysis in blood of patient TSLPRhi xenografts 22 days post tumor challenge in accordance with certain embodiments of the present invention. 1E6 cells of JH352 or NH362 treated with 15E6 cells TSLPR-short CART cell or Lenti-GFP T cell in NSG mice.
Figure 18B:
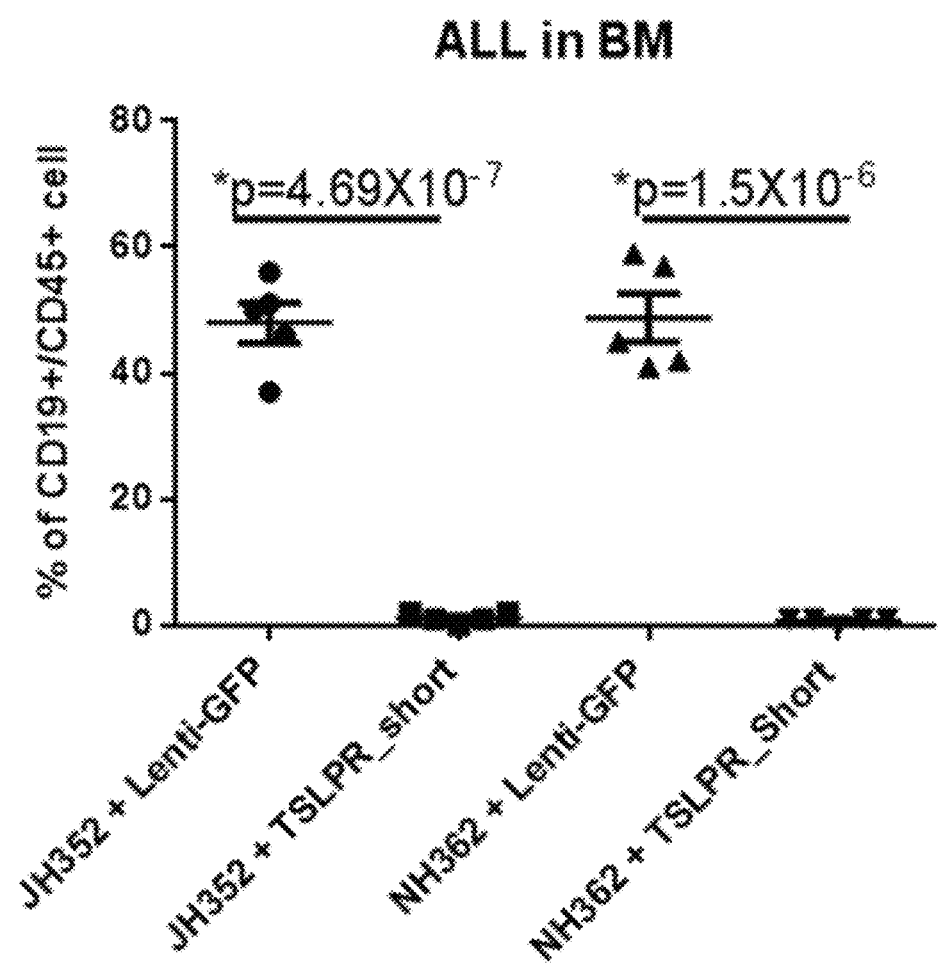
FIG. 18B is a dot plot showing analysis in bone marrow of patient TSLPRhi xenografts 22 days post tumor challenge in accordance with certain embodiments of the present invention. 1E6 of JH352 or NH362 treated with 15E6 TSLPR-short CART cell or Lenti-GFP T cell in NSG mice.

The short TSLPR construct was tested in 3 xenograft models of pre-B cell ALL that naturally overexpress TSLPR. As shown in FIG. 17, the short TSLPR CAR greatly reduced human ALL TSLPRhi xenograft expressing luciferase. The Short TSLPR CAR also greatly reduced additional TSLPRhi xenografts from both the blood and bone marrow of mice (FIGS. 18A and 18B).

Figure 19:
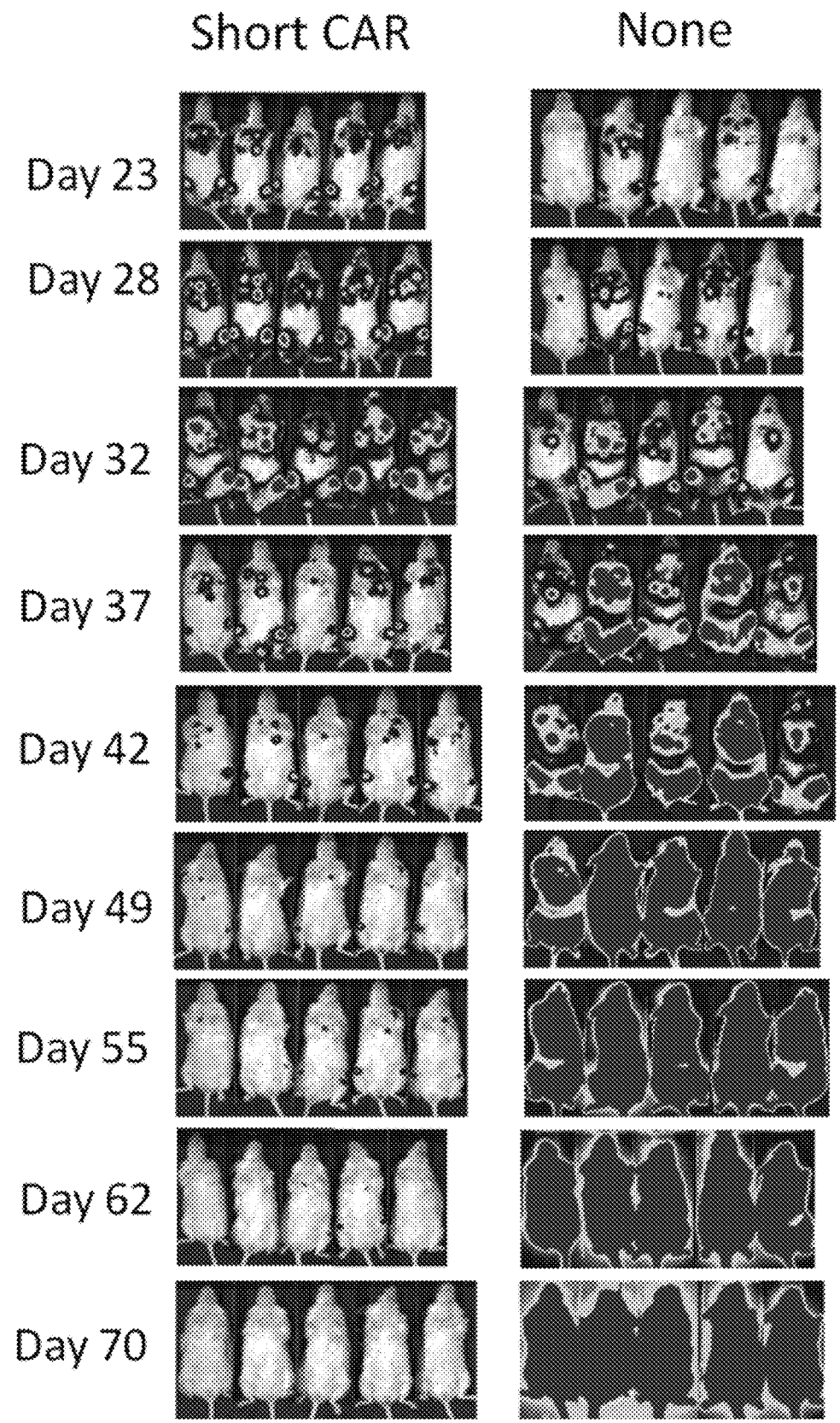
FIG. 19 presents images showing treatment of Patient JH331-Luc with 1.2E6 Short TSLPR CAR where the short TSLPR CAR can reduce ALL in patient xerographs with as low as 1.2 million of CART cells in accordance with certain embodiments of the present invention.
Figure 20:
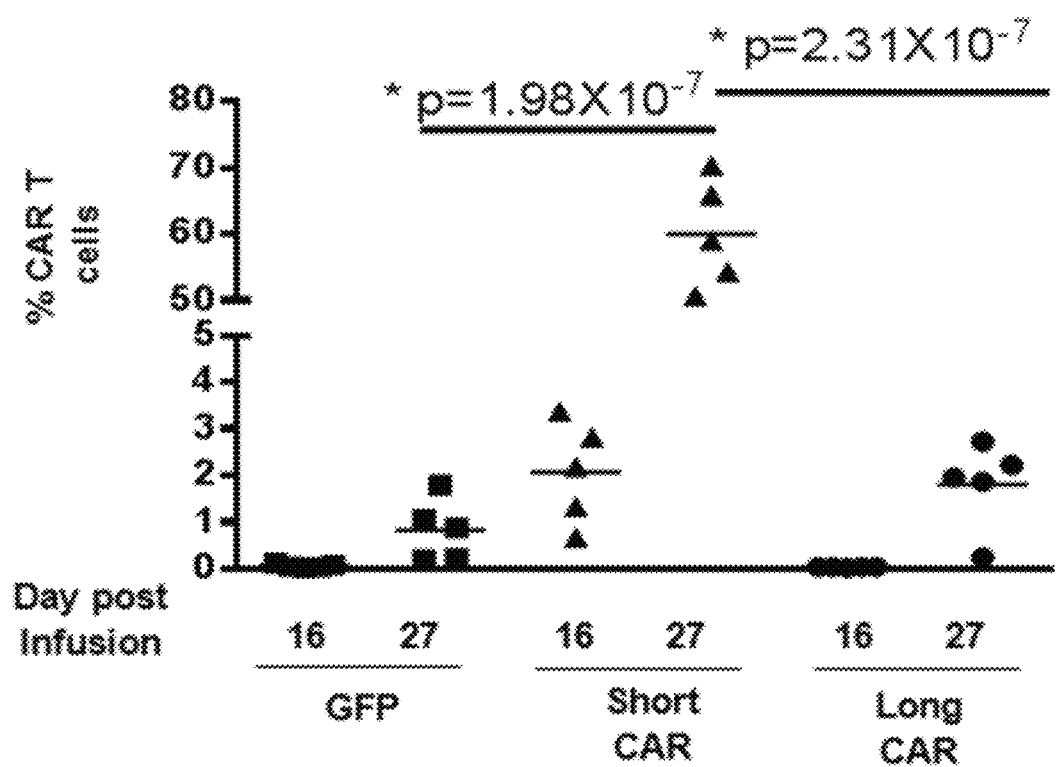
FIG. 20 is a dot plot showing the percentage of CAR T cells presented in mouse blood sample in accordance with certain embodiments of the present invention.
Figure 21:
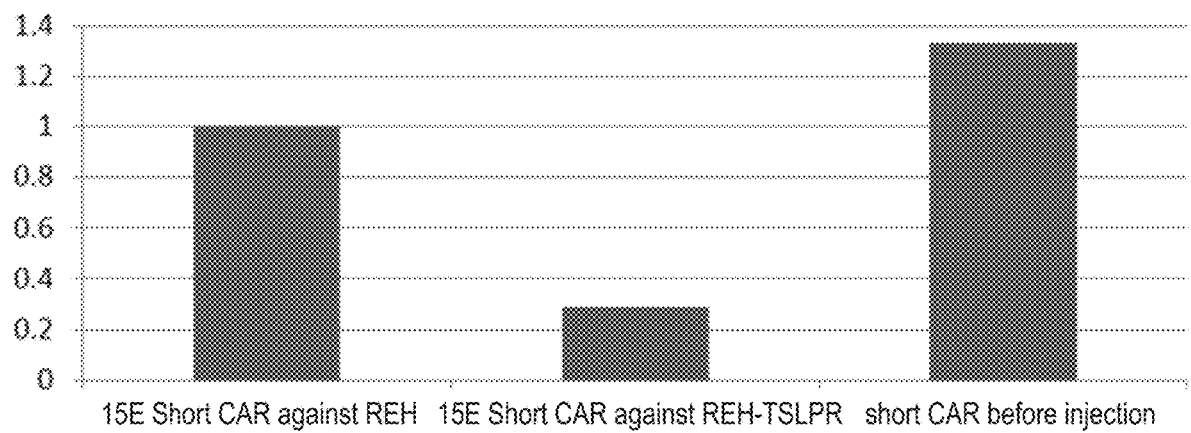
FIG. 21 is a bar graph showing the shift of the CD4 to CD8 of CAR T cells after injection in vivo in accordance with certain embodiments of the present invention.
Figure 22:
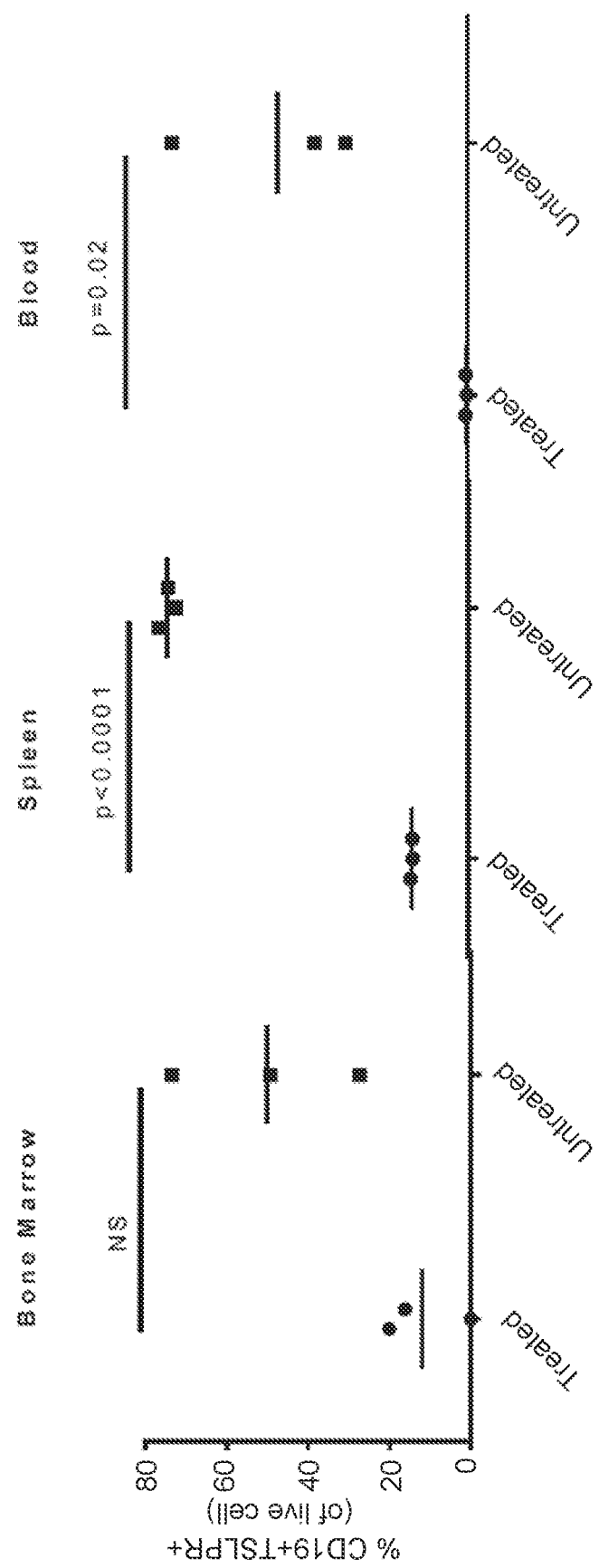
FIG. 22 is a representative dot plot on day 35 following leukemia injection in accordance with certain embodiments of the present invention.
Figure 23:
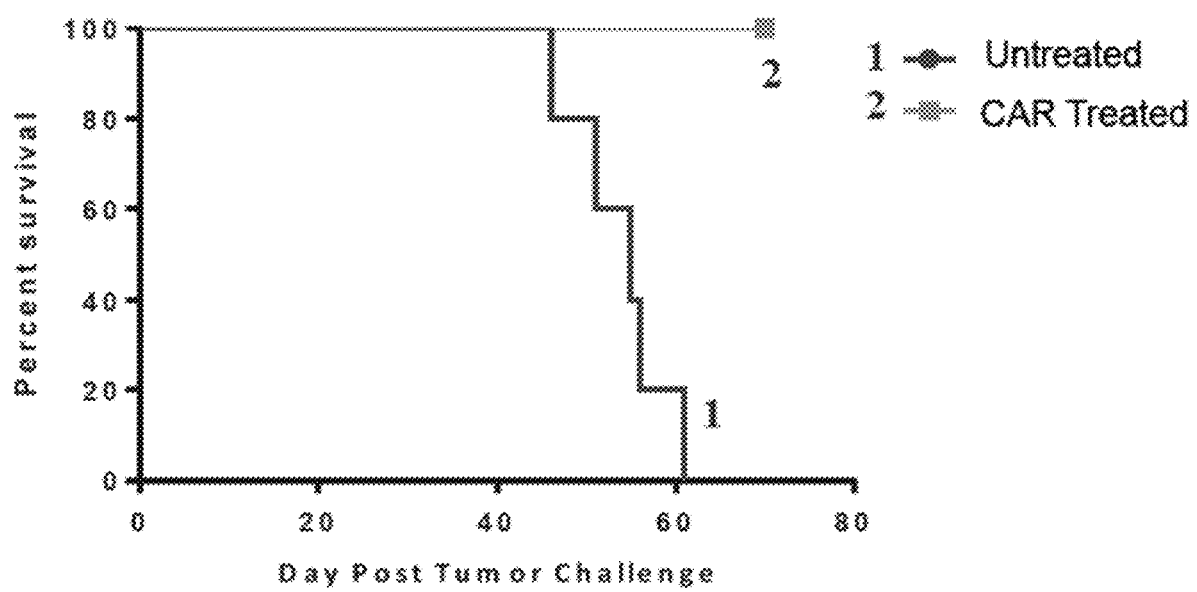
FIG. 23 is a line plot showing survival following injection of aggressive TSLPRhi ALL into NSG mice with and without TSLPR CAT treatment ($2\times10^6$/mouse) on day 18 (n=5/group) in accordance with certain embodiments of the present invention.

FIG. 19 shows the short TSLPR CAR can reduce ALL in patient xerographs with as low as 1.2 million of CART cells. FIG. 20 is a dot plot showing the percentage of CAR T cells presented in mouse blood sample. FIG. 21 shows the shift of the CD4 to CD8 of the CAR T cells after injected in vivo.

The short TSLPR CAR was tested against an aggressive TSLPR ALL that results in lethality by 60 days after IV injection in NSG mice. One million aggressive TSLPRhi ALL cells were injected in NSG mice intravenously on day 1 then treated with 1.2 million TSLPR CAR+ T cells on day 14. The short TSLPR CAR demonstrated potent activity (FIGS. 22-25), resulting in reduction in splenomegaly and reduction in blast counts in the spleen and blood as early as day 14 following CAR injection. Interestingly, although there appeared to be activity in the bone marrow as well, the clearance of leukemia was less rapid and not statistically significant at this early evaluation time. However, CAR treatment was associated with eventual clearance of aggressive TSLPRhi ALL and prolonged survival.

Figure 24:
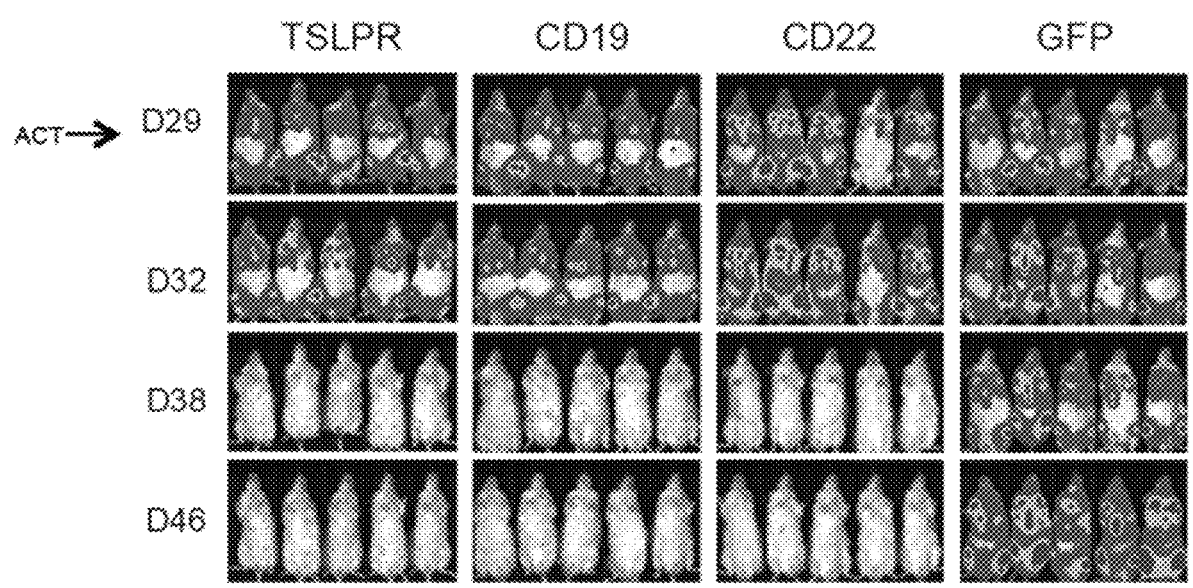
FIG. 24 presents images showing results based on CAR+ T cells (3E6) of TSLPR, CD19, and CD22 injected into NSG mice engrafted with the patient xenograph cell line JH331-LUC for 29 days, in accordance with certain embodiments of the present invention. T cells transduced with GFP were used as a negative control.

The activity of the short TSLPR CAR activity was compared to that of a CD19 CAR containing the same scFv (FM68 scFv-CD8-CD137-CD3zeta) and a CD22 CAR construct (m971 scFv-CD8-CD137-CD3zeta). All had the same 41BB costimulatory domain and resulted in comparable transduction efficiencies. The short TSLPR CAR was comparable to both the CD19 and CD22 CARs at reducing the JHH331 Luc TSLPRhi xenograph (FIG. 24).

Example 2

This example demonstrates the testing of two additional TSLPR CARs (Short 2D10 (SEQ ID NOS: 41 and 45) and Long 2D10 (SEQ ID NOS: 42 and 46)) and comparison to the CARs of Example 1. The leader sequence is initially encoded and enhances trafficking to the cell surface. It is likely to be cleaved off in the mature form.

Methods of Example 1 were generally followed.

Figure 25A:
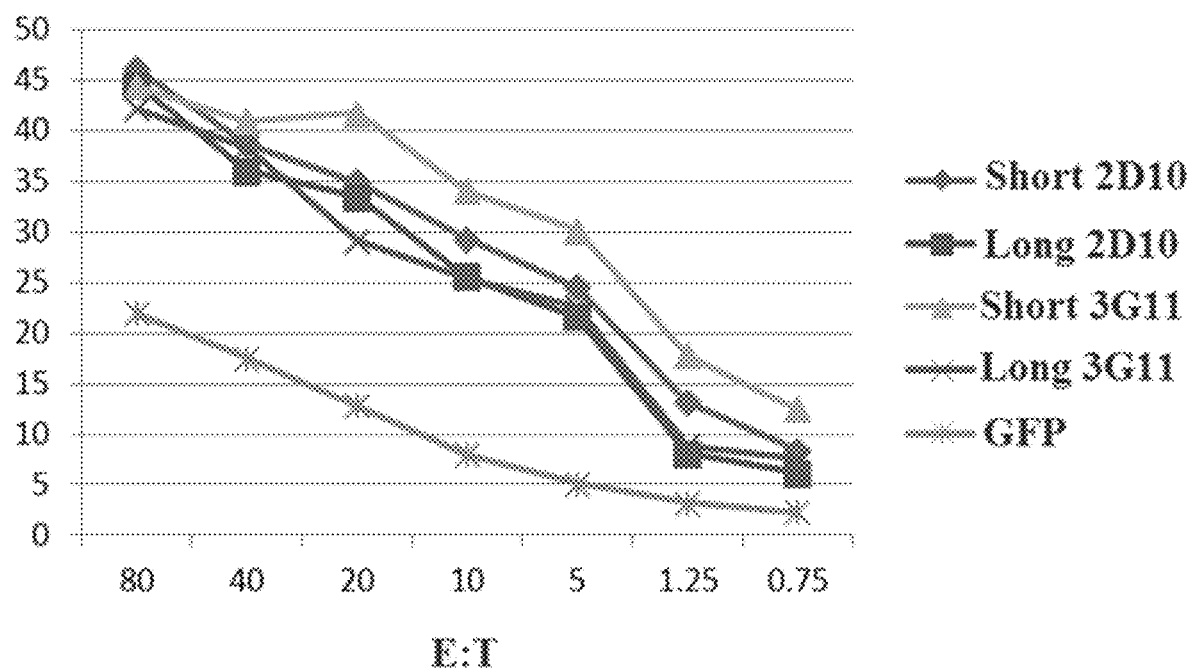
FIGS. 25A-C are line graphs showing percent lysis of tumor cells using CARs in accordance with certain embodiments of the present invention.
Figure 25B:
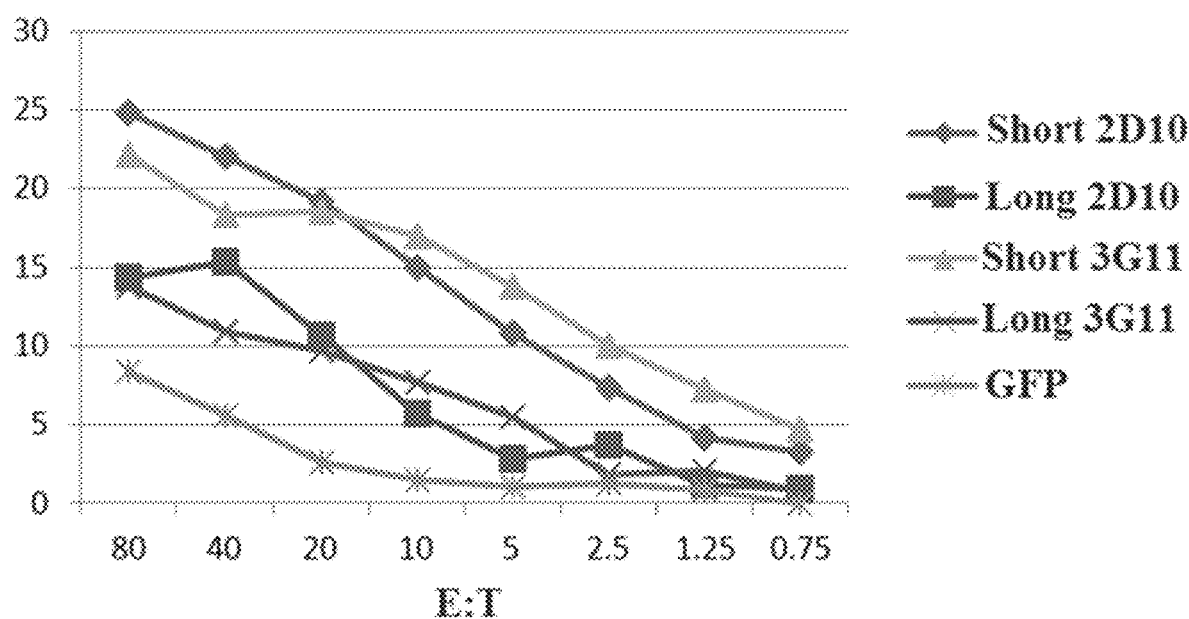
Figure 25C:
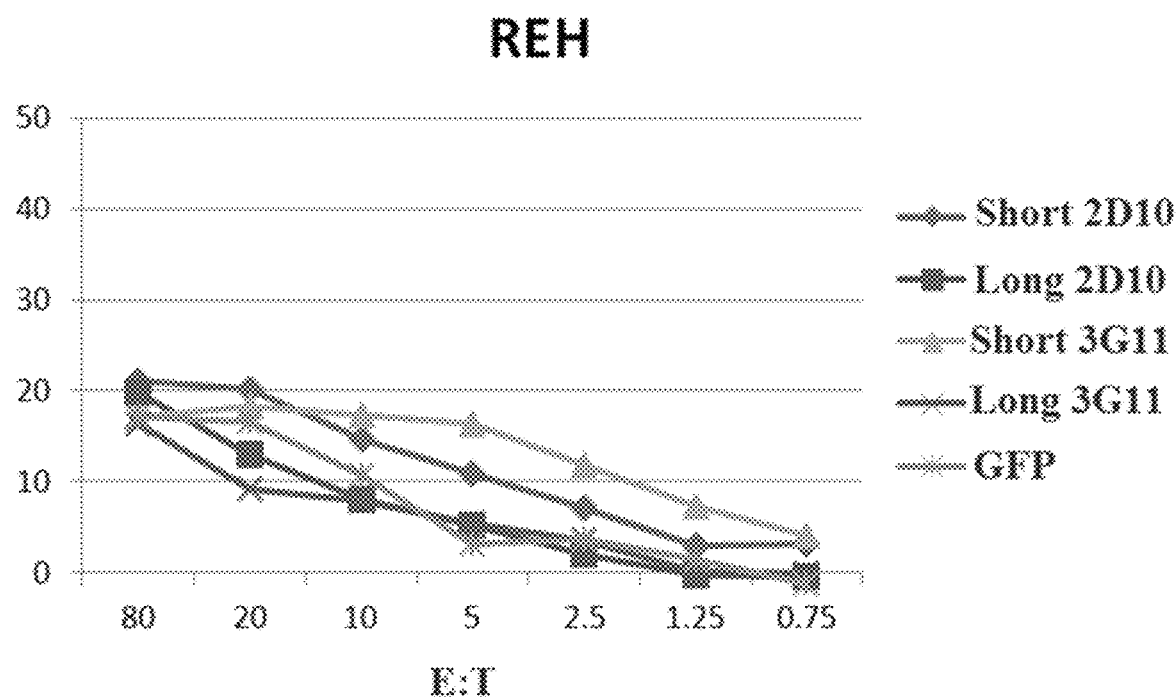
Figure 26:
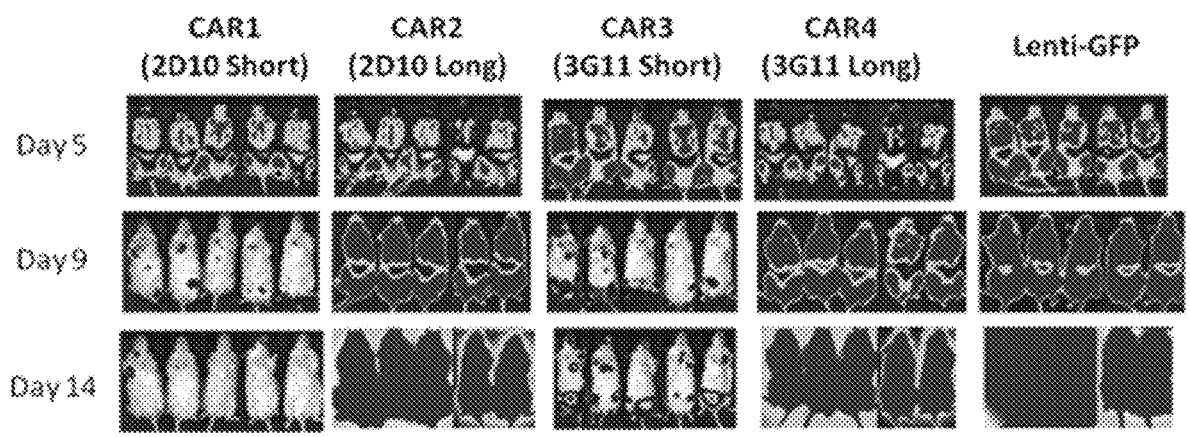
FIG. 26 presents images showing therapeutic function of the different CAR constructs in vivo in accordance with certain embodiments of the present invention.

FIGS. 25A-C and 26 present the results. FIGS. 25A-C show the cytolytic functions of the transduced T cells with different TSLPR CAR constructs when incubated with TSLPR expression leukemia cell lines, where the REH was served as a negative expression line. FIG. 26 shows therapeutic function of the different CAR constructs in vivo.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Also, everywhere "comprising" (or its equivalent) is recited, the "comprising" is considered to incorporate "consisting essentially of" and "consisting of." Thus, an embodiment "comprising" (an) element(s) supports embodiments "consisting essentially of" and "consisting of" the recited element(s). Everywhere "consisting essentially of" is recited is considered to incorporate "consisting of." Thus, an embodiment "consisting essentially of" (an) element(s) supports embodiments "consisting of" the recited element(s). Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of detecting the presence of a thymic stromal lymphopoietin receptor (TSLPR)-overexpressing acute lymphoblastic leukemia (ALL), comprising:
   (a) contacting a sample comprising one or more ALL cells with a chimeric antigen receptor (CAR) comprising an antigen binding domain specific for TSLPR, a transmembrane domain, and an intracellular T cell signaling domain, wherein the antigen binding domain comprises (a) the light chain variable region CDR sequences of (i) SEQ ID NOS: 20, 24, and 27 or (ii) SEQ ID NOS: 21, 24, and 28, and (b) the heavy chain variable region CDR sequences of (i) SEQ ID NOS: 7, 10, and 13 or (ii) SEQ ID NOS: 8, 10, and 14, thereby forming a complex, and
   (b) detecting the complex, wherein detection of the complex is indicative of the presence of TSLPR-overexpressing ALL.

2. The method of claim 1, wherein the TSLPR-overexpressing ALL is B cell precursor (BCP)-ALL.

3. A method of determining whether a subject with an acute lymphoblastic leukemia (ALL) is a candidate for treatment with a chimeric antigen receptor (CAR) comprising an antigen binding domain specific for thymic stromal lymphopoietin receptor (TSLPR), the method comprising: measuring TSLPR expression levels in an ALL cell from the subject; and determining if the TSLPR expression levels of the ALL cell are increased compared to a sample from a control subject without an ALL, wherein the CAR comprises an antigen binding domain specific for TSLPR, a transmembrane domain, and an intracellular T cell signaling domain, and wherein the antigen binding domain comprises (a) the light chain variable region CDR sequences of (i) SEQ ID NOS: 20, 24, and 27 or (ii) SEQ ID NOS: 21, 24, and 28, and (b) the heavy chain variable region CDR sequences of (i) SEQ ID NOS: 7, 10, and 13 or (ii) SEQ ID NOS: 8, 10, and 14.

4. A method of treating a thymic stromal lymphopoietin receptor (TSLPR)-overexpressing acute lymphoblastic leukemia (ALL) in a mammal, the method comprising administering to the mammal an effective amount of a T-cell comprising a chimeric antigen receptor (CAR) to treat the ALL in the mammal, wherein the CAR comprises an antigen binding domain specific for TSLPR, a transmembrane domain, and an intracellular T cell signaling domain, and wherein the antigen binding domain comprises (a) the light chain variable region CDR sequences of (i) SEQ ID NOS: 20, 24, and 27 or (ii) SEQ ID NOS: 21, 24, and 28, and (b) the heavy chain variable region CDR sequences of (i) SEQ ID NOS: 7, 10, and 13 or (ii) SEQ ID NOS: 8, 10, and 14.

5. The method of claim 4, wherein the ALL is B cell precursor (BCP)-ALL.

6. The method of claim 4, wherein the ALL is associated with a mutation in the IKZF gene.

7. The method of claim 1, wherein the antigen binding domain comprises the light chain variable region CDR sequences of SEQ ID NOS: 20, 24, and 27 and the heavy chain variable region CDR sequences of SEQ ID NOS: 7, 10, and 13.

8. The method of claim 1, wherein the antigen binding domain comprises the light chain variable region CDR sequences of SEQ ID NOS: 21, 24, and 28 and the heavy chain variable region CDR sequences of SEQ ID NOS: 8, 10, and 14.

9. The method of claim 1, wherein the CAR comprises any one of the sequences of SEQ ID NO: 39-46.

10. The method of claim 1, wherein the CAR comprises the sequence of SEQ ID NO: 39.

11. The method of claim 3, wherein the antigen binding domain comprises the light chain variable region CDR sequences of SEQ ID NOS: 20, 24, and 27 and the heavy chain variable region CDR sequences of SEQ ID NOS: 7, 10, and 13.

12. The method of claim 3, wherein the antigen binding domain comprises the light chain variable region CDR sequences of SEQ ID NOS: 21, 24, and 28 and the heavy chain variable region CDR sequences of SEQ ID NOS: 8, 10, and 14.

13. The method of claim 3, wherein the CAR comprises any one of the sequences of SEQ ID NO: 39-46.

14. The method of claim 3, wherein the CAR comprises the sequence of SEQ ID NO: 39.

15. The method of claim 4, wherein the antigen binding domain comprises the light chain variable region CDR sequences of SEQ ID NOS: 20, 24, and 27 and the heavy chain variable region CDR sequences of SEQ ID NOS: 7, 10, and 13.

16. The method of claim 4, wherein the antigen binding domain comprises the light chain variable region CDR sequences of SEQ ID NOS: 21, 24, and 28 and the heavy chain variable region CDR sequences of SEQ ID NOS: 8, 10, and 14.

17. The method of claim 4, wherein the CAR comprises any one of the sequences of SEQ ID NO: 39-46.

18. The method of claim 4, wherein the CAR comprises the sequence of SEQ ID NO: 39.

19. The method of claim 6, wherein the antigen binding domain comprises the light chain variable region CDR sequences of SEQ ID NOS: 20, 24, and 27 and the heavy chain variable region CDR sequences of SEQ ID NOS: 7, 10, and 13.

20. The method of claim 6, wherein the antigen binding domain comprises the light chain variable region CDR sequences of SEQ ID NOS: 21, 24, and 28 and the heavy chain variable region CDR sequences of SEQ ID NOS: 8, 10, and 14.

21. The method of claim 6, wherein the CAR comprises any one of the sequences of SEQ ID NO: 39-46.

22. The method of claim 6, wherein the CAR comprises the sequence of SEQ ID NO: 39.

* * * * *

SEQUENCE LISTING

<160> NUMBER OF SEQ ID NOS: 46

<210> SEQ ID NO 1
<211> LENGTH: 243
<212> TYPE: PRT
<213> ORGANISM: Artificial Sequence
<220> FEATURE:
<223> OTHER INFORMATION: Synthetic

<400> SEQUENCE: 1

Gln Val Thr Leu Lys Glu Ser Gly Pro Gly Ile Leu Lys Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp Asp Asp Lys Tyr Tyr Asn Pro Ser
    50                  55                  60

Leu Lys Ser Gln Leu Thr Ile Ser Lys Asp Thr Ser Arg Asn Gln Val
65                  70                  75                  80

Phe Leu Lys Ile Thr Ser Val Asp Thr Ala Asp Thr Ala Thr Tyr Tyr
                85                  90                  95

Cys Ser Arg Arg Pro Arg Gly Thr Met Asp Ala Met Asp Tyr Trp Gly
                100                 105                 110

Gln Gly Thr Ser Val Thr Val Ser Ser Gly Gly Gly Ser Gly Gly
                115                 120                 125

Gly Gly Ser Gly Gly Gly Ser Asp Ile Val Met Thr Gln Ala Ala
        130                 135                 140

Ser Ser Leu Ser Ala Ser Leu Gly Asp Arg Val Thr Ile Ser Cys Arg
145                 150                 155                 160

Ala Ser Gln Asp Ile Ser Lys Tyr Leu Asn Trp Tyr Gln Gln Lys Pro
                165                 170                 175

Asp Gly Thr Val Lys Leu Leu Ile Tyr Tyr Thr Ser Arg Leu His Ser
                180                 185                 190

Gly Val Pro Ser Arg Phe Ser Gly Ser Gly Ser Gly Thr Asp Tyr Ser
                195                 200                 205

Leu Thr Ile Arg Asn Leu Glu Gln Glu Asp Ile Ala Thr Tyr Phe Cys
    210                 215                 220

Gln Gln Val Tyr Thr Leu Pro Trp Thr Phe Gly Gly Gly Thr Lys Leu
225                 230                 235                 240

Glu Ile Lys

<210> SEQ ID NO 2
<211> LENGTH: 245
<212> TYPE: PRT
<213> ORGANISM: Artificial Sequence
<220> FEATURE:
<223> OTHER INFORMATION: Synthetic

<400> SEQUENCE: 2

Gln Val Thr Leu Lys Glu Ser Gly Pro Gly Ile Leu Lys Pro Ser Gln
1               5                   10                  15

Thr Leu Ser Leu Thr Cys Ser Phe Ser Gly Phe Ser Leu Asn Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp Asp Asp Lys Tyr Tyr Asn Pro Ser
    50                  55                  60

Leu Lys Ser Gln Leu Thr Ile Ser Lys Asp Thr Ser Arg Asn Gln Val
65                  70                  75                  80

Phe Leu Lys Ile Thr Ser Val Asp Thr Ala Asp Ser Ala Thr Tyr Tyr
                85                  90                  95

Cys Ala Arg Arg Ala Ser His Val Ser Thr Val Asp Ser Phe Asp Phe
                100                 105                 110

```
Trp Gly Gln Gly Thr Thr Leu Thr Val Ser Ser Gly Gly Gly Ser
            115                 120                 125

Gly Gly Gly Gly Ser Gly Gly Gly Ser Asp Ile Gln Met Thr Gln
        130                 135                 140

Thr Thr Ser Ser Leu Ser Ala Ser Leu Gly Asp Arg Val Thr Ile Ser
145                 150                 155                 160

Cys Arg Ala Ser Gln Asp Ile Ser Asn Tyr Leu Asn Trp Phe Gln Gln
                165                 170                 175

Lys Pro Asp Gly Thr Val Lys Leu Leu Ile Tyr Tyr Thr Ser Arg Leu
            180                 185                 190

His Ser Gly Val Pro Ser Lys Phe Ser Gly Ser Gly Ser Gly Thr Asp
        195                 200                 205

Tyr Ser Leu Thr Ile Ser Asn Leu Glu Gln Glu Asp Ile Ala Thr Tyr
    210                 215                 220

Phe Cys Gln Gln Gly Tyr Thr Leu Pro Trp Thr Phe Gly Gly Gly Thr
225                 230                 235                 240

Lys Leu Glu Ile Lys
            245

<210> SEQ ID NO 3
<211> LENGTH: 4
<212> TYPE: PRT
<213> ORGANISM: Artificial Sequence
<220> FEATURE:
<223> OTHER INFORMATION: Synthetic

<400> SEQUENCE: 3

Ala Ser Ala Thr
1

<210> SEQ ID NO 4
<211> LENGTH: 1
<212> TYPE: PRT
<213> ORGANISM: Artificial Sequence
<220> FEATURE:
<223> OTHER INFORMATION: Synthetic

<400> SEQUENCE: 4

Met
1

<210> SEQ ID NO 5
<211> LENGTH: 20
<212> TYPE: PRT
<213> ORGANISM: Artificial Sequence
<220> FEATURE:
<223> OTHER INFORMATION: Synthetic

<400> SEQUENCE: 5

Ala Leu Pro Val Thr Ala Leu Leu Leu Pro Leu Ala Leu Leu Leu His
1               5                   10                  15

Ala Ala Arg Pro
            20

<210> SEQ ID NO 6
<211> LENGTH: 25
<212> TYPE: PRT
<213> ORGANISM: Artificial Sequence
<220> FEATURE:
<223> OTHER INFORMATION: Synthetic

<400> SEQUENCE: 6
```

-continued

```
Gln Val Thr Leu Lys Glu Ser Gly Pro Gly Ile Leu Lys Pro Ser Gln
1               5                   10                  15

Thr Leu Ser Leu Thr Cys Ser Phe Ser
            20                  25

<210> SEQ ID NO 7
<211> LENGTH: 10
<212> TYPE: PRT
<213> ORGANISM: Artificial Sequence
<220> FEATURE:
<223> OTHER INFORMATION: Synthetic

<400> SEQUENCE: 7

Gly Phe Ser Leu Ser Thr Ser Gly Met Gly
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Synthetic

<400> SEQUENCE: 8

Gly Phe Ser Leu Asn Thr Ser Gly Met Gly
1               5                   10

<210> SEQ ID NO 9
<211> LENGTH: 17
<212> TYPE: PRT
<213> ORGANISM: Artificial Sequence
<220> FEATURE:
<223> OTHER INFORMATION: Synthetic

<400> SEQUENCE: 9

Val Gly Trp Ile Arg Gln Pro Ser Gly Lys Gly Leu Glu Trp Leu Ala
1               5                   10                  15

His

<210> SEQ ID NO 10
<211> LENGTH: 7
<212> TYPE: PRT
<213> ORGANISM: Artificial Sequence
<220> FEATURE:
<223> OTHER INFORMATION: Synthetic

<400> SEQUENCE: 10

Ile Trp Trp Asp Asp Asp Lys
1               5

<210> SEQ ID NO 11
<211> LENGTH: 38
<212> TYPE: PRT
<213> ORGANISM: Artificial Sequence
<220> FEATURE:
<223> OTHER INFORMATION: Synthetic

<400> SEQUENCE: 11

Tyr Tyr Asn Pro Ser Leu Lys Ser Gln Leu Thr Ile Ser Lys Asp Thr
1               5                   10                  15

Ser Arg Asn Gln Val Phe Leu Lys Ile Thr Ser Val Asp Thr Ala Asp
            20                  25                  30

Thr Ala Thr Tyr Tyr Cys
        35
```

<210> SEQ ID NO 12
<211> LENGTH: 38
<212> TYPE: PRT
<213> ORGANISM: Artificial Sequence
<220> FEATURE:
<223> OTHER INFORMATION: Synthetic

<400> SEQUENCE: 12

Tyr Tyr Asn Pro Ser Leu Lys Ser Gln Leu Thr Ile Ser Lys Asp Thr
1               5                   10                  15

Ser Arg Asn Gln Val Phe Leu Lys Ile Thr Ser Val Asp Thr Ala Asp
            20                  25                  30

Ser Ala Thr Tyr Tyr Cys
        35

<210> SEQ ID NO 13
<211> LENGTH: 13
<212> TYPE: PRT
<213> ORGANISM: Artificial Sequence
<220> FEATURE:
<223> OTHER INFORMATION: Synthetic

<400> SEQUENCE: 13

Ser Arg Arg Pro Arg Gly Thr Met Asp Ala Met Asp Tyr
1               5                   10

<210> SEQ ID NO 14
<211> LENGTH: 15
<212> TYPE: PRT
<213> ORGANISM: Artificial Sequence
<220> FEATURE:
<223> OTHER INFORMATION: Synthetic

<400> SEQUENCE: 14

Ala Arg Arg Ala Ser His Val Ser Thr Val Asp Ser Phe Asp Phe
1               5                   10                  15

<210> SEQ ID NO 15
<211> LENGTH: 11
<212> TYPE: PRT
<213> ORGANISM: Artificial Sequence
<220> FEATURE:
<223> OTHER INFORMATION: Synthetic

<400> SEQUENCE: 15

Trp Gly Gln Gly Thr Ser Val Thr Val Ser Ser
1               5                   10

<210> SEQ ID NO 16
<211> LENGTH: 11
<212> TYPE: PRT
<213> ORGANISM: Artificial Sequence
<220> FEATURE:
<223> OTHER INFORMATION: Synthetic

<400> SEQUENCE: 16

Trp Gly Gln Gly Thr Thr Leu Thr Val Ser Ser
1               5                   10

<210> SEQ ID NO 17
<211> LENGTH: 15
<212> TYPE: PRT
<213> ORGANISM: Artificial Sequence
<220> FEATURE:
<223> OTHER INFORMATION: Synthetic

```
<400> SEQUENCE: 17

Gly Gly Gly Gly Ser Gly Gly Gly Ser Gly Gly Gly Ser
1               5                   10                  15

<210> SEQ ID NO 18
<211> LENGTH: 26
<212> TYPE: PRT
<213> ORGANISM: Artificial Sequence
<220> FEATURE:
<223> OTHER INFORMATION: Synthetic

<400> SEQUENCE: 18

Asp Ile Val Met Thr Gln Ala Ala Ser Ser Leu Ser Ala Ser Leu Gly
1               5                   10                  15

Asp Arg Val Thr Ile Ser Cys Arg Ala Ser
            20                  25

<210> SEQ ID NO 19
<211> LENGTH: 26
<212> TYPE: PRT
<213> ORGANISM: Artificial Sequence
<220> FEATURE:
<223> OTHER INFORMATION: Synthetic

<400> SEQUENCE: 19

Asp Ile Gln Met Thr Gln Thr Thr Ser Ser Leu Ser Ala Ser Leu Gly
1               5                   10                  15

Asp Arg Val Thr Ile Ser Cys Arg Ala Ser
            20                  25

<210> SEQ ID NO 20
<211> LENGTH: 6
<212> TYPE: PRT
<213> ORGANISM: Artificial Sequence
<220> FEATURE:
<223> OTHER INFORMATION: Synthetic

<400> SEQUENCE: 20

Gln Asp Ile Ser Lys Tyr
1               5

<210> SEQ ID NO 21
<211> LENGTH: 6
<212> TYPE: PRT
<213> ORGANISM: Artificial Sequence
<220> FEATURE:
<223> OTHER INFORMATION: Synthetic

<400> SEQUENCE: 21

Gln Asp Ile Ser Asn Tyr
1               5

<210> SEQ ID NO 22
<211> LENGTH: 17
<212> TYPE: PRT
<213> ORGANISM: Artificial Sequence
<220> FEATURE:
<223> OTHER INFORMATION: Synthetic

<400> SEQUENCE: 22

Leu Asn Trp Tyr Gln Gln Lys Pro Asp Gly Thr Val Lys Leu Leu Ile
1               5                   10                  15

Tyr
```

-continued

```
<210> SEQ ID NO 23
<211> LENGTH: 17
<212> TYPE: PRT
<213> ORGANISM: Artificial Sequence
<220> FEATURE:
<223> OTHER INFORMATION: Synthetic

<400> SEQUENCE: 23

Leu Asn Trp Phe Gln Gln Lys Pro Asp Gly Thr Val Lys Leu Leu Ile
1               5                   10                  15

Tyr

<210> SEQ ID NO 24
<211> LENGTH: 3
<212> TYPE: PRT
<213> ORGANISM: Artificial Sequence
<220> FEATURE:
<223> OTHER INFORMATION: Synthetic

<400> SEQUENCE: 24

Tyr Thr Ser
1

<210> SEQ ID NO 25
<211> LENGTH: 36
<212> TYPE: PRT
<213> ORGANISM: Artificial Sequence
<220> FEATURE:
<223> OTHER INFORMATION: Synthetic

<400> SEQUENCE: 25

Arg Leu His Ser Gly Val Pro Ser Arg Phe Ser Gly Ser Gly Ser Gly
1               5                   10                  15

Thr Asp Tyr Ser Leu Thr Ile Arg Asn Leu Glu Gln Glu Asp Ile Ala
            20                  25                  30

Thr Tyr Phe Cys
        35

<210> SEQ ID NO 26
<211> LENGTH: 36
<212> TYPE: PRT
<213> ORGANISM: Artificial Sequence
<220> FEATURE:
<223> OTHER INFORMATION: Synthetic

<400> SEQUENCE: 26

Arg Leu His Ser Gly Val Pro Ser Lys Phe Ser Gly Ser Gly Ser Gly
1               5                   10                  15

Thr Asp Tyr Ser Leu Thr Ile Ser Asn Leu Glu Gln Glu Asp Ile Ala
            20                  25                  30

Thr Tyr Phe Cys
        35

<210> SEQ ID NO 27
<211> LENGTH: 9
<212> TYPE: PRT
<213> ORGANISM: Artificial Sequence
<220> FEATURE:
<223> OTHER INFORMATION: Synthetic

<400> SEQUENCE: 27

Gln Gln Val Tyr Thr Leu Pro Trp Thr
1               5
```

```
<210> SEQ ID NO 28
<211> LENGTH: 9
<212> TYPE: PRT
<213> ORGANISM: Artificial Sequence
<220> FEATURE:
<223> OTHER INFORMATION: Synthetic

<400> SEQUENCE: 28

Gln Gln Gly Tyr Thr Leu Pro Trp Thr
1               5

<210> SEQ ID NO 29
<211> LENGTH: 10
<212> TYPE: PRT
<213> ORGANISM: Artificial Sequence
<220> FEATURE:
<223> OTHER INFORMATION: Synthetic

<400> SEQUENCE: 29

Phe Gly Gly Gly Thr Lys Leu Glu Ile Lys
1               5                   10

<210> SEQ ID NO 30
<211> LENGTH: 4
<212> TYPE: PRT
<213> ORGANISM: Artificial Sequence
<220> FEATURE:
<223> OTHER INFORMATION: Synthetic

<400> SEQUENCE: 30

Leu Glu Asp Pro
1

<210> SEQ ID NO 31
<211> LENGTH: 126
<212> TYPE: PRT
<213> ORGANISM: Artificial Sequence
<220> FEATURE:
<223> OTHER INFORMATION: Synthetic

<400> SEQUENCE: 31

Ala Glu Pro Lys Ser Pro Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys
        115                 120                 125

<210> SEQ ID NO 32
<211> LENGTH: 107
<212> TYPE: PRT
<213> ORGANISM: Artificial Sequence
<220> FEATURE:
<223> OTHER INFORMATION: Synthetic
```

<400> SEQUENCE: 32

```
Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105
```

<210> SEQ ID NO 33
<211> LENGTH: 4
<212> TYPE: PRT
<213> ORGANISM: Artificial Sequence
<220> FEATURE:
<223> OTHER INFORMATION: Synthetic

<400> SEQUENCE: 33

```
Lys Asp Pro Lys
1
```

<210> SEQ ID NO 34
<211> LENGTH: 2
<212> TYPE: PRT
<213> ORGANISM: Artificial Sequence
<220> FEATURE:
<223> OTHER INFORMATION: Synthetic

<400> SEQUENCE: 34

```
Ser Gly
1
```

<210> SEQ ID NO 35
<211> LENGTH: 45
<212> TYPE: PRT
<213> ORGANISM: Artificial Sequence
<220> FEATURE:
<223> OTHER INFORMATION: Synthetic

<400> SEQUENCE: 35

```
Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45
```

<210> SEQ ID NO 36
<211> LENGTH: 24
<212> TYPE: PRT
<213> ORGANISM: Artificial Sequence
<220> FEATURE:
<223> OTHER INFORMATION: Synthetic

<400> SEQUENCE: 36

```
Ile Tyr Ile Trp Ala Pro Leu Ala Gly Thr Cys Gly Val Leu Leu Leu
1               5                   10                  15

Ser Leu Val Ile Thr Leu Tyr Cys
            20
```

<210> SEQ ID NO 37
<211> LENGTH: 42
<212> TYPE: PRT
<213> ORGANISM: Artificial Sequence
<220> FEATURE:
<223> OTHER INFORMATION: Synthetic

<400> SEQUENCE: 37

```
Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
            35                  40
```

<210> SEQ ID NO 38
<211> LENGTH: 112
<212> TYPE: PRT
<213> ORGANISM: Artificial Sequence
<220> FEATURE:
<223> OTHER INFORMATION: Synthetic

<400> SEQUENCE: 38

```
Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
        50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
                100                 105                 110
```

<210> SEQ ID NO 39
<211> LENGTH: 489
<212> TYPE: PRT
<213> ORGANISM: Artificial Sequence
<220> FEATURE:
<223> OTHER INFORMATION: Synthetic

<400> SEQUENCE: 39

```
Met Ala Leu Pro Val Thr Ala Leu Leu Leu Pro Leu Ala Leu Leu Leu
1               5                   10                  15

His Ala Ala Arg Pro Gln Val Thr Leu Lys Glu Ser Gly Pro Gly Ile
            20                  25                  30

Leu Lys Pro Ser Gln Thr Leu Ser Leu Thr Cys Ser Phe Ser Gly Phe
            35                  40                  45

Ser Leu Ser Thr Ser Gly Met Gly Val Gly Trp Ile Arg Gln Pro Ser
        50                  55                  60

Gly Lys Gly Leu Glu Trp Leu Ala His Ile Trp Trp Asp Asp Asp Lys
```

-continued

```
            65                  70                  75                  80
Tyr Tyr Asn Pro Ser Leu Lys Ser Gln Leu Thr Ile Ser Lys Asp Thr
                    85                  90                  95

Ser Arg Asn Gln Val Phe Leu Lys Ile Thr Ser Val Asp Thr Ala Asp
                    100                 105                 110

Thr Ala Thr Tyr Tyr Cys Ser Arg Pro Arg Gly Thr Met Asp Ala
                    115                 120                 125

Met Asp Tyr Trp Gly Gln Gly Thr Ser Val Thr Val Ser Ser Gly Gly
            130                 135                 140

Gly Gly Ser Gly Gly Gly Gly Ser Gly Gly Gly Ser Asp Ile Val
145                 150                 155                 160

Met Thr Gln Ala Ala Ser Ser Leu Ser Ala Ser Leu Gly Asp Arg Val
                    165                 170                 175

Thr Ile Ser Cys Arg Ala Ser Gln Asp Ile Ser Lys Tyr Leu Asn Trp
                    180                 185                 190

Tyr Gln Gln Lys Pro Asp Gly Thr Val Lys Leu Leu Ile Tyr Tyr Thr
                    195                 200                 205

Ser Arg Leu His Ser Gly Val Pro Ser Arg Phe Ser Gly Ser Gly Ser
            210                 215                 220

Gly Thr Asp Tyr Ser Leu Thr Ile Arg Asn Leu Glu Gln Glu Asp Ile
225                 230                 235                 240

Ala Thr Tyr Phe Cys Gln Gln Val Tyr Thr Leu Pro Trp Thr Phe Gly
                    245                 250                 255

Gly Gly Thr Lys Leu Glu Ile Lys Ser Gly Thr Thr Thr Pro Ala Pro
                    260                 265                 270

Arg Pro Pro Thr Pro Ala Pro Thr Ile Ala Ser Gln Pro Leu Ser Leu
                    275                 280                 285

Arg Pro Glu Ala Cys Arg Pro Ala Ala Gly Gly Ala Val His Thr Arg
                    290                 295                 300

Gly Leu Asp Phe Ala Cys Asp Ile Tyr Ile Trp Ala Pro Leu Ala Gly
305                 310                 315                 320

Thr Cys Gly Val Leu Leu Leu Ser Leu Val Ile Thr Leu Tyr Cys Lys
                    325                 330                 335

Arg Gly Arg Lys Lys Leu Leu Tyr Ile Phe Lys Gln Pro Phe Met Arg
                    340                 345                 350

Pro Val Gln Thr Thr Gln Glu Glu Asp Gly Cys Ser Cys Arg Phe Pro
                    355                 360                 365

Glu Glu Glu Glu Gly Gly Cys Glu Leu Arg Val Lys Phe Ser Arg Ser
            370                 375                 380

Ala Asp Ala Pro Ala Tyr Lys Gln Gly Gln Asn Gln Leu Tyr Asn Glu
385                 390                 395                 400

Leu Asn Leu Gly Arg Arg Glu Glu Tyr Asp Val Leu Asp Lys Arg Arg
                    405                 410                 415

Gly Arg Asp Pro Glu Met Gly Gly Lys Pro Arg Arg Lys Asn Pro Gln
                    420                 425                 430

Glu Gly Leu Tyr Asn Glu Leu Gln Lys Asp Lys Met Ala Glu Ala Tyr
            435                 440                 445

Ser Glu Ile Gly Met Lys Gly Glu Arg Arg Arg Gly Lys Gly His Asp
            450                 455                 460

Gly Leu Tyr Gln Gly Leu Ser Thr Ala Thr Lys Asp Thr Tyr Asp Ala
465                 470                 475                 480

Leu His Met Gln Ala Leu Pro Pro Arg
                    485
```

```
<210> SEQ ID NO 40
<211> LENGTH: 730
<212> TYPE: PRT
<213> ORGANISM: Artificial Sequence
<220> FEATURE:
<223> OTHER INFORMATION: Synthetic

<400> SEQUENCE: 40

Met Ala Leu Pro Val Thr Ala Leu Leu Pro Leu Ala Leu Leu Leu
1               5                   10                  15

His Ala Ala Arg Pro Gln Val Thr Leu Lys Glu Ser Gly Pro Gly Ile
                20                  25                  30

Leu Lys Pro Ser Gln Thr Leu Ser Leu Thr Cys Ser Phe Ser Gly Phe
        35                  40                  45

Ser Leu Ser Thr Ser Gly Met Gly Val Gly Trp Ile Arg Gln Pro Ser
50                  55                  60

Gly Lys Gly Leu Glu Trp Leu Ala His Ile Trp Trp Asp Asp Asp Lys
65                  70                  75                  80

Tyr Tyr Asn Pro Ser Leu Lys Ser Gln Leu Thr Ile Ser Lys Asp Thr
                85                  90                  95

Ser Arg Asn Gln Val Phe Leu Lys Ile Thr Ser Val Asp Thr Ala Asp
                100                 105                 110

Thr Ala Thr Tyr Tyr Cys Ser Arg Arg Pro Arg Gly Thr Met Asp Ala
            115                 120                 125

Met Asp Tyr Trp Gly Gln Gly Thr Ser Val Thr Val Ser Ser Gly Gly
130                 135                 140

Gly Gly Ser Gly Gly Gly Ser Gly Gly Gly Ser Asp Ile Val
145                 150                 155                 160

Met Thr Gln Ala Ala Ser Ser Leu Ser Ala Ser Leu Gly Asp Arg Val
                165                 170                 175

Thr Ile Ser Cys Arg Ala Ser Gln Asp Ile Ser Lys Tyr Leu Asn Trp
            180                 185                 190

Tyr Gln Gln Lys Pro Asp Gly Thr Val Lys Leu Leu Ile Tyr Tyr Thr
        195                 200                 205

Ser Arg Leu His Ser Gly Val Pro Ser Arg Phe Ser Gly Ser Gly Ser
210                 215                 220

Gly Thr Asp Tyr Ser Leu Thr Ile Arg Asn Leu Glu Gln Glu Asp Ile
225                 230                 235                 240

Ala Thr Tyr Phe Cys Gln Gln Val Tyr Thr Leu Pro Trp Thr Phe Gly
                245                 250                 255

Gly Gly Thr Lys Leu Glu Ile Lys Leu Glu Asp Pro Ala Glu Pro Lys
            260                 265                 270

Ser Pro Asp Lys Thr His Thr Cys Pro Pro Cys Pro Ala Pro Glu Leu
        275                 280                 285

Leu Gly Gly Pro Ser Val Phe Leu Phe Pro Pro Lys Pro Lys Asp Thr
290                 295                 300

Leu Met Ile Ser Arg Thr Pro Glu Val Thr Cys Val Val Val Asp Val
305                 310                 315                 320

Ser His Glu Asp Pro Glu Val Lys Phe Asn Trp Tyr Val Asp Gly Val
                325                 330                 335

Glu Val His Asn Ala Lys Thr Lys Pro Arg Glu Glu Gln Tyr Asn Ser
            340                 345                 350

Thr Tyr Arg Val Val Ser Val Leu Thr Val Leu His Gln Asp Trp Leu
        355                 360                 365
```

Asn Gly Lys Glu Tyr Lys Cys Lys Val Ser Asn Lys Ala Leu Pro Ala
            370                 375                 380

Pro Ile Glu Lys Thr Ile Ser Lys Ala Lys Gly Gln Pro Arg Glu Pro
385                 390                 395                 400

Gln Val Tyr Thr Leu Pro Pro Ser Arg Asp Glu Leu Thr Lys Asn Gln
                405                 410                 415

Val Ser Leu Thr Cys Leu Val Lys Gly Phe Tyr Pro Ser Asp Ile Ala
                420                 425                 430

Val Glu Trp Glu Ser Asn Gly Gln Pro Glu Asn Asn Tyr Lys Thr Thr
            435                 440                 445

Pro Pro Val Leu Asp Ser Asp Gly Ser Phe Phe Leu Tyr Ser Lys Leu
450                 455                 460

Thr Val Asp Lys Ser Arg Trp Gln Gln Gly Asn Val Phe Ser Cys Ser
465                 470                 475                 480

Val Met His Glu Ala Leu His Asn His Tyr Thr Gln Lys Ser Leu Ser
                485                 490                 495

Leu Ser Pro Gly Lys Lys Asp Pro Lys Ser Gly Thr Thr Thr Pro Ala
            500                 505                 510

Pro Arg Pro Pro Thr Pro Ala Pro Thr Ile Ala Ser Gln Pro Leu Ser
            515                 520                 525

Leu Arg Pro Glu Ala Cys Arg Pro Ala Ala Gly Gly Ala Val His Thr
            530                 535                 540

Arg Gly Leu Asp Phe Ala Cys Asp Ile Tyr Ile Trp Ala Pro Leu Ala
545                 550                 555                 560

Gly Thr Cys Gly Val Leu Leu Leu Ser Leu Val Ile Thr Leu Tyr Cys
                565                 570                 575

Lys Arg Gly Arg Lys Lys Leu Leu Tyr Ile Phe Lys Gln Pro Phe Met
            580                 585                 590

Arg Pro Val Gln Thr Thr Gln Glu Glu Asp Gly Cys Ser Cys Arg Phe
            595                 600                 605

Pro Glu Glu Glu Glu Gly Gly Cys Glu Leu Arg Val Lys Phe Ser Arg
610                 615                 620

Ser Ala Asp Ala Pro Ala Tyr Lys Gln Gly Gln Asn Gln Leu Tyr Asn
625                 630                 635                 640

Glu Leu Asn Leu Gly Arg Arg Glu Glu Tyr Asp Val Leu Asp Lys Arg
                645                 650                 655

Arg Gly Arg Asp Pro Glu Met Gly Gly Lys Pro Arg Arg Lys Asn Pro
            660                 665                 670

Gln Glu Gly Leu Tyr Asn Glu Leu Gln Lys Asp Lys Met Ala Glu Ala
            675                 680                 685

Tyr Ser Glu Ile Gly Met Lys Gly Glu Arg Arg Arg Gly Lys Gly His
            690                 695                 700

Asp Gly Leu Tyr Gln Gly Leu Ser Thr Ala Thr Lys Asp Thr Tyr Asp
705                 710                 715                 720

Ala Leu His Met Gln Ala Leu Pro Pro Arg
                725                 730

<210> SEQ ID NO 41
<211> LENGTH: 491
<212> TYPE: PRT
<213> ORGANISM: Artificial Sequence
<220> FEATURE:
<223> OTHER INFORMATION: Synthetic

<400> SEQUENCE: 41

-continued

```
Met Ala Leu Pro Val Thr Ala Leu Leu Leu Pro Leu Ala Leu Leu Leu
1               5                   10                  15

His Ala Ala Arg Pro Gln Val Thr Leu Lys Glu Ser Gly Pro Gly Ile
            20                  25                  30

Leu Lys Pro Ser Gln Thr Leu Ser Leu Thr Cys Ser Phe Ser Gly Phe
        35                  40                  45

Ser Leu Asn Thr Ser Gly Met Gly Val Gly Trp Ile Arg Gln Pro Ser
    50                  55                  60

Gly Lys Gly Leu Glu Trp Leu Ala His Ile Trp Trp Asp Asp Asp Lys
65                  70                  75                  80

Tyr Tyr Asn Pro Ser Leu Lys Ser Gln Leu Thr Ile Ser Lys Asp Thr
                85                  90                  95

Ser Arg Asn Gln Val Phe Leu Lys Ile Thr Ser Val Asp Thr Ala Asp
            100                 105                 110

Ser Ala Thr Tyr Tyr Cys Ala Arg Arg Ala Ser His Val Ser Thr Val
        115                 120                 125

Asp Ser Phe Asp Phe Trp Gly Gln Gly Thr Thr Leu Thr Val Ser Ser
    130                 135                 140

Gly Gly Gly Gly Ser Gly Gly Gly Ser Gly Gly Gly Gly Ser Asp
145                 150                 155                 160

Ile Gln Met Thr Gln Thr Thr Ser Ser Leu Ser Ala Ser Leu Gly Asp
            165                 170                 175

Arg Val Thr Ile Ser Cys Arg Ala Ser Gln Asp Ile Ser Asn Tyr Leu
        180                 185                 190

Asn Trp Phe Gln Gln Lys Pro Asp Gly Thr Val Lys Leu Leu Ile Tyr
    195                 200                 205

Tyr Thr Ser Arg Leu His Ser Gly Val Pro Ser Lys Phe Ser Gly Ser
210                 215                 220

Gly Ser Gly Thr Asp Tyr Ser Leu Thr Ile Ser Asn Leu Glu Gln Glu
225                 230                 235                 240

Asp Ile Ala Thr Tyr Phe Cys Gln Gln Gly Tyr Thr Leu Pro Trp Thr
            245                 250                 255

Phe Gly Gly Gly Thr Lys Leu Glu Ile Lys Ser Gly Thr Thr Thr Pro
        260                 265                 270

Ala Pro Arg Pro Pro Thr Pro Ala Pro Thr Ile Ala Ser Gln Pro Leu
    275                 280                 285

Ser Leu Arg Pro Glu Ala Cys Arg Pro Ala Ala Gly Gly Ala Val His
    290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Leu Ser Leu Val Ile Thr Leu Tyr
            325                 330                 335

Cys Lys Arg Gly Arg Lys Lys Leu Leu Tyr Ile Phe Lys Gln Pro Phe
        340                 345                 350

Met Arg Pro Val Gln Thr Thr Gln Glu Glu Asp Gly Cys Ser Cys Arg
    355                 360                 365

Phe Pro Glu Glu Glu Glu Gly Gly Cys Glu Leu Arg Val Lys Phe Ser
    370                 375                 380

Arg Ser Ala Asp Ala Pro Ala Tyr Lys Gln Gly Gln Asn Gln Leu Tyr
385                 390                 395                 400

Asn Glu Leu Asn Leu Gly Arg Arg Glu Glu Tyr Asp Val Leu Asp Lys
            405                 410                 415
```

```
Arg Arg Gly Arg Asp Pro Glu Met Gly Lys Pro Arg Arg Lys Asn
            420                 425                 430

Pro Gln Glu Gly Leu Tyr Asn Glu Leu Gln Lys Asp Lys Met Ala Glu
        435                 440                 445

Ala Tyr Ser Glu Ile Gly Met Lys Gly Glu Arg Arg Arg Gly Lys Gly
    450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
                485                 490

<210> SEQ ID NO 42
<211> LENGTH: 732
<212> TYPE: PRT
<213> ORGANISM: Artificial Sequence
<220> FEATURE:
<223> OTHER INFORMATION: Synthetic

<400> SEQUENCE: 42

Met Ala Leu Pro Val Thr Ala Leu Leu Leu Pro Leu Ala Leu Leu Leu
1               5                   10                  15

His Ala Ala Arg Pro Gln Val Thr Leu Lys Glu Ser Gly Pro Gly Ile
            20                  25                  30

Leu Lys Pro Ser Gln Thr Leu Ser Leu Thr Cys Ser Phe Ser Gly Phe
        35                  40                  45

Ser Leu Asn Thr Ser Gly Met Gly Val Gly Trp Ile Arg Gln Pro Ser
    50                  55                  60

Gly Lys Gly Leu Glu Trp Leu Ala His Ile Trp Asp Asp Asp Lys
65                  70                  75                  80

Tyr Tyr Asn Pro Ser Leu Lys Ser Gln Leu Thr Ile Ser Lys Asp Thr
                85                  90                  95

Ser Arg Asn Gln Val Phe Leu Lys Ile Thr Ser Val Asp Thr Ala Asp
            100                 105                 110

Ser Ala Thr Tyr Tyr Cys Ala Arg Arg Ala Ser His Val Ser Thr Val
        115                 120                 125

Asp Ser Phe Asp Phe Trp Gly Gln Gly Thr Thr Leu Thr Val Ser Ser
    130                 135                 140

Gly Gly Gly Gly Ser Gly Gly Gly Ser Gly Gly Gly Gly Ser Asp
145                 150                 155                 160

Ile Gln Met Thr Gln Thr Thr Ser Ser Leu Ser Ala Ser Leu Gly Asp
                165                 170                 175

Arg Val Thr Ile Ser Cys Arg Ala Ser Gln Asp Ile Ser Asn Tyr Leu
            180                 185                 190

Asn Trp Phe Gln Gln Lys Pro Asp Gly Thr Val Lys Leu Leu Ile Tyr
        195                 200                 205

Tyr Thr Ser Arg Leu His Ser Gly Val Pro Ser Lys Phe Ser Gly Ser
    210                 215                 220

Gly Ser Gly Thr Asp Tyr Ser Leu Thr Ile Ser Asn Leu Glu Gln Glu
225                 230                 235                 240

Asp Ile Ala Thr Tyr Phe Cys Gln Gln Gly Tyr Thr Leu Pro Trp Thr
                245                 250                 255

Phe Gly Gly Gly Thr Lys Leu Glu Ile Lys Leu Glu Asp Pro Ala Glu
            260                 265                 270

Pro Lys Ser Pro Asp Lys Thr His Thr Cys Pro Pro Cys Pro Ala Pro
        275                 280                 285
```

-continued

Glu Leu Leu Gly Gly Pro Ser Val Phe Leu Phe Pro Pro Lys Pro Lys
290                 295                 300

Asp Thr Leu Met Ile Ser Arg Thr Pro Glu Val Thr Cys Val Val Val
305                 310                 315                 320

Asp Val Ser His Glu Asp Pro Glu Val Lys Phe Asn Trp Tyr Val Asp
            325                 330                 335

Gly Val Glu Val His Asn Ala Lys Thr Lys Pro Arg Glu Glu Gln Tyr
                340                 345                 350

Asn Ser Thr Tyr Arg Val Val Ser Val Leu Thr Val Leu His Gln Asp
        355                 360                 365

Trp Leu Asn Gly Lys Glu Tyr Lys Cys Lys Val Ser Asn Lys Ala Leu
370                 375                 380

Pro Ala Pro Ile Glu Lys Thr Ile Ser Lys Ala Lys Gly Gln Pro Arg
385                 390                 395                 400

Glu Pro Gln Val Tyr Thr Leu Pro Pro Ser Arg Asp Glu Leu Thr Lys
                405                 410                 415

Asn Gln Val Ser Leu Thr Cys Leu Val Lys Gly Phe Tyr Pro Ser Asp
            420                 425                 430

Ile Ala Val Glu Trp Glu Ser Asn Gly Gln Pro Glu Asn Asn Tyr Lys
        435                 440                 445

Thr Thr Pro Pro Val Leu Asp Ser Asp Gly Ser Phe Phe Leu Tyr Ser
450                 455                 460

Lys Leu Thr Val Asp Lys Ser Arg Trp Gln Gln Gly Asn Val Phe Ser
465                 470                 475                 480

Cys Ser Val Met His Glu Ala Leu His Asn His Tyr Thr Gln Lys Ser
                485                 490                 495

Leu Ser Leu Ser Pro Gly Lys Lys Asp Pro Lys Ser Gly Thr Thr Thr
            500                 505                 510

Pro Ala Pro Arg Pro Pro Thr Pro Ala Pro Thr Ile Ala Ser Gln Pro
        515                 520                 525

Leu Ser Leu Arg Pro Glu Ala Cys Arg Pro Ala Ala Gly Gly Ala Val
530                 535                 540

His Thr Arg Gly Leu Asp Phe Ala Cys Asp Ile Tyr Ile Trp Ala Pro
545                 550                 555                 560

Leu Ala Gly Thr Cys Gly Val Leu Leu Leu Ser Leu Val Ile Thr Leu
                565                 570                 575

Tyr Cys Lys Arg Gly Arg Lys Lys Leu Leu Tyr Ile Phe Lys Gln Pro
            580                 585                 590

Phe Met Arg Pro Val Gln Thr Thr Gln Glu Glu Asp Gly Cys Ser Cys
        595                 600                 605

Arg Phe Pro Glu Glu Glu Glu Gly Gly Cys Glu Leu Arg Val Lys Phe
610                 615                 620

Ser Arg Ser Ala Asp Ala Pro Ala Tyr Lys Gln Gly Gln Asn Gln Leu
625                 630                 635                 640

Tyr Asn Glu Leu Asn Leu Gly Arg Arg Glu Glu Tyr Asp Val Leu Asp
                645                 650                 655

Lys Arg Arg Gly Arg Asp Pro Glu Met Gly Gly Lys Pro Arg Arg Lys
            660                 665                 670

Asn Pro Gln Glu Gly Leu Tyr Asn Glu Leu Gln Lys Asp Lys Met Ala
        675                 680                 685

Glu Ala Tyr Ser Glu Ile Gly Met Lys Gly Glu Arg Arg Arg Gly Lys
690                 695                 700

Gly His Asp Gly Leu Tyr Gln Gly Leu Ser Thr Ala Thr Lys Asp Thr

```
                705                 710                 715                 720
Tyr Asp Ala Leu His Met Gln Ala Leu Pro Pro Arg
                    725                 730
```

<210> SEQ ID NO 43
<211> LENGTH: 468
<212> TYPE: PRT
<213> ORGANISM: Artificial Sequence
<220> FEATURE:
<223> OTHER INFORMATION: Synthetic

<400> SEQUENCE: 43

```
Gln Val Thr Leu Lys Glu Ser Gly Pro Gly Ile Leu Lys Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp Asp Asp Lys Tyr Tyr Asn Pro Ser
    50                  55                  60

Leu Lys Ser Gln Leu Thr Ile Ser Lys Asp Thr Ser Arg Asn Gln Val
65                  70                  75                  80

Phe Leu Lys Ile Thr Ser Val Asp Thr Ala Asp Thr Ala Thr Tyr Tyr
                85                  90                  95

Cys Ser Arg Arg Pro Arg Gly Thr Met Asp Ala Met Asp Tyr Trp Gly
            100                 105                 110

Gln Gly Thr Ser Val Thr Val Ser Ser Gly Gly Gly Ser Gly Gly
        115                 120                 125

Gly Gly Ser Gly Gly Gly Ser Asp Ile Val Met Thr Gln Ala Ala
    130                 135                 140

Ser Ser Leu Ser Ala Ser Leu Gly Asp Arg Val Thr Ile Ser Cys Arg
145                 150                 155                 160

Ala Ser Gln Asp Ile Ser Lys Tyr Leu Asn Trp Tyr Gln Gln Lys Pro
                165                 170                 175

Asp Gly Thr Val Lys Leu Leu Ile Tyr Tyr Thr Ser Arg Leu His Ser
            180                 185                 190

Gly Val Pro Ser Arg Phe Ser Gly Ser Gly Ser Gly Thr Asp Tyr Ser
        195                 200                 205

Leu Thr Ile Arg Asn Leu Glu Gln Glu Asp Ile Ala Thr Tyr Phe Cys
    210                 215                 220

Gln Gln Val Tyr Thr Leu Pro Trp Thr Phe Gly Gly Gly Thr Lys Leu
225                 230                 235                 240

Glu Ile Lys Ser Gly Thr Thr Thr Pro Ala Pro Arg Pro Pro Thr Pro
                245                 250                 255

Ala Pro Thr Ile Ala Ser Gln Pro Leu Ser Leu Arg Pro Glu Ala Cys
            260                 265                 270

Arg Pro Ala Ala Gly Gly Ala Val His Thr Arg Gly Leu Asp Phe Ala
        275                 280                 285

Cys Asp Ile Tyr Ile Trp Ala Pro Leu Ala Gly Thr Cys Gly Val Leu
    290                 295                 300

Leu Leu Ser Leu Val Ile Thr Leu Tyr Cys Lys Arg Gly Arg Lys Lys
305                 310                 315                 320

Leu Leu Tyr Ile Phe Lys Gln Pro Phe Met Arg Pro Val Gln Thr Thr
                325                 330                 335

Gln Glu Glu Asp Gly Cys Ser Cys Arg Phe Pro Glu Glu Glu Glu Gly
```

```
            340                 345                 350
Gly Cys Glu Leu Arg Val Lys Phe Ser Arg Ser Ala Asp Ala Pro Ala
        355                 360                 365

Tyr Lys Gln Gly Gln Asn Gln Leu Tyr Asn Glu Leu Asn Leu Gly Arg
    370                 375                 380

Arg Glu Glu Tyr Asp Val Leu Asp Lys Arg Gly Arg Asp Pro Glu
385                 390                 395                 400

Met Gly Gly Lys Pro Arg Arg Lys Asn Pro Gln Glu Gly Leu Tyr Asn
                405                 410                 415

Glu Leu Gln Lys Asp Lys Met Ala Glu Ala Tyr Ser Glu Ile Gly Met
            420                 425                 430

Lys Gly Glu Arg Arg Arg Gly Lys Gly His Asp Gly Leu Tyr Gln Gly
        435                 440                 445

Leu Ser Thr Ala Thr Lys Asp Thr Tyr Asp Ala Leu His Met Gln Ala
    450                 455                 460

Leu Pro Pro Arg
465
```

<210> SEQ ID NO 44
<211> LENGTH: 709
<212> TYPE: PRT
<213> ORGANISM: Artificial Sequence
<220> FEATURE:
<223> OTHER INFORMATION: Synthetic

<400> SEQUENCE: 44

```
Gln Val Thr Leu Lys Glu Ser Gly Pro Gly Ile Leu Lys Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp Asp Asp Lys Tyr Tyr Asn Pro Ser
    50                  55                  60

Leu Lys Ser Gln Leu Thr Ile Ser Lys Asp Thr Ser Arg Asn Gln Val
65                  70                  75                  80

Phe Leu Lys Ile Thr Ser Val Asp Thr Ala Asp Thr Ala Thr Tyr Tyr
                85                  90                  95

Cys Ser Arg Arg Pro Arg Gly Thr Met Asp Ala Met Asp Tyr Trp Gly
            100                 105                 110

Gln Gly Thr Ser Val Thr Val Ser Ser Gly Gly Gly Ser Gly Gly
        115                 120                 125

Gly Gly Ser Gly Gly Gly Ser Asp Ile Val Met Thr Gln Ala Ala
    130                 135                 140

Ser Ser Leu Ser Ala Ser Leu Gly Asp Arg Val Thr Ile Ser Cys Arg
145                 150                 155                 160

Ala Ser Gln Asp Ile Ser Lys Tyr Leu Asn Trp Tyr Gln Gln Lys Pro
                165                 170                 175

Asp Gly Thr Val Lys Leu Leu Ile Tyr Tyr Thr Ser Arg Leu His Ser
            180                 185                 190

Gly Val Pro Ser Arg Phe Ser Gly Ser Gly Ser Gly Thr Asp Tyr Ser
        195                 200                 205

Leu Thr Ile Arg Asn Leu Glu Gln Glu Asp Ile Ala Thr Tyr Phe Cys
    210                 215                 220

Gln Gln Val Tyr Thr Leu Pro Trp Thr Phe Gly Gly Gly Thr Lys Leu
```

-continued

```
            225                 230                 235                 240
Glu Ile Lys Leu Glu Asp Pro Ala Glu Pro Lys Ser Pro Asp Lys Thr
                    245                 250                 255
His Thr Cys Pro Pro Cys Pro Ala Pro Glu Leu Leu Gly Gly Pro Ser
                260                 265                 270
Val Phe Leu Phe Pro Pro Lys Pro Lys Asp Thr Leu Met Ile Ser Arg
            275                 280                 285
Thr Pro Glu Val Thr Cys Val Val Val Asp Val Ser His Glu Asp Pro
        290                 295                 300
Glu Val Lys Phe Asn Trp Tyr Val Asp Gly Val Glu Val His Asn Ala
305                 310                 315                 320
Lys Thr Lys Pro Arg Glu Glu Gln Tyr Asn Ser Thr Tyr Arg Val Val
                325                 330                 335
Ser Val Leu Thr Val Leu His Gln Asp Trp Leu Asn Gly Lys Glu Tyr
                340                 345                 350
Lys Cys Lys Val Ser Asn Lys Ala Leu Pro Ala Pro Ile Glu Lys Thr
            355                 360                 365
Ile Ser Lys Ala Lys Gly Gln Pro Arg Glu Pro Gln Val Tyr Thr Leu
        370                 375                 380
Pro Pro Ser Arg Asp Glu Leu Thr Lys Asn Gln Val Ser Leu Thr Cys
385                 390                 395                 400
Leu Val Lys Gly Phe Tyr Pro Ser Asp Ile Ala Val Glu Trp Glu Ser
                405                 410                 415
Asn Gly Gln Pro Glu Asn Asn Tyr Lys Thr Thr Pro Pro Val Leu Asp
                420                 425                 430
Ser Asp Gly Ser Phe Phe Leu Tyr Ser Lys Leu Thr Val Asp Lys Ser
            435                 440                 445
Arg Trp Gln Gln Gly Asn Val Phe Ser Cys Ser Val Met His Glu Ala
        450                 455                 460
Leu His Asn His Tyr Thr Gln Lys Ser Leu Ser Leu Ser Pro Gly Lys
465                 470                 475                 480
Lys Asp Pro Lys Ser Gly Thr Thr Thr Pro Ala Pro Arg Pro Pro Thr
                485                 490                 495
Pro Ala Pro Thr Ile Ala Ser Gln Pro Leu Ser Leu Arg Pro Glu Ala
                500                 505                 510
Cys Arg Pro Ala Ala Gly Gly Ala Val His Thr Arg Gly Leu Asp Phe
            515                 520                 525
Ala Cys Asp Ile Tyr Ile Trp Ala Pro Leu Ala Gly Thr Cys Gly Val
        530                 535                 540
Leu Leu Leu Ser Leu Val Ile Thr Leu Tyr Cys Lys Arg Gly Arg Lys
545                 550                 555                 560
Lys Leu Leu Tyr Ile Phe Lys Gln Pro Phe Met Arg Pro Val Gln Thr
                565                 570                 575
Thr Gln Glu Glu Asp Gly Cys Ser Cys Arg Phe Pro Glu Glu Glu Glu
                580                 585                 590
Gly Gly Cys Glu Leu Arg Val Lys Phe Ser Arg Ser Ala Asp Ala Pro
            595                 600                 605
Ala Tyr Lys Gln Gly Gln Asn Gln Leu Tyr Asn Glu Leu Asn Leu Gly
        610                 615                 620
Arg Arg Glu Glu Tyr Asp Val Leu Asp Lys Arg Arg Gly Arg Asp Pro
625                 630                 635                 640
Glu Met Gly Gly Lys Pro Arg Arg Lys Asn Pro Gln Glu Gly Leu Tyr
                645                 650                 655
```

```
Asn Glu Leu Gln Lys Asp Lys Met Ala Glu Ala Tyr Ser Glu Ile Gly
                660                 665                 670

Met Lys Gly Glu Arg Arg Gly Lys Gly His Asp Gly Leu Tyr Gln
            675                 680                 685

Gly Leu Ser Thr Ala Thr Lys Asp Thr Tyr Asp Ala Leu His Met Gln
690                 695                 700

Ala Leu Pro Pro Arg
705

<210> SEQ ID NO 45
<211> LENGTH: 470
<212> TYPE: PRT
<213> ORGANISM: Artificial Sequence
<220> FEATURE:
<223> OTHER INFORMATION: Synthetic

<400> SEQUENCE: 45

Gln Val Thr Leu Lys Glu Ser Gly Pro Gly Ile Leu Lys Pro Ser Gln
1               5                   10                  15

Thr Leu Ser Leu Thr Cys Ser Phe Ser Gly Phe Ser Leu Asn Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp Asp Asp Lys Tyr Tyr Asn Pro Ser
    50                  55                  60

Leu Lys Ser Gln Leu Thr Ile Ser Lys Asp Thr Ser Arg Asn Gln Val
65                  70                  75                  80

Phe Leu Lys Ile Thr Ser Val Asp Thr Ala Asp Ser Ala Thr Tyr Tyr
                85                  90                  95

Cys Ala Arg Arg Ala Ser His Val Ser Thr Val Asp Ser Phe Asp Phe
            100                 105                 110

Trp Gly Gln Gly Thr Thr Leu Thr Val Ser Ser Gly Gly Gly Gly Ser
        115                 120                 125

Gly Gly Gly Gly Ser Gly Gly Gly Ser Asp Ile Gln Met Thr Gln
130                 135                 140

Thr Thr Ser Ser Leu Ser Ala Ser Leu Gly Asp Arg Val Thr Ile Ser
145                 150                 155                 160

Cys Arg Ala Ser Gln Asp Ile Ser Asn Tyr Leu Asn Trp Phe Gln Gln
                165                 170                 175

Lys Pro Asp Gly Thr Val Lys Leu Leu Ile Tyr Tyr Thr Ser Arg Leu
            180                 185                 190

His Ser Gly Val Pro Ser Lys Phe Ser Gly Ser Gly Ser Gly Thr Asp
        195                 200                 205

Tyr Ser Leu Thr Ile Ser Asn Leu Glu Gln Glu Asp Ile Ala Thr Tyr
    210                 215                 220

Phe Cys Gln Gln Gly Tyr Thr Leu Pro Trp Thr Phe Gly Gly Gly Thr
225                 230                 235                 240

Lys Leu Glu Ile Lys Ser Gly Thr Thr Thr Pro Ala Pro Arg Pro Pro
                245                 250                 255

Thr Pro Ala Pro Thr Ile Ala Ser Gln Pro Leu Ser Leu Arg Pro Glu
            260                 265                 270

Ala Cys Arg Pro Ala Ala Gly Gly Ala Val His Thr Arg Gly Leu Asp
        275                 280                 285

Phe Ala Cys Asp Ile Tyr Ile Trp Ala Pro Leu Ala Gly Thr Cys Gly
    290                 295                 300
```

```
Val Leu Leu Leu Ser Leu Val Ile Thr Leu Tyr Cys Lys Arg Gly Arg
305                 310                 315                 320

Lys Lys Leu Leu Tyr Ile Phe Lys Gln Pro Phe Met Arg Pro Val Gln
            325                 330                 335

Thr Thr Gln Glu Glu Asp Gly Cys Ser Cys Arg Phe Pro Glu Glu Glu
        340                 345                 350

Glu Gly Gly Cys Glu Leu Arg Val Lys Phe Ser Arg Ser Ala Asp Ala
            355                 360                 365

Pro Ala Tyr Lys Gln Gly Gln Asn Gln Leu Tyr Asn Glu Leu Asn Leu
        370                 375                 380

Gly Arg Arg Glu Glu Tyr Asp Val Leu Asp Lys Arg Arg Gly Arg Asp
385                 390                 395                 400

Pro Glu Met Gly Gly Lys Pro Arg Arg Lys Asn Pro Gln Glu Gly Leu
                405                 410                 415

Tyr Asn Glu Leu Gln Lys Asp Lys Met Ala Glu Ala Tyr Ser Glu Ile
            420                 425                 430

Gly Met Lys Gly Glu Arg Arg Arg Gly Lys Gly His Asp Gly Leu Tyr
            435                 440                 445

Gln Gly Leu Ser Thr Ala Thr Lys Asp Thr Tyr Asp Ala Leu His Met
        450                 455                 460

Gln Ala Leu Pro Pro Arg
465                 470

<210> SEQ ID NO 46
<211> LENGTH: 711
<212> TYPE: PRT
<213> ORGANISM: Artificial Sequence
<220> FEATURE:
<223> OTHER INFORMATION: Synthetic

<400> SEQUENCE: 46

Gln Val Thr Leu Lys Glu Ser Gly Pro Gly Ile Leu Lys Pro Ser Gln
1               5                   10                  15

Thr Leu Ser Leu Thr Cys Ser Phe Ser Gly Phe Ser Leu Asn Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp Asp Asp Lys Tyr Tyr Asn Pro Ser
    50                  55                  60

Leu Lys Ser Gln Leu Thr Ile Ser Lys Asp Thr Ser Arg Asn Gln Val
65                  70                  75                  80

Phe Leu Lys Ile Thr Ser Val Asp Thr Ala Asp Ser Ala Thr Tyr Tyr
                85                  90                  95

Cys Ala Arg Arg Ala Ser His Val Ser Thr Val Asp Ser Phe Asp Phe
            100                 105                 110

Trp Gly Gln Gly Thr Thr Leu Thr Val Ser Ser Gly Gly Gly Gly Ser
        115                 120                 125

Gly Gly Gly Gly Ser Gly Gly Gly Ser Asp Ile Gln Met Thr Gln
130                 135                 140

Thr Thr Ser Ser Leu Ser Ala Ser Leu Gly Asp Arg Val Thr Ile Ser
145                 150                 155                 160

Cys Arg Ala Ser Gln Asp Ile Ser Asn Tyr Leu Asn Trp Phe Gln Gln
                165                 170                 175

Lys Pro Asp Gly Thr Val Lys Leu Leu Ile Tyr Tyr Thr Ser Arg Leu
            180                 185                 190
```

```
His Ser Gly Val Pro Ser Lys Phe Ser Gly Ser Gly Ser Gly Thr Asp
            195                 200                 205
Tyr Ser Leu Thr Ile Ser Asn Leu Glu Gln Glu Asp Ile Ala Thr Tyr
        210                 215                 220
Phe Cys Gln Gln Gly Tyr Thr Leu Pro Trp Thr Phe Gly Gly Gly Thr
225                 230                 235                 240
Lys Leu Glu Ile Lys Leu Glu Asp Pro Ala Glu Pro Lys Ser Pro Asp
                245                 250                 255
Lys Thr His Thr Cys Pro Pro Cys Pro Ala Pro Glu Leu Leu Gly Gly
            260                 265                 270
Pro Ser Val Phe Leu Phe Pro Pro Lys Pro Lys Asp Thr Leu Met Ile
        275                 280                 285
Ser Arg Thr Pro Glu Val Thr Cys Val Val Val Asp Val Ser His Glu
        290                 295                 300
Asp Pro Glu Val Lys Phe Asn Trp Tyr Val Asp Gly Val Glu Val His
305                 310                 315                 320
Asn Ala Lys Thr Lys Pro Arg Glu Glu Gln Tyr Asn Ser Thr Tyr Arg
                325                 330                 335
Val Val Ser Val Leu Thr Val Leu His Gln Asp Trp Leu Asn Gly Lys
            340                 345                 350
Glu Tyr Lys Cys Lys Val Ser Asn Lys Ala Leu Pro Ala Pro Ile Glu
        355                 360                 365
Lys Thr Ile Ser Lys Ala Lys Gly Gln Pro Arg Glu Pro Gln Val Tyr
        370                 375                 380
Thr Leu Pro Pro Ser Arg Asp Glu Leu Thr Lys Asn Gln Val Ser Leu
385                 390                 395                 400
Thr Cys Leu Val Lys Gly Phe Tyr Pro Ser Asp Ile Ala Val Glu Trp
                405                 410                 415
Glu Ser Asn Gly Gln Pro Glu Asn Asn Tyr Lys Thr Thr Pro Pro Val
            420                 425                 430
Leu Asp Ser Asp Gly Ser Phe Phe Leu Tyr Ser Lys Leu Thr Val Asp
        435                 440                 445
Lys Ser Arg Trp Gln Gln Gly Asn Val Phe Ser Cys Ser Val Met His
        450                 455                 460
Glu Ala Leu His Asn His Tyr Thr Gln Lys Ser Leu Ser Leu Ser Pro
465                 470                 475                 480
Gly Lys Lys Asp Pro Lys Ser Gly Thr Thr Thr Pro Ala Pro Arg Pro
                485                 490                 495
Pro Thr Pro Ala Pro Thr Ile Ala Ser Gln Pro Leu Ser Leu Arg Pro
            500                 505                 510
Glu Ala Cys Arg Pro Ala Ala Gly Gly Ala Val His Thr Arg Gly Leu
        515                 520                 525
Asp Phe Ala Cys Asp Ile Tyr Ile Trp Ala Pro Leu Ala Gly Thr Cys
        530                 535                 540
Gly Val Leu Leu Leu Ser Leu Val Ile Thr Leu Tyr Cys Lys Arg Gly
545                 550                 555                 560
Arg Lys Lys Leu Leu Tyr Ile Phe Lys Gln Pro Phe Met Arg Pro Val
                565                 570                 575
Gln Thr Thr Gln Glu Glu Asp Gly Cys Ser Cys Arg Phe Pro Glu Glu
            580                 585                 590
Glu Glu Gly Gly Cys Glu Leu Arg Val Lys Phe Ser Arg Ser Ala Asp
        595                 600                 605
```

```
Ala Pro Ala Tyr Lys Gln Gly Gln Asn Gln Leu Tyr Asn Glu Leu Asn
    610             615                 620
Leu Gly Arg Arg Glu Glu Tyr Asp Val Leu Asp Lys Arg Arg Gly Arg
625             630                 635                 640
Asp Pro Glu Met Gly Gly Lys Pro Arg Arg Lys Asn Pro Gln Glu Gly
                645             650                 655
Leu Tyr Asn Glu Leu Gln Lys Asp Lys Met Ala Glu Ala Tyr Ser Glu
            660             665                 670
Ile Gly Met Lys Gly Glu Arg Arg Arg Gly Lys Gly His Asp Gly Leu
        675             680                 685
Tyr Gln Gly Leu Ser Thr Ala Thr Lys Asp Thr Tyr Asp Ala Leu His
    690             695                 700
Met Gln Ala Leu Pro Pro Arg
705             710
```